(12) United States Patent
Guiheneuf et al.

(10) Patent No.: US 9,410,132 B2
(45) Date of Patent: Aug. 9, 2016

(54) **ACYL-COA: DIACYLGLYCEROL ACYLTRANSFERASE 1-LIKE GENE (*PTDGAT1*) AND USES THEREOF**

(75) Inventors: Freddy Guiheneuf, Sde Boker (IL); Stefan Leu, Midreshet Ben Gurion (IL); Aliza Zarka, Beer Sheva (IL); Inna Khozin-Goldberg, Midreshet Ben Gurion (IL); Sammy Boussiba, Omer (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 403 days.

(21) Appl. No.: 13/883,615

(22) PCT Filed: Nov. 3, 2011

(86) PCT No.: PCT/IL2011/000863
§ 371 (c)(1),
(2), (4) Date: Nov. 1, 2013

(87) PCT Pub. No.: WO2012/059925
PCT Pub. Date: May 10, 2012

(65) Prior Publication Data
US 2014/0196177 A1    Jul. 10, 2014

Related U.S. Application Data

(60) Provisional application No. 61/409,984, filed on Nov. 4, 2010.

(51) Int. Cl.
| | |
|---|---|
| *C12N 15/82* | (2006.01) |
| *C12N 5/14* | (2006.01) |
| *C12N 9/10* | (2006.01) |
| *C07H 21/04* | (2006.01) |
| *C12N 9/18* | (2006.01) |
| *C12P 7/64* | (2006.01) |

(52) U.S. Cl.
CPC ............... *C12N 9/1029* (2013.01); *C12N 9/18* (2013.01); *C12P 7/6409* (2013.01); *C12P 7/6463* (2013.01); *Y02P 20/52* (2015.11)

(58) Field of Classification Search
None
See application file for complete search history.

(56) References Cited

U.S. PATENT DOCUMENTS

2009/0293152 A1*  11/2009  Roesler .............. C12N 15/8247
                                                              800/281

FOREIGN PATENT DOCUMENTS

CN          102 199 580         9/2011

OTHER PUBLICATIONS

Zou et al 1999 (The Plant Journal 19:6 p. 645-653).*
Guo et al. (PNAS (2004) 101: p. 9205-9210).*
Bowler et al 2008 (Nature 456:13 p. 239-244).*
Cloneminer product manual 2003 (Invitrogen).*
RecName: Full=0=acyltransferase; flags: Fragment; the whole document & Bowler Chris et al: "The Phaeodactylum genome reveals the evolutionary history of diatom genomes", Nature, Nature Publishing Group, United Kingdom, vol. 465, No. 7219, Nov. 13, 2008, pp. 239-244.
Khozin-Goldberg I et al: "Unraveling algal lipid metabolism: Recent advances in gene identification", Biochimie, Masson, Paris, FR, vol. 93, No. 1, Aug. 13, 2010, pp. 91-100 pp. 93, col. 2—p. 95, col. 2.
Freddy Guihéneuf et al: "Cloning and molecular characterization of a novel acyl-CoA:diacylglycerol acyltransferase 1-like gene (PtDGAT1) from the diatom Phaeodactylum tricornutum", FEBS Journal, vol. 278, No. 19, Oct. 6, 2011, pp. 3651-3666.

* cited by examiner

*Primary Examiner* — Brent Page
*Assistant Examiner* — Matthew Keogh
(74) *Attorney, Agent, or Firm* — Roach Brown McCarthy & Gruber, P.C.; Kevin D. McCarthy

(57) ABSTRACT

An isolated protein which is at least partially encoded by a polynucleotide sequence encoding a novel acyl-CoA: diacylglycerol acyltransferase 1-like gene (PtDGAT1) from the diatom *Phaeodactylum tricomutum* is provided together with a composition which includes the isolated protein and a transgenic organism transformed by a polynucleotide encoding same. The invention also provides a method for producing or enhancing the production of oil or triacylglycerols with high saturated fatty acids content.

18 Claims, 20 Drawing Sheets

FIG. 3

MDETEITPLLRFSTPSRAEHSSWIKLASESCAYSETDEFLADEAARATQRALQHQEALQMA
QAMPGAKPGTLPPLYFAPTIKRSRSFAKLQEHHGDGMPRVNMRRTKSRDFNADKLDARST
KGYPPSKPMHRAAEPSYLSADAPIQNYRGFLNLGVIILIVSNFRLILGTIRSNGFVLTTAVKH
YKNLNHLKEDPWQEFPFVSGFLLQLVFVSIAFGIEWMLCRKYFNENFGMILHHFNAHSALL
IPLGIVWNLIDRPAVGAILLLHATITWMKLISYMLANEDYRLSS**RRVGGNPHLATLALVEN
LD**SDEANINYPQNVTLRNIFYFWCAPTLTYQIAFPKSPRVRYWKIADILMRMTVSIALFTFL
LAQIVQPALEELVSDLDETNGSYTAAIFAEYWLKLSIANTYLWLLMFYTYFHLYLNLFAEL
LRFGDRVFYKDWWNSSEVSAYWRLWNMPVHYWLIRHVYFPCVRLKMPKVAATFVVFFL
SAVMHEVLVSVPFHIIRPWSFIGMMMQIPLVAFTKYLYRKFPGGSIGNVLFWMTFCVIGQP
MAILLYYHDIMNRKGN\* (SEQ ID NO: 25)

MTTPVSSEDTATLQQKIVALQAQLLSATHALERMKNERGASSADHSKSAQRNGSDPSSDPT
GTAPVAAPPAKSGYLFKELDRAIGWGGIKWSLRYVKLESGRISYYGSHHDTSPRYELQLRG
CAVRDDGWKRNPRFKTKRNEPPPLLDTTGAYFFLFSVYHAPDAAEKEIDETEITPLLRFSTP
SRAEHSSWIKLASESCAYSETDEFLADEAARATQRALQHQEALQMAQAMPGAKPGTLPPL
YFAPTIKRSRSFAKLQEHHGDGMPRVNMRRTKSRDFNADKLDARSTKGYPPSKPMHRAAE
PSYLSADAPIQNYRGFLNLGVIILIVSNFRLILGTIRSNGFVLTTAVKHYKNLNHLKEDPWQE
FPFVSGFLLQLVFVSIAFGIEWMLCRKYFNENFGMILHHFNAHSALLIPLGIVWNLIDRPAV
GAILLLHATITWMKLISYMLANEDYRLSSRRVGGNPHLATLALVENLDSDEANINYPQNVT
LRNIFYFWCAPTLTYQIAFPKSPRVRYWKIADILMRMTVSIALFTFLLAQIVQPALEELVSDL
DETNGSYTAAIFAEYWLKLSIANTYLWLLMFYTYFHLYLNLFAELLRFGDRVFYKDWWNS
SEVSAYWRLWNMPVHYWLIRHVYFPCVRLKMPKVAATFVVFFLSAVMHEVLVSVPFHIIR
PWSFIGMMMQIPLVAFTKYLYRKFPGGSFGNVLFWMTFCVIGQPMAILLYTVDYQYGKHH
STNMEIFDTDDCRFLWKNSCLIR    (SEQ ID NO: 33)

SEQUENCE LISTING

<160> NUMBER OF SEQ ID NOS: 33

<210> SEQ ID NO 1
<211> LENGTH: 553
<212> TYPE: PRT
<213> ORGANISM: Phaeodactylum tricornutum

<400> SEQUENCE: 1

```
Asp Glu Thr Glu Ile Thr Pro Leu Leu Arg Phe Ser Thr Pro Ser Arg
1               5                   10                  15

Ala Glu His Ser Ser Trp Ile Lys Leu Ala Ser Glu Ser Cys Ala Tyr
            20                  25                  30

Ser Glu Thr Asp Glu Phe Leu Ala Asp Glu Ala Arg Ala Thr Gln
        35                  40                  45

Arg Ala Leu Gln His Gln Glu Ala Leu Gln Met Ala Gln Ala Met Pro
    50                  55                  60

Gly Ala Lys Pro Gly Thr Leu Pro Pro Leu Tyr Phe Ala Pro Thr Ile
65                  70                  75                  80

Lys Arg Ser Arg Ser Phe Ala Lys Leu Gln Glu His His Gly Asp Gly
                85                  90                  95

Met Pro Arg Val Asn Met Arg Arg Thr Lys Ser Arg Asp Phe Asn Ala
            100                 105                 110

Asp Lys Leu Asp Ala Arg Ser Thr Lys Gly Tyr Pro Pro Ser Lys Pro
        115                 120                 125

Met His Arg Ala Ala Glu Pro Ser Tyr Leu Ser Ala Asp Ala Pro Ile
    130                 135                 140

Gln Asn Tyr Arg Gly Phe Leu Asn Leu Gly Val Ile Ile Leu Ile Val
145                 150                 155                 160

Ser Asn Phe Arg Leu Ile Leu Gly Thr Ile Arg Ser Asn Gly Phe Val
                165                 170                 175

Leu Thr Thr Ala Val Lys His Tyr Lys Asn Leu Asn His Leu Lys Glu
            180                 185                 190

Asp Pro Trp Gln Glu Phe Pro Phe Val Ser Gly Phe Leu Leu Gln Leu
        195                 200                 205

Val Phe Val Ser Ile Ala Phe Gly Ile Glu Trp Met Leu Cys Arg Lys
    210                 215                 220

Tyr Phe Asn Glu Asn Phe Gly Met Ile Leu His Phe Asn Ala His
225                 230                 235                 240

Ser Ala Leu Leu Ile Pro Leu Gly Ile Val Trp Asn Leu Ile Asp Arg
                245                 250                 255

Pro Ala Val Gly Ala Ile Leu Leu His Ala Thr Ile Thr Trp Met
            260                 265                 270

Lys Leu Ile Ser Tyr Met Leu Ala Asn Glu Asp Tyr Arg Leu Ser Ser
        275                 280                 285

Arg Arg Val Gly Gly Asn Pro His Leu Ala Thr Leu Ala Leu Val Glu
    290                 295                 300

Asn Leu Asp Ser Asp Glu Ala Asn Ile Asn Tyr Pro Gln Asn Val Thr
305                 310                 315                 320

Leu Arg Asn Ile Phe Tyr Phe Trp Cys Ala Pro Thr Leu Thr Tyr Gln
                325                 330                 335

Ile Ala Phe Pro Lys Ser Pro Arg Val Arg Tyr Trp Lys Ile Ala Asp
            340                 345                 350

Ile Leu Met Arg Met Thr Val Ser Ile Ala Leu Phe Thr Phe Leu Leu
        355                 360                 365
```

```
Ala Gln Ile Val Gln Pro Ala Leu Glu Glu Leu Val Ser Asp Leu Asp
        370                 375                 380

Glu Thr Asn Gly Ser Tyr Thr Ala Ala Ile Phe Ala Glu Tyr Trp Leu
385                 390                 395                 400

Lys Leu Ser Ile Ala Asn Thr Tyr Leu Trp Leu Leu Met Phe Tyr Thr
                405                 410                 415

Tyr Phe His Leu Tyr Leu Asn Leu Phe Ala Glu Leu Leu Arg Phe Gly
            420                 425                 430

Asp Arg Val Phe Tyr Lys Asp Trp Trp Asn Ser Ser Glu Val Ser Ala
        435                 440                 445

Tyr Trp Arg Leu Trp Asn Met Pro Val His Tyr Trp Leu Ile Arg His
450                 455                 460

Val Tyr Phe Pro Cys Val Arg Leu Lys Met Pro Lys Val Ala Ala Thr
465                 470                 475                 480

Phe Val Val Phe Phe Leu Ser Ala Val Met His Glu Val Leu Val Ser
                485                 490                 495

Val Pro Phe His Ile Ile Arg Pro Trp Ser Phe Ile Gly Met Met Met
            500                 505                 510

Gln Ile Pro Leu Val Ala Phe Thr Lys Tyr Leu Tyr Arg Lys Phe Pro
        515                 520                 525

Gly Gly Ser Ile Gly Asn Val Leu Phe Trp Met Thr Phe Cys Val Ile
530                 535                 540

Gly Gln Pro Met Ala Ile Leu Leu Tyr
545                 550

<210> SEQ ID NO 2
<211> LENGTH: 554
<212> TYPE: PRT
<213> ORGANISM: Phaeodactylum tricornutum

<400> SEQUENCE: 2

Met Asp Glu Thr Glu Ile Thr Pro Leu Leu Arg Phe Ser Thr Pro Ser
1               5                   10                  15

Arg Ala Glu His Ser Ser Trp Ile Lys Leu Ala Ser Glu Ser Cys Ala
            20                  25                  30

Tyr Ser Glu Thr Asp Glu Phe Leu Ala Asp Glu Ala Ala Arg Ala Thr
        35                  40                  45

Gln Arg Ala Leu Gln His Gln Glu Ala Leu Gln Met Ala Gln Ala Met
    50                  55                  60

Pro Gly Ala Lys Pro Gly Thr Leu Pro Pro Leu Tyr Phe Ala Pro Thr
65                  70                  75                  80

Ile Lys Arg Ser Arg Ser Phe Ala Lys Leu Gln Glu His His Gly Asp
                85                  90                  95

Gly Met Pro Arg Val Asn Met Arg Thr Lys Ser Arg Asp Phe Asn
            100                 105                 110

Ala Asp Lys Leu Asp Ala Arg Ser Thr Lys Gly Tyr Pro Pro Ser Lys
        115                 120                 125

Pro Met His Arg Ala Ala Glu Pro Ser Tyr Leu Ser Ala Asp Ala Pro
    130                 135                 140

Ile Gln Asn Tyr Arg Gly Phe Leu Asn Leu Gly Val Ile Ile Leu Ile
145                 150                 155                 160

Val Ser Asn Phe Arg Leu Ile Leu Gly Thr Ile Arg Ser Asn Gly Phe
                165                 170                 175

Val Leu Thr Thr Ala Val Lys His Tyr Lys Asn Leu Asn His Leu Lys
            180                 185                 190
```

```
Glu Asp Pro Trp Gln Glu Phe Pro Phe Val Ser Gly Phe Leu Leu Gln
        195                 200                 205

Leu Val Phe Val Ser Ile Ala Phe Gly Ile Glu Trp Met Leu Cys Arg
210                 215                 220

Lys Tyr Phe Asn Glu Asn Phe Gly Met Ile Leu His His Phe Asn Ala
225                 230                 235                 240

His Ser Ala Leu Leu Ile Pro Leu Gly Ile Val Trp Asn Leu Ile Asp
                245                 250                 255

Arg Pro Ala Val Gly Ala Ile Leu Leu Leu His Ala Thr Ile Thr Trp
                260                 265                 270

Met Lys Leu Ile Ser Tyr Met Leu Ala Asn Glu Asp Tyr Arg Leu Ser
        275                 280                 285

Ser Arg Arg Val Gly Gly Asn Pro His Leu Ala Thr Leu Ala Leu Val
        290                 295                 300

Glu Asn Leu Asp Ser Asp Glu Ala Asn Ile Asn Tyr Pro Gln Asn Val
305                 310                 315                 320

Thr Leu Arg Asn Ile Phe Tyr Phe Trp Cys Ala Pro Thr Leu Thr Tyr
                325                 330                 335

Gln Ile Ala Phe Pro Lys Ser Pro Arg Val Arg Tyr Trp Lys Ile Ala
                340                 345                 350

Asp Ile Leu Met Arg Met Thr Val Ser Ile Ala Leu Phe Thr Phe Leu
        355                 360                 365

Leu Ala Gln Ile Val Gln Pro Ala Leu Glu Glu Leu Val Ser Asp Leu
        370                 375                 380

Asp Glu Thr Asn Gly Ser Tyr Thr Ala Ala Ile Phe Ala Glu Tyr Trp
385                 390                 395                 400

Leu Lys Leu Ser Ile Ala Asn Thr Tyr Leu Trp Leu Leu Met Phe Tyr
                405                 410                 415

Thr Tyr Phe His Leu Tyr Leu Asn Leu Phe Ala Glu Leu Leu Arg Phe
                420                 425                 430

Gly Asp Arg Val Phe Tyr Lys Asp Trp Trp Asn Ser Ser Glu Val Ser
        435                 440                 445

Ala Tyr Trp Arg Leu Trp Asn Met Pro Val His Tyr Trp Leu Ile Arg
        450                 455                 460

His Val Tyr Phe Pro Cys Val Arg Leu Lys Met Pro Lys Val Ala Ala
465                 470                 475                 480

Thr Phe Val Val Phe Phe Leu Ser Ala Val Met His Glu Val Leu Val
                485                 490                 495

Ser Val Pro Phe His Ile Ile Arg Pro Trp Ser Phe Ile Gly Met Met
                500                 505                 510

Met Gln Ile Pro Leu Val Ala Phe Thr Lys Tyr Leu Tyr Arg Lys Phe
        515                 520                 525

Pro Gly Gly Ser Ile Gly Asn Val Leu Phe Trp Met Thr Phe Cys Val
        530                 535                 540

Ile Gly Gln Pro Met Ala Ile Leu Leu Tyr
545                 550
```

<210> SEQ ID NO 3
<211> LENGTH: 564
<212> TYPE: PRT
<213> ORGANISM: Phaeodactylum tricornutum

<400> SEQUENCE: 3

Met Asp Glu Thr Glu Ile Thr Pro Leu Leu Arg Phe Ser Thr Pro Ser

```
  1               5                   10                  15
Arg Ala Glu His Ser Ser Trp Ile Lys Leu Ala Ser Glu Ser Cys Ala
                  20                  25                  30
Tyr Ser Glu Thr Asp Glu Phe Leu Ala Asp Glu Ala Ala Arg Ala Thr
                  35                  40                  45
Gln Arg Ala Leu Gln His Gln Glu Ala Leu Gln Met Ala Gln Ala Met
                  50                  55                  60
Pro Gly Ala Lys Pro Gly Thr Leu Pro Pro Leu Tyr Phe Ala Pro Thr
 65                  70                  75                  80
Ile Lys Arg Ser Arg Ser Phe Ala Lys Leu Gln Glu His His Gly Asp
                  85                  90                  95
Gly Met Pro Arg Val Asn Met Arg Arg Thr Lys Ser Arg Asp Phe Asn
                 100                 105                 110
Ala Asp Lys Leu Asp Ala Arg Ser Thr Lys Gly Tyr Pro Pro Ser Lys
                 115                 120                 125
Pro Met His Arg Ala Ala Glu Pro Ser Tyr Leu Ser Ala Asp Ala Pro
                 130                 135                 140
Ile Gln Asn Tyr Arg Gly Phe Leu Asn Leu Gly Val Ile Ile Leu Ile
145                 150                 155                 160
Val Ser Asn Phe Arg Leu Ile Leu Gly Thr Ile Arg Ser Asn Gly Phe
                 165                 170                 175
Val Leu Thr Thr Ala Val Lys His Tyr Lys Asn Leu Asn His Leu Lys
                 180                 185                 190
Glu Asp Pro Trp Gln Glu Phe Pro Phe Val Ser Gly Phe Leu Leu Gln
                 195                 200                 205
Leu Val Phe Val Ser Ile Ala Phe Gly Ile Glu Trp Met Leu Cys Arg
                 210                 215                 220
Lys Tyr Phe Asn Glu Asn Phe Gly Met Ile Leu His His Phe Asn Ala
225                 230                 235                 240
His Ser Ala Leu Leu Ile Pro Leu Gly Ile Val Trp Asn Leu Ile Asp
                 245                 250                 255
Arg Pro Ala Val Gly Ala Ile Leu Leu His Ala Thr Ile Thr Trp
                 260                 265                 270
Met Lys Leu Ile Ser Tyr Met Leu Ala Asn Glu Asp Tyr Arg Leu Ser
                 275                 280                 285
Ser Arg Arg Val Gly Gly Asn Pro His Leu Ala Thr Leu Ala Leu Val
                 290                 295                 300
Glu Asn Leu Asp Ser Asp Glu Ala Asn Ile Asn Tyr Pro Gln Asn Val
305                 310                 315                 320
Thr Leu Arg Asn Ile Phe Tyr Phe Trp Cys Ala Pro Thr Leu Thr Tyr
                 325                 330                 335
Gln Ile Ala Phe Pro Lys Ser Pro Arg Val Arg Tyr Trp Lys Ile Ala
                 340                 345                 350
Asp Ile Leu Met Arg Met Thr Val Ser Ile Ala Leu Phe Thr Phe Leu
                 355                 360                 365
Leu Ala Gln Ile Val Gln Pro Ala Leu Glu Glu Leu Val Ser Asp Leu
                 370                 375                 380
Asp Glu Thr Asn Gly Ser Tyr Thr Ala Ile Phe Ala Glu Tyr Trp
385                 390                 395                 400
Leu Lys Leu Ser Ile Ala Asn Thr Tyr Leu Trp Leu Leu Met Phe Tyr
                 405                 410                 415
Thr Tyr Phe His Leu Tyr Leu Asn Leu Phe Ala Glu Leu Leu Arg Phe
                 420                 425                 430
```

```
Gly Asp Arg Val Phe Tyr Lys Asp Trp Trp Asn Ser Ser Glu Val Ser
            435                 440                 445

Ala Tyr Trp Arg Leu Trp Asn Met Pro Val His Tyr Trp Leu Ile Arg
    450                 455                 460

His Val Tyr Phe Pro Cys Val Arg Leu Lys Met Pro Lys Val Ala Ala
465                 470                 475                 480

Thr Phe Val Val Phe Leu Ser Ala Val Met His Glu Val Leu Val
                485                 490                 495

Ser Val Pro Phe His Ile Ile Arg Pro Trp Ser Phe Ile Gly Met Met
            500                 505                 510

Met Gln Ile Pro Leu Val Ala Phe Thr Lys Tyr Leu Tyr Arg Lys Phe
            515                 520                 525

Pro Gly Gly Ser Ile Gly Asn Val Leu Phe Trp Met Thr Phe Cys Val
            530                 535                 540

Ile Gly Gln Pro Met Ala Ile Leu Leu Tyr Tyr His Asp Ile Met Asn
545                 550                 555                 560

Arg Lys Gly Asn

<210> SEQ ID NO 4
<211> LENGTH: 756
<212> TYPE: PRT
<213> ORGANISM: Phaeodactylum tricornutum

<400> SEQUENCE: 4

Met Thr Thr Pro Val Ser Ser Glu Asp Thr Ala Thr Leu Gln Gln Lys
1               5                   10                  15

Ile Val Ala Leu Gln Ala Gln Leu Leu Ser Ala Thr His Ala Leu Glu
            20                  25                  30

Arg Met Lys Asn Glu Arg Gly Ala Ser Ala Asp His Ser Lys Ser
            35                  40                  45

Ala Gln Arg Asn Gly Ser Asp Pro Ser Ser Asp Pro Thr Gly Thr Ala
    50                  55                  60

Pro Val Ala Ala Pro Ala Lys Ser Gly Tyr Leu Phe Lys Glu Leu
65                  70                  75                  80

Asp Arg Ala Ile Gly Trp Gly Ile Lys Trp Ser Leu Arg Tyr Val
                85                  90                  95

Lys Leu Glu Ser Gly Arg Ile Ser Tyr Tyr Gly Ser His His Asp Thr
            100                 105                 110

Ser Pro Arg Tyr Glu Leu Gln Leu Arg Gly Cys Ala Val Arg Asp Asp
            115                 120                 125

Gly Trp Lys Arg Asn Pro Arg Phe Lys Thr Lys Arg Asn Glu Pro Pro
    130                 135                 140

Pro Leu Leu Asp Thr Thr Gly Ala Tyr Phe Phe Leu Phe Ser Val Tyr
145                 150                 155                 160

His Ala Pro Asp Ala Ala Glu Lys Glu Ile Asp Glu Thr Glu Ile Thr
                165                 170                 175

Pro Leu Leu Arg Phe Ser Thr Pro Ser Arg Ala Glu His Ser Ser Trp
            180                 185                 190

Ile Lys Leu Ala Ser Glu Ser Cys Ala Tyr Ser Glu Thr Asp Glu Phe
            195                 200                 205

Leu Ala Asp Glu Ala Ala Arg Ala Thr Gln Arg Ala Leu Gln His Gln
    210                 215                 220

Glu Ala Leu Gln Met Ala Gln Ala Met Pro Gly Ala Lys Pro Gly Thr
225                 230                 235                 240
```

```
Leu Pro Pro Leu Tyr Phe Ala Pro Thr Ile Lys Arg Ser Arg Ser Phe
                245                 250                 255

Ala Lys Leu Gln Glu His His Gly Asp Gly Met Pro Arg Val Asn Met
            260                 265                 270

Arg Arg Thr Lys Ser Arg Asp Phe Asn Ala Asp Lys Leu Asp Ala Arg
        275                 280                 285

Ser Thr Lys Gly Tyr Pro Pro Ser Lys Pro Met His Arg Ala Ala Glu
    290                 295                 300

Pro Ser Tyr Leu Ser Ala Asp Ala Pro Ile Gln Asn Tyr Arg Gly Phe
305                 310                 315                 320

Leu Asn Leu Gly Val Ile Ile Leu Ile Val Ser Asn Phe Arg Leu Ile
                325                 330                 335

Leu Gly Thr Ile Arg Ser Asn Gly Phe Val Leu Thr Thr Ala Val Lys
            340                 345                 350

His Tyr Lys Asn Leu Asn His Leu Lys Glu Asp Pro Trp Gln Glu Phe
        355                 360                 365

Pro Phe Val Ser Gly Phe Leu Leu Gln Leu Val Phe Val Ser Ile Ala
    370                 375                 380

Phe Gly Ile Glu Trp Met Leu Cys Arg Lys Tyr Phe Asn Glu Asn Phe
385                 390                 395                 400

Gly Met Ile Leu His His Phe Asn Ala His Ser Ala Leu Leu Ile Pro
                405                 410                 415

Leu Gly Ile Val Trp Asn Leu Ile Asp Arg Pro Ala Val Gly Ala Ile
            420                 425                 430

Leu Leu Leu His Ala Thr Ile Thr Trp Met Lys Leu Ile Ser Tyr Met
        435                 440                 445

Leu Ala Asn Glu Asp Tyr Arg Leu Ser Ser Arg Arg Val Gly Gly Asn
    450                 455                 460

Pro His Leu Ala Thr Leu Ala Leu Val Glu Asn Leu Asp Ser Asp Glu
465                 470                 475                 480

Ala Asn Ile Asn Tyr Pro Gln Asn Val Thr Leu Arg Asn Ile Phe Tyr
                485                 490                 495

Phe Trp Cys Ala Pro Thr Leu Thr Tyr Gln Ile Ala Phe Pro Lys Ser
            500                 505                 510

Pro Arg Val Arg Tyr Trp Lys Ile Ala Asp Ile Leu Met Arg Met Thr
        515                 520                 525

Val Ser Ile Ala Leu Phe Thr Phe Leu Leu Ala Gln Ile Val Gln Pro
    530                 535                 540

Ala Leu Glu Glu Leu Val Ser Asp Leu Asp Glu Thr Asn Gly Ser Tyr
545                 550                 555                 560

Thr Ala Ala Ile Phe Ala Glu Tyr Trp Leu Lys Leu Ser Ile Ala Asn
                565                 570                 575

Thr Tyr Leu Trp Leu Leu Met Phe Tyr Thr Tyr Phe His Leu Tyr Leu
            580                 585                 590

Asn Leu Phe Ala Glu Leu Leu Arg Phe Gly Asp Arg Val Phe Tyr Lys
        595                 600                 605

Asp Trp Trp Asn Ser Ser Glu Val Ser Ala Tyr Trp Arg Leu Trp Asn
    610                 615                 620

Met Pro Val His Tyr Trp Leu Ile Arg His Val Tyr Phe Pro Cys Val
625                 630                 635                 640

Arg Leu Lys Met Pro Lys Val Ala Ala Thr Phe Val Val Phe Phe Leu
                645                 650                 655
```

```
Ser Ala Val Met His Glu Val Leu Val Ser Val Pro Phe His Ile Ile
            660                 665                 670

Arg Pro Trp Ser Phe Ile Gly Met Met Gln Ile Pro Leu Val Ala
        675                 680                 685

Phe Thr Lys Tyr Leu Tyr Arg Lys Phe Pro Gly Gly Ser Phe Gly Asn
        690                 695                 700

Val Leu Phe Trp Met Thr Phe Cys Val Ile Gly Gln Pro Met Ala Ile
705                 710                 715                 720

Leu Leu Tyr Thr Val Asp Tyr Gln Tyr Gly Lys His His Ser Thr Asn
                725                 730                 735

Met Glu Ile Phe Asp Thr Asp Asp Cys Arg Phe Leu Trp Lys Asn Ser
            740                 745                 750

Cys Leu Ile Arg
        755

<210> SEQ ID NO 5
<211> LENGTH: 1692
<212> TYPE: DNA
<213> ORGANISM: Phaeodactylum tricornutum

<400> SEQUENCE: 5
gatgagaccg aaattacacc tttgttgcgt ttttcgacac cttcccgagc cgaacactcg      60
tcctggataa agcttgcctc ggaatcctgt gcttacagcg aaacggacga gtttctcgct     120
gacgaggccg ctcgcgcaac ccagcgtgct ttgcaacatc aagaagcgct gcaaatggcc     180
caagccatgc ctggggcaaa gccaggaacg ctgccgccac tctacttcgc gcctaccata     240
aagcgttcgc gttcctttgc taagctacaa gaacatcatg gagatgggat gcctcgggta     300
aatatgcgtc ggaccaaatc gcgagatttt aacgcggata gttggatgc gcgaagtacc     360 aagggctatc ccccttccaa gccgatgcat cgtgcggcag agccctcata cctcagcgcg     420
gatgctccca ttcaaaacta ccgaggattt ctgaatttag cgttattat tttgattgtt     480 tctaactttc ggctgatctt gggcacaatc cgtagcaacg gatttgtctt gacgactgca     540
gtgaagcact acaagaacct aaatcacctc aaggaagatc cctggcagga atttcctttt     600
gtatcaggat tcttctcca gctcgtcttt gtttcgattg cgtttgggat cgaatggatg     660
ttgtgccgga atacttcaa cgaaaacttc ggcatgatcc ttcatcactt caatgcccac     720
tcagccttgc tgatacccttt aggtattgtt tggaatctca tcgatagacc tgcggttggt     780
gcaattttgc ttttacacgc tacgataaca tggatgaaac tcatttctta catgttggcg     840
aacgaagatt accggctatc atcgcgtcgc gttgggggca acccacacct agctacgctc     900
gcattagtcg aaaatctaga ttcagatgag gcgaacatta actaccccca aaatgttact     960
ctccgcaaca tttttattt tggtgtgct ccgacgttga cttaccagat tgccttcccg    1020
aagtccccgc gagttcgcta ttggaaaatc gcggatatcc tgatgcgcat gacggtgtcc    1080
atcgcactat tcaccttttt gctggcacaa attgttcagc ctgcattgga agagctagtg    1140
agcgacctgg acgagaccaa tggatcctac accgcagcaa tatttgccga gtactggctg    1200
aaactttcga ttgctaacac atatttatgg cttcttatgt tctatacata tttccatttg    1260
tatctgaacc tcttttgctga gcttctgcga tttgagatc gtgtgttcta caagattgg    1320 tggaattcgt cggaagtatc tgcatattgg aggctttgga atatgcctgt tcactattgg    1380
ttgatccgac atgtgtattt ccctgcgtg cgactgaaga tgccgaaggt cgctgcaacc    1440
tttgtcgttt tttcctctc cgccgttatg cacgaggtgc ttgtcagcgt acccttcat    1500
```

-continued

```
attattcgtc cgtggtctttt tatcgggatg atgatgcaga ttcctttggt tgcgttcaca      1560
aagtatctct atcgcaaatt cccgggcggc tcgattggta atgtcctgtt ctggatgaca      1620
ttttgcgtca ttggccagcc aatggcgatt ctcttgtact atcatgatat tatgaatcga      1680
aaaggaaatt ga                                                          1692
```

<210> SEQ ID NO 6
<211> LENGTH: 31
<212> TYPE: DNA
<213> ORGANISM: Phaeodactylum tricornutum

<400> SEQUENCE: 6

```
cgcggtacca tggatgagac cgaaattaca c                                     31
```

<210> SEQ ID NO 7
<211> LENGTH: 63
<212> TYPE: DNA
<213> ORGANISM: Phaeodactylum tricornutum

<400> SEQUENCE: 7

```
ggcctcgagt caatttcctt ttcgattcat aatatcatga tagtacaaga gaatcgccat      60
tgg                                                                    63
```

<210> SEQ ID NO 8
<211> LENGTH: 37
<212> TYPE: DNA
<213> ORGANISM: Phaeodactylum tricornutum

<400> SEQUENCE: 8

```
ggatccacat aatgtcagga acattcaatg atataag                               37
```

<210> SEQ ID NO 9
<211> LENGTH: 36
<212> TYPE: DNA
<213> ORGANISM: Phaeodactylum tricornutum

<400> SEQUENCE: 9

```
tgcggccgct tacccaacta tcttcaattc tgcatc                                36
```

<210> SEQ ID NO 10
<211> LENGTH: 20
<212> TYPE: DNA
<213> ORGANISM: Phaeodactylum tricornutum

<400> SEQUENCE: 10

```
atgaccacgc ctgtatcttc                                                  20
```

<210> SEQ ID NO 11
<211> LENGTH: 20
<212> TYPE: DNA
<213> ORGANISM: Phaeodactylum tricornutum

<400> SEQUENCE: 11

```
tcaacgaatc aagcaggaat                                                  20
```

<210> SEQ ID NO 12
<211> LENGTH: 63
<212> TYPE: DNA
<213> ORGANISM: Phaeodactylum tricornutum

<400> SEQUENCE: 12

```
taagcccacg tctgctgcat tcagtgtgat ttccgtttcc atgacttaca ccgcatttcg      60
```

```
tag                                                                    63

<210> SEQ ID NO 13
<211> LENGTH: 19
<212> TYPE: PRT
<213> ORGANISM: Phaeodactylum tricornutum

<400> SEQUENCE: 13

Ala His Val Cys Cys Ile Gln Cys Asp Phe Arg Phe His Asp Leu His
1               5                   10                  15

Arg Ile Ser

<210> SEQ ID NO 14
<211> LENGTH: 10
<212> TYPE: PRT
<213> ORGANISM: Phaeodactylum tricornutum

<400> SEQUENCE: 14

Tyr His Asp Ile Met Asn Arg Lys Gly Asn
1               5                   10

<210> SEQ ID NO 15
<211> LENGTH: 5
<212> TYPE: PRT
<213> ORGANISM: Phaeodactylum tricornutum

<400> SEQUENCE: 15

Tyr Tyr His Asp Ile
1               5

<210> SEQ ID NO 16
<211> LENGTH: 5
<212> TYPE: PRT
<213> ORGANISM: Phaeodactylum tricornutum

<400> SEQUENCE: 16

Tyr Tyr His Asp Val
1               5

<210> SEQ ID NO 17
<211> LENGTH: 8
<212> TYPE: PRT
<213> ORGANISM: Phaeodactylum tricornutum
<220> FEATURE:
<221> NAME/KEY: misc_feature
<222> LOCATION: (7)..(8)
<223> OTHER INFORMATION: Xaa can be any naturally occurring amino acid

<400> SEQUENCE: 17

Asn Arg Gly Lys Lys Lys Xaa Xaa
1               5

<210> SEQ ID NO 18
<211> LENGTH: 1212
<212> TYPE: DNA
<213> ORGANISM: Phaeodactylum tricornutum

<400> SEQUENCE: 18
catcgtgcgg cagagccctc atacctcagc gcggatgctc ccattcaaaa ctaccgagga    60
tttctgaatt taggcgttat tattttgatt gtttctaact ttcggctgat cttgggcaca   120
atccgtagca acggatttgt cttgacgact gcagtgaagc actacaagaa cctaaatcac   180
ctcaaggaag atccctggca ggaatttcct tttgtatcag gatttcttct ccagctcgtc   240
```

```
tttgtttcga ttgcgtttgg gatcgaatgg atgttgtgcc ggaaatactt caacgaaaac      300
ttcggcatga tccttcatca cttcaatgcc cactcagcct tgctgatacc tttaggtatt      360
gtttggaatc tcatcgatag acctgcggtt ggtgcaattt tgcttttaca cgctacgata      420
acatggatga aactcatttc ttacatgttg gcgaacgaag attaccggct atcatcgcat      480
tcagatgagg cgaacattaa ctaccccaa aatgttactc tccgcaacat ttttttatttt      540 tggtgtgctc cgacgttgac ttaccagatt gccttcccga agtccccgcg agttcgctat      600
tggaaaatcg cggatatcct gatgcgcatg acggtgtcca tcgcactatt cacctttttg      660
ctggcacaaa ttgttcagcc tgcattggaa gagctagtga gcgacctgga cgagaccaat      720
ggatcctaca ccgcagcaat atttgccgag ctgaaacttt cgattgctaa cacatattta      780
tggcttctta tgttctatac atatttccat ttgtatctga acctctttgc tgagcttctg      840
cgatttggag atcgtgtgtt ctacaaagat tggtggaatt cgtcggaagt atctgcatat      900
tggaggcttt ggaatatgcc tgttcactat tggttgatcc gacatgtgta tttcccctgc      960
gtgcgactga agatgccgaa ggtcgctgca acctttgtcg ttttttttcct ctccgccgtt     1020 atgcacgagg tgcttgtcag cgtaccctttt catattattc gtccgtggtc ttttatcggg     1080
atgatgatgc agattccttt ggttgcgttc acaaagtatc tctatcgcaa attcccgggc     1140
ggctcgtttg gtaatgtcct gttctggatg acattttgcg tcattggcca gccaatggcg     1200
attctcttgt ac                                                         1212

<210> SEQ ID NO 19
<211> LENGTH: 1791
<212> TYPE: DNA
<213> ORGANISM: Phaeodactylum tricornutum

<400> SEQUENCE: 19
attgatgaga ccgaaattac accttttgttg cgttttttcga caccttcccg agccgaacac      60
tcgtcctgga taaagcttgc ctcggaatcc tgtgcttaca gcgaaacgga cgagtttctc      120
gctgacgagg ccgctcgcgc aacccagcgt gctttgcaac atcaagaagc gctgcaaatg      180
gcccaagcca tgcctggggc aaagccagga acgctgccgc cactctactt cgcgcctacc      240
ataaagcgtt cgcgttcctt tgctaagcta caagaacatc atggagatgg gatgcctcgg      300
gtaaatatgc gtcggaccaa atcgcgagat tttaacgcgg ataagttgga tgcgcgaagt      360
accaagggct atccccttc caagccgagt acgtatttct cttgaattgc acaacagctc      420 gaattttca ctcatacgtg tctgtaaatt tagtgcatcg tgcggcagag ccctcatacc      480
tcagcgcgga tgctcccatt caaaactacc gaggatttct gaatttaggc gttattattt      540
tgattgtttc taactttcgg ctgatcttgg gcacaatccg tagcaacgga tttgtcttga      600
cgactgcagt gaagcactac aagaacctaa atcacctcaa ggaagatccc tggcaggaat      660
ttccttttgt atcaggattt cttctccagc tcgtctttgt ttcgattgcg tttgggatcg      720
aatggatgtt gtgccggaaa tacttcaacg aaaacttcgg catgatcctt catcacttca      780
atgcccactc agccttgctg ataccttag gtattgtttg gaatctcatc gatagacctg      840
cggttggtgc aattttgctt ttacacgcta cgataacatg gatgaaactc atttcttaca      900
tgttggcgaa cgaagattac cggctatcat cgcgtcgcgt tgggggcaac ccacacctag      960
ctacgctcgc attagtcgaa aatctagatt cagatgaggc gaacattaac tacccccaaa     1020
atgttactct ccgcaacatt ttttatttttt ggtgtgctcc gacgttgact taccagattg     1080
```

```
ccttcccgaa gtccccgcga gttcgctatt ggaaaatcgc ggatatcctg atgcgcatga    1140
cggtgtccat cgcactattc accttttttgc tggcacaaat tgttcagcct gcattggaag    1200
agctagtgag cgacctggac gagaccaatg gatcctacac cgcagcaata tttgccgagt    1260
actggtaagc ccacgtctgc tgcattcagt gtgatttccg tttccatgac ttacaccgca    1320
tttcgtaggc tgaaactttc gattgctaac acatatttat ggcttcttat gttctataca    1380
tatttccatt tgtatctgaa cctctttgct gagcttctgc gatttggaga tcgtgtgttc    1440
tacaaagatt ggtggaattc gtcggaagta tctgcatatt ggaggctttg aatatgcct     1500 gttcactatt ggttgatccg acatgtgtat ttccctgcg tgcgactgaa gatgccgaag     1560
gtcgctgcaa cctttgtcgt tttttcctc tccgccgtta tgcacgaggt gcttgtcagc     1620 gtacccttc atattattcg tccgtggtct tttatcggga tgatgatgca gattcctttg      1680
gttgcgttca caaagtatct ctatcgcaaa ttcccgggcg gctcgtttgg taatgtcctg     1740
ttctggatga cattttgcgt cattggccag ccaatggcga ttctcttgta c             1791

<210> SEQ ID NO 20
<211> LENGTH: 1759
<212> TYPE: DNA
<213> ORGANISM: Phaeodactylum tricornutum

<400> SEQUENCE: 20
attgatgaga ccgaaattac acctttgttg cgttttttcga caccttcccg agccgaacac      60
tcgtcctgga taaagcttgc ctcggaatcc tgtgcttaca gcgaaacgga cgagtttctc     120
gctgacgagg ccgctcgcgc aacccagcgt gctttgcaac atcaagaagc gctgcaaatg     180
gcccaagcca tgcctggggc aaagccagga acgctgccgc cactctactt cgcgcctacc     240
ataaagcgtt cgcgttcctt tgctaagcta caagaacatc atggagatgg gatgcctcgg     300
gtaaatatgc gtcggaccaa atcgcgagat tttaacgcgg ataagttgga tgcgcgaagt     360
accaagggct atccccccttc caagccgatg catcgtgcgg cagagccctc ataccctcagc    420 gcggatgctc ccattcaaaa ctaccgagga tttctgaatt taggcgttat tattttgatt     480
gtttctaact ttcggctgat cttgggcaca atccgtagca acggatttgt cttgacgact     540
gcagtgaagc actacaagaa cctaaatcac ctcaaggaag atccctggca ggaatttcct     600
tttgtatcag gatttcttct ccagctcgtc tttgtttcga ttgcgtttgg gatcgaatgg     660
atgttgtgcc ggaaatactt caacgaaaac ttcggcatga tccttcatca cttcaatgcc     720
cactcagcct tgctgatacc tttaggtatt gtttggaatc tcatcgatag acctgcggtt     780
ggtgcaattt tgcttttaca cgctacgata acatggatga aactcatttc ttacatgttg     840
gcgaacgaag attaccggct atcatcgcgt cgcgttgggg gcaacccaca cctagctacg     900
ctcgcattag tcgaaaatct agattcagat gaggcgaaca ttaactaccc ccaaaatgtt     960
actctccgca acatttttta ttttttggtgt gctccgacgt tgacttacca gattgccttc    1020
ccgaagtccc cgcgagttcg ctattggaaa atcgcggata tcctgatgcg catgacggtg    1080
tccatcgcac tattcaccct ttttgctggca caaattgttc agcctgcatt ggaagagcta    1140
gtgagcgacc tggacgagac caatggatcc tacaccgcag caatatttgc cgagtactgg    1200
taagcccacg tctgctgcat tcagtgtgat ttccgtttcc atgacttaca ccgcatttcg    1260
taggctgaaa ctttcgattg ctaacacata tttatggctt cttatgttct atacatattt    1320
ccatttgtat ctgaacctct ttgctgagct tctgcgattt ggagatcgtg tgttctacaa    1380
agattggtgg aattcgtcgg aagtatctgc atattggagg ctttggaata tgcctgttca    1440
```

```
ctattggttg atccgacatg tgtatttccc ctgcgtgcga ctgaagatgc cgaaggtcgc    1500
tgcaaccttt gtcgttttttt tcctctccgc cgttatgcac gaggtgcttg tcagcgtacc   1560
ctttcatatt attcgtccgt ggtcttttat cgggatgatg atgcagattc ctttggttgc    1620
gttcacaaag tatctctatc gcaaattccc gggcggctcg attggtaatg tcctgttctg    1680
gatgacattt tgcgtcattg gccagccaat ggcgattctc ttgtactatc atgatattat    1740
gaatcgaaaa ggaaattga                                                  1759

<210> SEQ ID NO 21
<211> LENGTH: 1695
<212> TYPE: DNA
<213> ORGANISM: Phaeodactylum tricornutum

<400> SEQUENCE: 21
attgatgaga ccgaaattac acctttgttg cgttttttcga caccttcccg agccgaacac    60
tcgtcctgga taaagcttgc ctcggaatcc tgtgcttaca gcgaaacgga cgagtttctc   120
gctgacgagg ccgctcgcgc aacccagcgt gctttgcaac atcaagaagc gctgcaaatg   180
gcccaagcca tgcctggggc aaagccagga acgctgccgc cactctactt cgcgcctacc   240
ataaagcgtt cgcgttcctt tgctaagcta caagaacatc atggagatgg gatgcctcgg   300
gtaaatatgc gtcggaccaa atcgcgagat tttaacgcgg ataagttgga tgcgcgaagt   360
accaagggct atccccttc caagccgatg catcgtgcgg cagagccctc ataccctcagc   420 gcggatgctc ccattcaaaa ctaccgagga tttctgaatt taggcgttat tatttttgatt   480 gtttctaact ttcggctgat cttgggcaca atccgtagca acggatttgt cttgacgact   540
gcagtgaagc actacaagaa cctaaatcac ctcaaggaag atccctggca ggaatttcct   600
tttgtatcag gatttcttct ccagctcgtc tttgtttcga ttgcgtttgg gatcgaatgg   660
atgttgtgcc ggaaatactt caacgaaaac ttcggcatga tccttcatca cttcaatgcc   720
cactcagcct tgctgatacc tttaggtatt gtttggaatc tcatcgatag acctgcggtt   780
ggtgcaattt tgcttttaca cgctacgata acatggatga aactcatttc ttacatgttg   840
gcgaacgaag attaccggct atcatcgcgt cgcgttgggg gcaacccaca cctagctacg   900
ctcgcattag tcgaaaatct agattcagat gaggcgaaca ttaactaccc ccaaaatgtt   960
actctccgca acatttttta ttttttggtgt gctccgacgt tgacttacca gattgccttc  1020
ccgaagtccc cgcgagttcg ctattggaaa atcgcggata tcctgatgcg catgacggtg  1080
tccatcgcac tattcacctt tttgctggca caaattgttc agcctgcatt ggaagagcta  1140
gtgagcgacc tggacgagac caatggatcc tacaccgcag caatatttgc cgagtactgg  1200
ctgaaacttt cgattgctaa cacatatttta tggcttctta tgttctatac atatttccat  1260
ttgtatctga acctctttgc tgagcttctg cgatttggag atcgtgtgtt ctacaaagat  1320
tggtggaatt cgtcggaagt atctgcatat tggaggcttt ggaatatgcc tgttcactat  1380
tggttgatcc gacatgtgta tttcccctgc gtgcgactga agatgccgaa ggtcgctgca  1440
acctttgtcg ttttttttcct ctccgccgtt atgcacgagg tgcttgtcag cgtacccttt  1500
catattattc gtccgtggtc ttttatcggg atgatgatgc agattccttt ggttgcgttc  1560
acaaagtatc tctatcgcaa attcccgggc ggctcgattg gtaatgtcct gttctggatg  1620
acattttgcg tcattggcca gccaatggcg attctcttgt actatcatga tattatgaat  1680
cgaaaaggaa attga                                                   1695
```

<210> SEQ ID NO 22
<211> LENGTH: 854
<212> TYPE: DNA
<213> ORGANISM: Phaeodactylum tricornutum

<400> SEQUENCE: 22

| | | | | | |
|---|---|---|---|---|---|
| attgatgaga | ccgaaattac | acctttgttg | cgttttttcga | caccttcccg | agccgaacac | 60 |
| tcgtcctgga | taaagcttgc | ctcggaatcc | tgtgcttaca | gcgaaacgga | cgagtttctc | 120 |
| gctgacgagg | ccgctcgcgc | aacccagcgt | gctttgcaac | atcaagaagc | gctgcaaatg | 180 |
| gcccaagcca | tgcctggggc | aaagccagga | acgctgccgc | cactctactt | cgcgcctacc | 240 |
| ataaagcgtt | cgcgttcctt | tgctaagcta | caagaacatc | atggagatgg | gatgcctcgg | 300 |
| gtaaatatgc | gtcggaccaa | atcgcgagat | tttaacgcgg | ataagttgga | tgcgcgaagt | 360 |
| accaatggct | atccccttc | caagccgatg | catcgtgcgg | cagagccctc | ataccctcagc | 420 |
| gcggatgctc | ccattcaaaa | ctaccgagga | tttctgaatt | taggcgttat | tattttgatt | 480 |
| gtttctaact | ttcggctgat | cttgggcaca | atccgtagca | acggatttgt | cttgacgact | 540 |
| gcagtgaagc | actacaagaa | cctaaatcac | ctcaaggaag | atccctggca | ggaatttcct | 600 |
| tttgtatcag | gatttcttct | ccagctcgtc | tttgtttcga | ttgcgtttgg | gatcgaatgg | 660 |
| atgttgtgcc | ggaaatactt | caacgaaaac | ttcggcatga | tccttcatca | cttcaatgcc | 720 |
| cactcagcct | tgctgatacc | tttaggtatt | gtttggaatc | tcatcgatag | acctgcggtt | 780 |
| ggtgccattt | tgcttttaca | cgctacgata | acatggatga | agctcatttc | ttacatgttg | 840 |
| gcgaacgaag | atta | | | | | 854 |

<210> SEQ ID NO 23
<211> LENGTH: 937
<212> TYPE: DNA
<213> ORGANISM: Phaeodactylum tricornutum
<220> FEATURE:
<221> NAME/KEY: misc_feature
<222> LOCATION: (756)..(756)
<223> OTHER INFORMATION: n is a, c, g, or t

<400> SEQUENCE: 23

| | | | | | |
|---|---|---|---|---|---|
| ggcaaagcca | ggtacgctgc | cgccactcta | cttcgcgcct | accataaagc | gttcgcgttc | 60 |
| ctttgctaag | ctacaagaac | atcatggaga | tgggatgcct | cgggtaaata | tgcgtcggac | 120 |
| caaatcgcga | gattttaacg | cggataagtt | ggatgcgcga | agtaccaatg | gctatccccc | 180 |
| ttccaagccg | atgcatcgtg | cggcagagcc | tcatacctc | agcgcggatg | ctcccattca | 240 |
| aaactaccga | ggatttctga | atttaggcgt | tattattttg | attgtttcta | actttcggct | 300 |
| gatcttgggc | acaatccgta | gcaacggatt | tgtcttgacg | actgcagtga | agcactacaa | 360 |
| gaacctaaat | cacctcaagg | aagatccctg | gcaggaattt | cctttgtat | caggatttct | 420 |
| tctccagctc | gtctttgttt | cgattgcgtt | tgggatcgaa | tggatgttgt | gccggaaata | 480 |
| cttcaacgaa | aacttcggca | tgatccttca | tcacttcaat | gcccactcag | ccttgctgat | 540 |
| acctttaggt | attgtttgga | atctcatcga | tagacctgcg | gttggtgcaa | ttttgctttt | 600 |
| acacgctacg | ataacatgga | tgaagctcat | ttcttacatg | ttggcgaacg | aagattaccg | 660 |
| gctatcatcg | cgtcgcgttg | ggggcaaccc | acacctagct | acgctcgcat | tagtcgaaaa | 720 |
| tctagattca | gatgaggcga | acattaacta | ccccnaaat | gttactctcc | gcaacatttt | 780 |
| ttatttttgg | tgtgctccga | cgttgactta | ccagattgcc | ttcccgaagt | ccccgcgagt | 840 |
| tcgctaatgg | aaaatcgcgg | atatcctgga | tggcatgacg | gtgtccatcg | cactattcac | 900 | cttttttgcgg gcacaaattg ttcaccctgc cttggaa					937

<210> SEQ ID NO 24
<211> LENGTH: 990
<212> TYPE: DNA
<213> ORGANISM: Phaeodactylum tricornutum

<400> SEQUENCE: 24

| | | | | |
|---|---|---|---|---|
| ttcaacgaaa | ttttcggcat | gatccttcat | cacttcaatg | cccactcagc cttgctgata | 60 |
| cctttaggta | ttgtttggaa | tctcatcgat | agacctgcgg | ttggtgcaat tttgctttta | 120 |
| cacgctacga | taacatggat | gaagctcatt | tcttacatgt | tggcgaacga agattaccgg | 180 |
| ctatcatcgc | gtcgcgttgg | gggcaaccca | cacctagcta | cgctcgcatt agtcgaaaat | 240 |
| ctagattcag | atgaggcgaa | cattaactac | ccccaaaatg | ttactctccg caacattttt | 300 |
| tatttttggt | gtgctccgac | gttgacttac | cagattgcct | tccagaagtc cccgcgagtt | 360 |
| cgctattgga | aaatcgcgga | tatcctgatg | cgcatgacgg | tgtccatcgc actattcacc | 420 |
| tttttgctgg | cacaaattgt | tcagcctgca | ttggaagagc | tagtgagcga cctggacgag | 480 |
| accaatggat | cctacaccgc | agcaatattt | gccgagtact | ggctgaaaact ttcgattgct | 540 |
| aacacatatt | tatggcttct | tatgttctat | acatatttcc | atttgtatct gaacctcttt | 600 |
| gctgagcttc | tgcgatttgg | agatcgtgtg | ttctacaaag | attggtggaa ttcgtcggaa | 660 |
| gtatctgcat | aattggaggc | tttggaatat | gcctgttcac | tattggttga tccgacatgt | 720 |
| gtatttcccc | tgcgggcgac | tgaagatgcc | gaaggtcgct | gcaacctttg tcgttttttt | 780 |
| tctctccgcc | gttatgcacg | aggtgcttgt | cagcgtaccc | tttcaaatta tccgccgtgg | 840 |
| tctttaaccg | gaagatgatc | gaaattcctt | tggttgtttc | acaaagtatc tctaacccaa | 900 |
| attccggggc | ggctcgtttg | gaatggtccc | gttcgggaaa | atattttgct cctttggcca | 960 |
| aaccaatggc | atttccctgg | gtacacagtt | | | 990 |

<210> SEQ ID NO 25
<211> LENGTH: 564
<212> TYPE: PRT
<213> ORGANISM: Phaeodactylum tricornutum

<400> SEQUENCE: 25

Met Asp Glu Thr Glu Ile Thr Pro Leu Leu Arg Phe Ser Thr Pro Ser
1               5                   10                  15

Arg Ala Glu His Ser Ser Trp Ile Lys Leu Ala Ser Glu Ser Cys Ala
            20                  25                  30

Tyr Ser Glu Thr Asp Glu Phe Leu Ala Asp Glu Ala Ala Arg Ala Thr
        35                  40                  45

Gln Arg Ala Leu Gln His Gln Glu Ala Leu Gln Met Ala Gln Ala Met
    50                  55                  60

Pro Gly Ala Lys Pro Gly Thr Leu Pro Pro Leu Tyr Phe Ala Pro Thr
65                  70                  75                  80

Ile Lys Arg Ser Arg Ser Phe Ala Lys Leu Gln Glu His His Gly Asp
                85                  90                  95

Gly Met Pro Arg Val Asn Met Arg Thr Lys Ser Arg Asp Phe Asn
            100                 105                 110

Ala Asp Lys Leu Asp Ala Arg Ser Thr Lys Gly Tyr Pro Pro Ser Lys
        115                 120                 125

Pro Met His Arg Ala Ala Glu Pro Ser Tyr Leu Ser Ala Asp Ala Pro
    130                 135                 140

```
Ile Gln Asn Tyr Arg Gly Phe Leu Asn Leu Gly Val Ile Ile Leu Ile
145                 150                 155                 160

Val Ser Asn Phe Arg Leu Ile Leu Gly Thr Ile Arg Ser Asn Gly Phe
            165                 170                 175

Val Leu Thr Thr Ala Val Lys His Tyr Lys Asn Leu Asn His Leu Lys
        180                 185                 190

Glu Asp Pro Trp Gln Glu Phe Pro Phe Val Ser Gly Phe Leu Leu Gln
    195                 200                 205

Leu Val Phe Val Ser Ile Ala Phe Gly Ile Glu Trp Met Leu Cys Arg
210                 215                 220

Lys Tyr Phe Asn Glu Asn Phe Gly Met Ile Leu His His Phe Asn Ala
225                 230                 235                 240

His Ser Ala Leu Leu Ile Pro Leu Gly Ile Val Trp Asn Leu Ile Asp
            245                 250                 255

Arg Pro Ala Val Gly Ala Ile Leu Leu Leu His Ala Thr Ile Thr Trp
        260                 265                 270

Met Lys Leu Ile Ser Tyr Met Leu Ala Asn Glu Asp Tyr Arg Leu Ser
    275                 280                 285

Ser Arg Arg Val Gly Gly Asn Pro His Leu Ala Thr Leu Ala Leu Val
290                 295                 300

Glu Asn Leu Asp Ser Asp Glu Ala Asn Ile Asn Tyr Pro Gln Asn Val
305                 310                 315                 320

Thr Leu Arg Asn Ile Phe Tyr Phe Trp Cys Ala Pro Thr Leu Thr Tyr
            325                 330                 335

Gln Ile Ala Phe Pro Lys Ser Pro Arg Val Arg Tyr Trp Lys Ile Ala
        340                 345                 350

Asp Ile Leu Met Arg Met Thr Val Ser Ile Ala Leu Phe Thr Phe Leu
    355                 360                 365

Leu Ala Gln Ile Val Gln Pro Ala Leu Glu Glu Leu Val Ser Asp Leu
370                 375                 380

Asp Glu Thr Asn Gly Ser Tyr Thr Ala Ala Ile Phe Ala Glu Tyr Trp
385                 390                 395                 400

Leu Lys Leu Ser Ile Ala Asn Thr Tyr Leu Trp Leu Leu Met Phe Tyr
            405                 410                 415

Thr Tyr Phe His Leu Tyr Leu Asn Leu Phe Ala Glu Leu Leu Arg Phe
        420                 425                 430

Gly Asp Arg Val Phe Tyr Lys Asp Trp Trp Asn Ser Ser Glu Val Ser
    435                 440                 445

Ala Tyr Trp Arg Leu Trp Asn Met Pro Val His Tyr Trp Leu Ile Arg
450                 455                 460

His Val Tyr Phe Pro Cys Val Arg Leu Lys Met Pro Lys Val Ala Ala
465                 470                 475                 480

Thr Phe Val Val Phe Phe Leu Ser Ala Val Met His Glu Val Leu Val
            485                 490                 495

Ser Val Pro Phe His Ile Ile Arg Pro Trp Ser Phe Ile Gly Met Met
        500                 505                 510

Met Gln Ile Pro Leu Val Ala Phe Thr Lys Tyr Leu Tyr Arg Lys Phe
    515                 520                 525

Pro Gly Gly Ser Ile Gly Asn Val Leu Phe Trp Met Thr Phe Cys Val
530                 535                 540

Ile Gly Gln Pro Met Ala Ile Leu Leu Tyr Tyr His Asp Ile Met Asn
545                 550                 555                 560
```

Arg Lys Gly Asn

<210> SEQ ID NO 26
<211> LENGTH: 564
<212> TYPE: PRT
<213> ORGANISM: diacylglycerol acyltransferase

<400> SEQUENCE: 26

```
Met Asp Glu Thr Glu Ile Thr Pro Leu Leu Arg Phe Ser Thr Pro Ser
1               5                   10                  15

Arg Ala Glu His Ser Ser Trp Ile Lys Leu Ala Ser Glu Ser Cys Ala
            20                  25                  30

Tyr Ser Glu Thr Asp Glu Phe Leu Ala Asp Glu Ala Ala Arg Ala Thr
        35                  40                  45

Gln Arg Ala Leu Gln His Gln Glu Ala Leu Gln Met Ala Gln Ala Met
    50                  55                  60

Pro Gly Ala Lys Pro Gly Thr Leu Pro Pro Leu Tyr Phe Ala Pro Thr
65                  70                  75                  80

Ile Lys Arg Ser Arg Ser Phe Ala Lys Leu Gln Glu His His Gly Asp
                85                  90                  95

Gly Met Pro Arg Val Asn Met Arg Arg Thr Lys Ser Arg Asp Phe Asn
            100                 105                 110

Ala Asp Lys Leu Asp Ala Arg Ser Thr Lys Gly Tyr Pro Pro Ser Lys
        115                 120                 125

Pro Met His Arg Ala Ala Glu Pro Ser Tyr Leu Ser Ala Asp Ala Pro
    130                 135                 140

Ile Gln Asn Tyr Arg Gly Phe Leu Asn Leu Gly Val Ile Ile Leu Ile
145                 150                 155                 160

Val Ser Asn Phe Arg Leu Ile Leu Gly Thr Ile Arg Ser Asn Gly Phe
                165                 170                 175

Val Leu Thr Thr Ala Val Lys His Tyr Lys Asn Leu Asn His Leu Lys
            180                 185                 190

Glu Asp Pro Trp Gln Glu Phe Pro Phe Val Ser Gly Phe Leu Leu Gln
        195                 200                 205

Leu Val Phe Val Ser Ile Ala Phe Gly Ile Glu Trp Met Leu Cys Arg
    210                 215                 220

Lys Tyr Phe Asn Glu Asn Phe Gly Met Ile Leu His Phe Asn Ala
225                 230                 235                 240

His Ser Ala Leu Leu Ile Pro Leu Gly Ile Val Trp Asn Leu Ile Asp
                245                 250                 255

Arg Pro Ala Val Gly Ala Ile Leu Leu Leu His Ala Thr Ile Thr Trp
            260                 265                 270

Met Lys Leu Ile Ser Tyr Met Leu Ala Asn Glu Asp Tyr Arg Leu Ser
        275                 280                 285

Ser Arg Arg Val Gly Gly Asn Pro His Leu Ala Thr Leu Ala Leu Val
    290                 295                 300

Glu Asn Leu Asp Ser Asp Glu Ala Asn Ile Asn Tyr Pro Gln Asn Val
305                 310                 315                 320

Thr Leu Arg Asn Ile Phe Tyr Phe Trp Cys Ala Pro Thr Leu Thr Tyr
                325                 330                 335

Gln Ile Ala Phe Pro Lys Ser Pro Arg Val Arg Tyr Trp Lys Ile Ala
            340                 345                 350

Asp Ile Leu Met Arg Met Thr Val Ser Ile Ala Leu Phe Thr Phe Leu
        355                 360                 365
```

```
Leu Ala Gln Ile Val Gln Pro Ala Leu Glu Glu Leu Val Ser Asp Leu
        370                 375                 380

Asp Glu Thr Asn Gly Ser Tyr Thr Ala Ala Ile Phe Ala Glu Tyr Trp
385                 390                 395                 400

Leu Lys Leu Ser Ile Ala Asn Thr Tyr Leu Trp Leu Leu Met Phe Tyr
                405                 410                 415

Thr Tyr Phe His Leu Tyr Leu Asn Leu Phe Ala Glu Leu Leu Arg Phe
                420                 425                 430

Gly Asp Arg Val Phe Tyr Lys Asp Trp Trp Asn Ser Ser Glu Val Ser
                435                 440                 445

Ala Tyr Trp Arg Leu Trp Asn Met Pro Val His Tyr Trp Leu Ile Arg
450                 455                 460

His Val Tyr Phe Pro Cys Val Arg Leu Lys Met Pro Lys Val Ala Ala
465                 470                 475                 480

Thr Phe Val Val Phe Leu Ser Ala Val Met His Glu Val Leu Val
                485                 490                 495

Ser Val Pro Phe His Ile Ile Arg Pro Trp Ser Phe Ile Gly Met Met
                500                 505                 510

Met Gln Ile Pro Leu Val Ala Phe Thr Lys Tyr Leu Tyr Arg Lys Phe
                515                 520                 525

Pro Gly Gly Ser Ile Gly Asn Val Leu Phe Trp Met Thr Phe Cys Val
                530                 535                 540

Ile Gly Gln Pro Met Ala Ile Leu Leu Tyr Tyr His Asp Ile Met Asn
545                 550                 555                 560

Arg Lys Gly Asn

<210> SEQ ID NO 27
<211> LENGTH: 432
<212> TYPE: PRT
<213> ORGANISM: diacylglycerol acyltransferase

<400> SEQUENCE: 27

Glu Asp Pro Leu Gly Arg Ser Asp Ile Arg Ile Ser Tyr Pro Pro Ser
1               5                   10                  15

Lys Pro Met His Arg Gln Ser Asn Pro Ser Tyr Leu Ser Asp Gly Ser
                20                  25                  30

His Val Gln Asn Tyr Arg Gly Leu Phe Asn Leu Leu Leu Ile Leu
                35                  40                  45

Val Leu Ser Asn Phe Arg Leu Leu Leu Asp Thr Val Ala Gln His Gly
50                  55                  60

Phe Ile Leu Asp Lys Leu Ala Thr Leu Gln Gly Phe Ser Gln Ala Pro
65                  70                  75                  80

Leu Asp Phe Pro Phe Val Ser Gly Leu Leu Ile Val Gln Ala Phe Val
                85                  90                  95

Val Gly Ala Tyr Ala Ile Glu Lys Met Leu Ser Val Gly Leu Ile Gly
                100                 105                 110

Asn Gln Phe Gly Met Leu Leu His Val Ile Asn Ser Asn Ala Thr Leu
                115                 120                 125

Gly Val Val Met Ala Ile Val Trp Tyr Leu Ile Asp Gln Pro Phe Val
130                 135                 140

Gly Ala Gly Leu Ile Met Gln Ala Thr Ile Thr Trp Leu Lys Leu Ile
145                 150                 155                 160

Ser Tyr Ala His Ala Asn Tyr Asp Tyr Arg Thr Ser Pro Asp Thr Gln
                165                 170                 175
```

```
Lys Val Thr Val Ala Leu Val Lys Asp Leu Asp Asp Gly Gln Asn Val
                180                 185                 190

Ser Tyr Pro Gln Asn Val Thr Leu Lys Asp Ile Tyr Tyr Phe Trp Leu
            195                 200                 205

Ala Pro Thr Leu Thr Tyr Gln Ile Ala Phe Pro Arg Ser Pro Phe Ile
        210                 215                 220

Arg Trp Pro Lys Val Phe Ser Leu Thr Leu Gln Leu Phe Ile Ser Val
225                 230                 235                 240

Thr Leu Ala Val Phe Leu Cys Ala Gln Val Ala Pro Asn Leu Asp
                245                 250                 255

Ser Leu Val Lys Asn Leu Glu Ala Asn Lys Gly Glu Val Arg Thr Gln
            260                 265                 270

Gln Ile Phe Asp Tyr Leu Leu Lys Leu Ser Ile Thr Ser Thr Tyr Ile
        275                 280                 285

Trp Leu Leu Gly Phe Tyr Gly Phe His Cys Phe Met Asn Leu Ala
            290                 295                 300

Ala Glu Leu Leu Arg Phe Gly Asp Arg Val Phe Tyr Arg Asp Trp Trp
305                 310                 315                 320

Asn Ala Ser Glu Val Ser Ala Tyr Trp Arg Leu Trp Asn Met Pro Val
                325                 330                 335

His Tyr Trp Leu Val Arg His Val Tyr Phe Pro Cys Ile Arg Val Gly
            340                 345                 350

Met Ser Lys Lys Gly Ala Thr Phe Val Val Phe Phe Ser Ala Val
                355                 360                 365

Leu His Glu Val Leu Ile Ser Val Pro Cys His Met Ile Arg Ala Trp
370                 375                 380

Ser Phe Leu Ala Met Met Gly Gln Ile Pro Leu Ile Ile Leu Thr Lys
385                 390                 395                 400

Ile Ile Asp Lys Arg Val Pro Gly Ser Ser Ile Gly Asn Ile Ile Phe
                405                 410                 415

Trp Ile Ser Phe Cys Leu Val Gly Gln Pro Met Ala Met Leu Leu Tyr
                420                 425                 430

<210> SEQ ID NO 28
<211> LENGTH: 526
<212> TYPE: PRT
<213> ORGANISM: diacylglycerol acyltransferase

<400> SEQUENCE: 28

Met Thr Ile Pro Glu Thr Pro Asp Asn Ser Thr Asp Ala Thr Thr Ser
1               5                   10                  15

Gly Gly Ala Glu Ser Ser Ser Asp Leu Asn Leu Ser Leu Arg Arg Arg
            20                  25                  30

Arg Thr Ala Ser Asn Ser Asp Gly Ala Val Ala Glu Leu Ala Ser Lys
        35                  40                  45

Ile Asp Glu Leu Glu Ser Asp Ala Gly Gly Gln Val Ile Lys Asp
50                  55                  60

Pro Gly Ala Glu Met Asp Ser Gly Thr Leu Lys Ser Asn Gly Lys Asp
65                  70                  75                  80

Cys Gly Thr Val Lys Asp Arg Ile Glu Asn Arg Glu Asn Arg Gly Gly
                85                  90                  95

Ser Asp Val Lys Phe Thr Tyr Arg Pro Ser Val Pro Ala His Arg Ala
            100                 105                 110

Leu Lys Glu Ser Pro Leu Ser Ser Asp Asn Ile Phe Lys Gln Ser His
        115                 120                 125
```

```
Ala Gly Leu Phe Asn Leu Cys Ile Val Val Leu Val Ala Val Asn Ser
        130                 135                 140

Arg Leu Ile Ile Glu Asn Ile Met Lys Tyr Gly Trp Leu Ile Lys Thr
145                 150                 155                 160

Gly Phe Trp Phe Ser Ser Arg Ser Leu Arg Asp Trp Pro Leu Leu Met
                165                 170                 175

Cys Cys Leu Thr Leu Pro Ile Phe Ser Leu Ala Ala Tyr Leu Val Glu
                180                 185                 190

Lys Leu Ala Cys Arg Lys Tyr Ile Ser Ala Pro Thr Val Val Phe Leu
                195                 200                 205

His Ile Leu Phe Ser Ser Thr Ala Val Leu Tyr Pro Val Ser Val Ile
        210                 215                 220

Leu Ser Cys Glu Ser Ala Val Leu Ser Gly Val Ala Leu Met Leu Phe
225                 230                 235                 240

Ala Cys Ile Val Trp Leu Lys Leu Val Ser Tyr Ala His Thr Asn Phe
                245                 250                 255

Asp Met Arg Ala Ile Ala Asn Ser Val Asp Lys Gly Asp Ala Leu Ser
                260                 265                 270

Asn Ala Ser Ser Ala Glu Ser Ser His Asp Val Ser Phe Lys Ser Leu
                275                 280                 285

Val Tyr Phe Met Val Ala Pro Thr Leu Cys Tyr Gln Pro Ser Tyr Pro
        290                 295                 300

Arg Thr Ala Ser Ile Arg Lys Gly Trp Val Val Arg Gln Phe Val Lys
305                 310                 315                 320

Leu Ile Ile Phe Thr Gly Phe Met Gly Phe Ile Ile Glu Gln Tyr Ile
                325                 330                 335

Asn Pro Ile Val Gln Asn Ser Gln His Pro Leu Lys Gly Asp Leu Leu
                340                 345                 350

Tyr Ala Ile Glu Arg Val Leu Lys Leu Ser Val Pro Asn Leu Tyr Val
                355                 360                 365

Trp Leu Cys Met Phe Tyr Cys Phe Phe His Leu Trp Leu Asn Ile Leu
        370                 375                 380

Ala Glu Leu Leu Arg Phe Gly Asp Arg Glu Phe Tyr Lys Asp Trp Trp
385                 390                 395                 400

Asn Ala Arg Thr Val Glu Glu Tyr Trp Arg Met Trp Asn Met Pro Val
                405                 410                 415

His Lys Trp Met Val Arg His Ile Tyr Phe Pro Cys Leu Arg His Lys
                420                 425                 430

Ile Pro Arg Gly Val Ala Leu Ile Thr Phe Val Ser Ala Val
                435                 440                 445

Phe His Glu Leu Cys Ile Ala Val Pro Cys His Ile Phe Lys Leu Trp
        450                 455                 460

Ala Phe Ile Gly Ile Met Phe Gln Ile Pro Leu Val Gly Ile Thr Asn
465                 470                 475                 480

Tyr Leu Gln Asn Lys Phe Arg Ser Ser Met Val Gly Asn Met Ile Phe
                485                 490                 495

Trp Phe Ile Phe Cys Ile Leu Gly Gln Pro Met Cys Leu Leu Leu Tyr
                500                 505                 510

Tyr His Asp Leu Met Asn Arg Lys Gly Thr Thr Glu Ser Arg
        515                 520                 525

<210> SEQ ID NO 29
<211> LENGTH: 521
```

<212> TYPE: PRT
<213> ORGANISM: diacylglycerol acyltransferase

<400> SEQUENCE: 29

```
Met Thr Ile Leu Glu Thr Pro Glu Thr Leu Gly Val Ile Ser Ser Ser
 1               5                  10                  15

Ala Thr Ser Asp Leu Asn Leu Ser Leu Arg Arg Arg Arg Thr Ser Asn
                20                  25                  30

Asp Ser Asp Gly Ala Leu Ala Asp Leu Ala Ser Lys Phe Asp Asp Asp
            35                  40                  45

Asp Asp Val Arg Ser Glu Asp Ser Ala Glu Asn Ile Ile Glu Asp Pro
        50                  55                  60

Val Ala Ala Val Thr Glu Leu Ala Thr Ala Lys Ser Asn Gly Lys Asp
 65                  70                  75                  80

Cys Val Ala Asn Ser Asn Lys Asp Lys Ile Asp Ser His Gly Gly Ser
                85                  90                  95

Ser Asp Phe Lys Leu Ala Tyr Arg Pro Ser Val Pro Ala His Arg Ser
            100                 105                 110

Leu Lys Glu Ser Pro Leu Ser Ser Asp Leu Ile Phe Lys Gln Ser His
        115                 120                 125

Ala Gly Leu Phe Asn Leu Cys Ile Val Val Leu Val Ala Val Asn Ser
    130                 135                 140

Arg Leu Ile Ile Glu Asn Leu Met Lys Tyr Gly Trp Leu Ile Lys Thr
145                 150                 155                 160

Gly Phe Trp Phe Ser Ser Arg Ser Leu Arg Asp Trp Pro Leu Phe Met
                165                 170                 175

Cys Cys Leu Ser Leu Pro Val Phe Pro Leu Ala Ala Tyr Leu Val Glu
            180                 185                 190

Lys Ala Ala Tyr Arg Lys Tyr Ile Ser Pro Pro Ile Val Ile Phe Leu
        195                 200                 205

His Val Ile Ile Thr Ser Ala Ala Val Leu Tyr Pro Ala Ser Val Ile
    210                 215                 220

Leu Ser Cys Glu Ser Ala Phe Leu Ser Gly Val Thr Leu Met Glu Leu
225                 230                 235                 240

Ala Cys Met Val Trp Leu Lys Leu Val Ser Tyr Ala His Thr Asn Tyr
                245                 250                 255

Asp Met Arg Ala Ile Ala Asp Thr Ile His Lys Glu Asp Ala Ser Asn
            260                 265                 270

Ser Ser Ser Thr Glu Tyr Cys His Asp Val Ser Phe Lys Thr Leu Ala
        275                 280                 285

Tyr Phe Met Val Ala Pro Thr Leu Cys Tyr Gln Pro Ser Tyr Pro Arg
    290                 295                 300

Thr Ala Phe Ile Arg Lys Gly Trp Val Phe Arg Gln Phe Val Lys Leu
305                 310                 315                 320

Ile Ile Phe Thr Gly Phe Met Gly Phe Ile Ile Glu Gln Tyr Ile Asn
                325                 330                 335

Pro Ile Val Gln Asn Ser Gln His Pro Leu Lys Gly Asp Leu Leu Tyr
            340                 345                 350

Ala Ile Glu Arg Val Leu Lys Leu Ser Val Pro Asn Leu Tyr Val Trp
        355                 360                 365

Leu Cys Leu Phe Tyr Cys Phe Phe His Leu Trp Leu Asn Ile Val Ala
    370                 375                 380

Glu Leu Leu Arg Phe Gly Asp Arg Glu Phe Tyr Lys Asp Trp Trp Asn
385                 390                 395                 400
```

```
Ala Lys Thr Val Glu Glu Tyr Trp Arg Met Trp Asn Met Pro Val His
            405                 410                 415

Lys Trp Met Val Arg His Ile Tyr Phe Pro Cys Leu Arg Arg Lys Ile
            420                 425                 430

Pro Arg Gly Val Ala Ile Val Ile Ala Phe Phe Val Ser Ala Val Phe
            435                 440                 445

His Glu Leu Cys Ile Ala Val Pro Cys His Met Phe Lys Leu Trp Ala
            450                 455                 460

Phe Phe Gly Ile Met Phe Gln Ile Pro Leu Val Val Ile Thr Asn Tyr
465                 470                 475                 480

Phe Gln Arg Lys Phe Arg Ser Ser Met Val Gly Asn Met Ile Phe Trp
            485                 490                 495

Phe Phe Phe Cys Ile Leu Gly Gln Pro Met Cys Val Leu Leu Tyr Tyr
            500                 505                 510

His Asp Leu Met Asn Arg Asp Gly Asn
            515                 520

<210> SEQ ID NO 30
<211> LENGTH: 532
<212> TYPE: PRT
<213> ORGANISM: diacylglycerol acyltransferase

<400> SEQUENCE: 30

Met Thr Ile Pro Glu Leu Pro Glu Ser Leu Glu Thr Thr Thr Leu Asn
1               5                   10                  15

Ser His His Ser Arg Ala Ala Ser Thr Val Arg Arg Ser Ile Asp
            20                  25                  30

Val Ala Val Leu Glu Ser Asp Ser Asn Ser Leu Glu Ala Val Asn Asp
            35                  40                  45

Ser Asp Ser Asp Val Asn Asn Thr Asn Glu Met Gly Asn Leu Arg Gly
        50                  55                  60

Gly Val Val Glu Ser Ala Leu Glu Glu Pro Ser Glu Leu Gly Thr Glu
65                  70                  75                  80

Gly Leu Arg Asn Gly Lys Glu Glu Asn Glu His Val Arg Thr Gly Glu
            85                  90                  95

Ser Asn Gln Glu Met Glu Val Leu Ala Ser Ala Lys Phe Ala His Arg
            100                 105                 110

Pro Ser Ala Pro Val His Arg Arg Ile Lys Glu Ser Pro Leu Ser Ser
            115                 120                 125

Asp Ala Ile Phe Lys Gln Ser His Ala Gly Leu Phe Asn Leu Cys Ile
        130                 135                 140

Val Val Leu Val Ala Val Asn Ser Arg Leu Ile Ile Glu Asn Leu Met
145                 150                 155                 160

Lys Tyr Gly Trp Leu Ile Asn Ser Gly Phe Trp Phe Ser Ser Thr Ser
            165                 170                 175

Leu Lys Asp Trp Pro Leu Leu Met Cys Cys Leu Ser Leu Pro Ile Phe
            180                 185                 190

Pro Leu Ala Ala Phe Phe Val Glu Lys Leu Val Leu Lys Tyr Ile
            195                 200                 205

Ser Glu Cys Val Ala Val Phe Leu His Ile Leu Ile Thr Thr Ala Ala
            210                 215                 220

Ile Leu Tyr Pro Val Leu Val Ile Leu Arg Cys Asp Ser Ala Val Leu
225                 230                 235                 240

Ser Gly Val Thr Leu Met Leu Phe Ala Cys Ile Val Trp Leu Lys Leu
```

```
            245                 250                 255
Val Ser Tyr Ala His Ala Ser His Asp Met Arg Ala Leu Ala Lys Ser
            260                 265                 270

Leu Asp Lys Gly Glu Thr Leu Ser Gly Tyr Trp Asn Ser Asp Asp Ser
            275                 280                 285

Tyr Gly Ala Ser Phe Gln Ser Leu Ala Tyr Phe Met Val Ala Pro Thr
            290                 295                 300

Leu Cys Tyr Gln Pro Ser Tyr Pro Arg Thr Ser Cys Ile Arg Lys Gly
305                 310                 315                 320

Trp Val Val Arg Gln Leu Ile Lys Leu Ile Ile Phe Thr Gly Phe Met
                325                 330                 335

Gly Phe Ile Val Glu Gln Tyr Ile Asn Pro Ile Val Arg Asn Ser Gln
            340                 345                 350

His Pro Leu Lys Gly Asn Leu Leu Tyr Ala Ile Glu Arg Val Leu Lys
            355                 360                 365

Leu Ser Val Pro Asn Leu Tyr Val Trp Leu Cys Met Phe Tyr Cys Phe
            370                 375                 380

Phe His Leu Trp Leu Asn Ile Leu Ala Glu Leu Leu Cys Phe Gly Asp
385                 390                 395                 400

Arg Glu Phe Tyr Lys Asp Trp Trp Asn Ala Lys Thr Val Glu Glu Tyr
                405                 410                 415

Trp Arg Met Trp Asn Met Pro Val His Lys Trp Met Val Arg His Ile
            420                 425                 430

Tyr Phe Pro Cys Leu Arg Asn Gly Met Pro Arg Gly Gly Ala Ile Leu
            435                 440                 445

Ile Ala Phe Leu Ile Ser Ala Ile Phe His Glu Leu Cys Ile Ala Val
450                 455                 460

Pro Cys His Ile Phe Lys Phe Trp Ala Phe Ile Gly Ile Met Phe Gln
465                 470                 475                 480

Val Pro Leu Val Ile Leu Thr Asn Tyr Leu Gln Asp Lys Phe Gln Asn
                485                 490                 495

Ser Met Val Gly Asn Met Ile Phe Trp Cys Phe Phe Ser Ile Leu Gly
            500                 505                 510

Gln Pro Met Cys Leu Leu Leu Tyr Tyr His Asp Leu Met Asn Arg Lys
            515                 520                 525

Ala Ser Ala Lys
            530

<210> SEQ ID NO 31
<211> LENGTH: 520
<212> TYPE: PRT
<213> ORGANISM: diacylglycerol acyltransferase

<400> SEQUENCE: 31

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Arg Lys Ser Arg
            20                  25                  30

Ser Asp Ser Ser Asn Gly Leu Leu Leu Ser Gly Ser Asp Asn Asn Ser
            35                  40                  45

Pro Ser Asp Asp Val Gly Ala Pro Ala Asp Val Arg Asp Arg Ile Asp
            50                  55                  60

Ser Val Val Asn Asp Asp Ala Gln Gly Thr Ala Asn Leu Ala Gly Asp
65                  70                  75                  80
```

```
Asn Asn Gly Gly Gly Asp Asn Asn Gly Gly Gly Arg Gly Gly Gly Glu
                85                  90                  95
Gly Arg Gly Asn Ala Asp Ala Thr Phe Thr Tyr Arg Pro Ser Val Pro
            100                 105                 110
Ala His Arg Arg Ala Arg Glu Ser Pro Leu Ser Ser Asp Ala Ile Phe
        115                 120                 125
Lys Gln Ser His Ala Gly Leu Phe Asn Leu Cys Val Val Leu Ile
    130                 135                 140
Ala Val Asn Ser Arg Leu Ile Ile Glu Asn Leu Met Lys Tyr Gly Trp
145                 150                 155                 160
Leu Ile Arg Thr Asp Phe Trp Phe Ser Ser Arg Ser Leu Arg Asp Trp
                165                 170                 175
Pro Leu Phe Met Cys Cys Ile Ser Leu Ser Ile Phe Pro Leu Ala Ala
            180                 185                 190
Phe Thr Val Glu Lys Leu Val Leu Gln Lys Tyr Ile Ser Glu Pro Val
        195                 200                 205
Val Ile Phe Leu His Ile Ile Thr Met Thr Glu Val Leu Tyr Pro
    210                 215                 220
Val Tyr Val Thr Leu Arg Cys Asp Ser Ala Phe Leu Ser Gly Val Thr
225                 230                 235                 240
Leu Met Leu Leu Thr Cys Ile Val Trp Leu Lys Leu Val Ser Tyr Ala
                245                 250                 255
His Thr Ser Tyr Asp Ile Arg Ser Leu Ala Asn Ala Ala Asp Lys Ala
            260                 265                 270
Asn Pro Glu Val Ser Tyr Tyr Val Ser Leu Lys Ser Leu Ala Tyr Phe
        275                 280                 285
Met Val Ala Pro Thr Leu Cys Tyr Gln Pro Ser Tyr Pro Arg Ser Ala
    290                 295                 300
Cys Ile Arg Lys Gly Trp Val Ala Arg Gln Phe Ala Lys Leu Val Ile
305                 310                 315                 320
Phe Thr Gly Phe Met Gly Phe Ile Ile Glu Gln Tyr Ile Asn Pro Ile
                325                 330                 335
Val Arg Asn Ser Lys His Pro Leu Lys Gly Asp Leu Leu Tyr Ala Ile
            340                 345                 350
Glu Arg Val Leu Lys Leu Ser Val Pro Asn Leu Tyr Val Trp Leu Cys
        355                 360                 365
Met Phe Tyr Cys Phe Phe His Leu Trp Leu Asn Ile Leu Ala Glu Leu
    370                 375                 380
Leu Cys Phe Gly Asp Arg Glu Phe Tyr Lys Asp Trp Trp Asn Ala Lys
385                 390                 395                 400
Ser Val Gly Asp Tyr Trp Arg Met Trp Asn Met Pro Val His Lys Trp
                405                 410                 415
Met Val Arg His Ile Tyr Phe Pro Cys Leu Arg Ser Lys Ile Pro Lys
            420                 425                 430
Thr Leu Ala Ile Ile Ile Ala Phe Leu Val Ser Ala Val Phe His Glu
        435                 440                 445
Leu Cys Ile Ala Val Pro Cys Arg Leu Phe Lys Leu Trp Ala Phe Leu
    450                 455                 460
Gly Ile Met Phe Gln Val Pro Leu Val Phe Ile Thr Asn Tyr Leu Gln
465                 470                 475                 480
Glu Arg Phe Gly Ser Thr Val Gly Asn Met Ile Phe Trp Phe Ile Phe
                485                 490                 495
Cys Ile Phe Gly Gln Pro Met Cys Val Leu Leu Tyr Tyr His Asp Leu
```

```
                500             505             510
Met Asn Arg Lys Gly Ser Met Ser
            515             520

<210> SEQ ID NO 32
<211> LENGTH: 494
<212> TYPE: PRT
<213> ORGANISM: diacylglycerol acyltransferase

<400> SEQUENCE: 32

Met Ala Pro Pro Ser Met Pro Ala Ala Ser Asp Arg Ala Gly Pro
1               5                   10                  15

Gly Arg Asp Ala Gly Asp Ser Ser Leu Arg Leu Arg Arg Ala Pro
                20                  25                  30

Ser Ala Asp Ala Gly Asp Leu Ala Gly Asp Ser Ser Gly Gly Leu Arg
                35                  40                      45

Glu Asn Gly Glu Pro Gln Ser Pro Thr Asn Pro Pro Gln Glu Gln
        50                  55                  60

Gln Gln His Glu Met Leu Tyr Tyr Arg Ala Ser Ala Pro Ala His Arg
65              70                      75                  80

Arg Val Lys Glu Ser Pro Leu Ser Asp Ala Ile Phe Arg Gln Ser
                    85                  90                  95

His Ala Gly Leu Leu Asn Leu Cys Ile Val Val Leu Ile Ala Val Asn
                100                 105                 110

Ser Arg Leu Ile Ile Glu Asn Leu Met Lys Tyr Gly Leu Leu Ile Arg
            115                 120                 125

Ala Gly Phe Trp Phe Ser Ala Arg Ser Leu Gly Asp Trp Pro Leu Leu
            130                 135                 140

Met Cys Cys Leu Thr Leu Pro Val Phe Pro Leu Val Ala Leu Met Ala
145                 150                 155                 160

Glu Lys Leu Ile Thr Arg Lys Leu Ile Gly Glu His Val Val Ile Leu
                165                 170                 175

Leu His Ile Ile Ile Thr Thr Ser Ala Ile Val Tyr Pro Val Val Val
                180                 185                 190

Thr Leu Lys Cys Asp Ser Ala Val Leu Ser Gly Phe Val Leu Met Phe
                195                 200                 205

Leu Ala Ser Ile Met Trp Met Lys Leu Val Ser Tyr Ala His Thr Asn
210                 215                 220

Tyr Asp Ile Arg Val Leu Ser Lys Ser Thr Glu Lys Gly Ala Ala Tyr
225                 230                 235                 240

Gly Asn Tyr Val Asp Pro Glu Asn Met Lys Asp Pro Thr Phe Lys Ser
                245                 250                 255

Leu Val Tyr Phe Met Leu Ala Pro Thr Leu Cys Tyr Gln Pro Thr Tyr
                260                 265                 270

Pro Gln Thr Thr Cys Ile Arg Lys Gly Trp Val Thr Gln Gln Leu Ile
            275                 280                 285

Lys Cys Val Val Phe Thr Gly Leu Met Gly Phe Ile Ile Glu Gln Tyr
            290                 295                 300

Ile Asn Pro Ile Val Lys Asn Ser Lys His Pro Leu Lys Gly Asn Phe
305                 310                 315                 320

Leu Asn Ala Ile Glu Arg Val Leu Lys Leu Ser Val Pro Thr Leu Tyr
                325                 330                 335

Val Trp Leu Cys Met Phe Tyr Cys Phe Phe His Leu Trp Leu Asn Ile
                340                 345                 350
```

Val Ala Glu Leu Leu Cys Phe Gly Asp Arg Glu Phe Tyr Lys Asp Trp
355                 360                 365

Trp Asn Ala Lys Thr Val Glu Glu Tyr Trp Arg Met Trp Asn Met Pro
    370                 375                 380

Val His Lys Trp Ile Ile Arg His Ile Tyr Phe Pro Cys Ile Arg Lys
385                 390                 395                 400

Gly Phe Ser Arg Gly Val Ala Ile Leu Ile Ser Phe Leu Val Ser Ala
            405                 410                 415

Val Phe His Glu Ile Cys Ile Ala Val Pro Cys His Ile Phe Lys Phe
                420                 425                 430

Trp Ala Phe Ser Gly Ile Met Phe Gln Ile Pro Leu Val Phe Leu Thr
            435                 440                 445

Arg Tyr Leu His Ala Thr Phe Lys His Val Met Val Gly Asn Met Ile
                450                 455                 460

Phe Trp Phe Phe Phe Ser Ile Val Gly Gln Pro Met Cys Val Leu Leu
465                 470                 475                 480

Tyr Tyr His Asp Val Met Asn Arg Gln Ala Gln Ala Ser Arg
                485                 490

<210> SEQ ID NO 33
<211> LENGTH: 756
<212> TYPE: PRT
<213> ORGANISM: Phaeodactylum tricornutum

<400> SEQUENCE: 33

Met Thr Thr Pro Val Ser Ser Glu Asp Thr Ala Thr Leu Gln Gln Lys
1               5                   10                  15

Ile Val Ala Leu Gln Ala Gln Leu Leu Ser Ala Thr His Ala Leu Glu
            20                  25                  30

Arg Met Lys Asn Glu Arg Gly Ala Ser Ser Ala Asp His Ser Lys Ser
        35                  40                  45

Ala Gln Arg Asn Gly Ser Asp Pro Ser Ser Asp Pro Thr Gly Thr Ala
    50                  55                  60

Pro Val Ala Ala Pro Ala Lys Ser Gly Tyr Leu Phe Lys Glu Leu
65                  70                  75                  80

Asp Arg Ala Ile Gly Trp Gly Ile Lys Trp Ser Leu Arg Tyr Val
                85                  90                  95

Lys Leu Glu Ser Gly Arg Ile Ser Tyr Tyr Gly Ser His His Asp Thr
            100                 105                 110

Ser Pro Arg Tyr Glu Leu Gln Leu Arg Gly Cys Ala Val Arg Asp Asp
        115                 120                 125

Gly Trp Lys Arg Asn Pro Arg Phe Lys Thr Lys Arg Asn Glu Pro Pro
    130                 135                 140

Pro Leu Leu Asp Thr Thr Gly Ala Tyr Phe Phe Leu Phe Ser Val Tyr
145                 150                 155                 160

His Ala Pro Asp Ala Ala Glu Lys Glu Ile Asp Glu Thr Glu Ile Thr
                165                 170                 175

Pro Leu Leu Arg Phe Ser Thr Pro Ser Arg Ala Glu His Ser Ser Trp
            180                 185                 190

Ile Lys Leu Ala Ser Glu Ser Cys Ala Tyr Ser Glu Thr Asp Glu Phe
        195                 200                 205

Leu Ala Asp Glu Ala Ala Arg Ala Thr Gln Arg Ala Leu Gln His Gln
    210                 215                 220

Glu Ala Leu Gln Met Ala Gln Ala Met Pro Gly Ala Lys Pro Gly Thr
225                 230                 235                 240

-continued

Leu Pro Pro Leu Tyr Phe Ala Pro Thr Ile Lys Arg Ser Arg Ser Phe
            245                 250                 255

Ala Lys Leu Gln Glu His His Gly Asp Gly Met Pro Arg Val Asn Met
        260                 265                 270

Arg Arg Thr Lys Ser Arg Asp Phe Asn Ala Asp Lys Leu Asp Ala Arg
        275                 280                 285

Ser Thr Lys Gly Tyr Pro Pro Ser Lys Pro Met His Arg Ala Ala Glu
    290                 295                 300

Pro Ser Tyr Leu Ser Ala Asp Ala Pro Ile Gln Asn Tyr Arg Gly Phe
305                 310                 315                 320

Leu Asn Leu Gly Val Ile Ile Leu Ile Val Ser Asn Phe Arg Leu Ile
                325                 330                 335

Leu Gly Thr Ile Arg Ser Asn Gly Phe Val Leu Thr Thr Ala Val Lys
            340                 345                 350

His Tyr Lys Asn Leu Asn His Leu Lys Glu Asp Pro Trp Gln Glu Phe
        355                 360                 365

Pro Phe Val Ser Gly Phe Leu Leu Gln Leu Val Phe Val Ser Ile Ala
    370                 375                 380

Phe Gly Ile Glu Trp Met Leu Cys Arg Lys Tyr Phe Asn Glu Asn Phe
385                 390                 395                 400

Gly Met Ile Leu His His Phe Asn Ala His Ser Ala Leu Leu Ile Pro
                405                 410                 415

Leu Gly Ile Val Trp Asn Leu Ile Asp Arg Pro Ala Val Gly Ala Ile
            420                 425                 430

Leu Leu Leu His Ala Thr Ile Thr Trp Met Lys Leu Ile Ser Tyr Met
        435                 440                 445

Leu Ala Asn Glu Asp Tyr Arg Leu Ser Ser Arg Arg Val Gly Gly Asn
    450                 455                 460

Pro His Leu Ala Thr Leu Ala Leu Val Glu Asn Leu Asp Ser Asp Glu
465                 470                 475                 480

Ala Asn Ile Asn Tyr Pro Gln Asn Val Thr Leu Arg Asn Ile Phe Tyr
                485                 490                 495

Phe Trp Cys Ala Pro Thr Leu Thr Tyr Gln Ile Ala Phe Pro Lys Ser
            500                 505                 510

Pro Arg Val Arg Tyr Trp Lys Ile Ala Asp Ile Leu Met Arg Met Thr
        515                 520                 525

Val Ser Ile Ala Leu Phe Thr Phe Leu Leu Ala Gln Ile Val Gln Pro
    530                 535                 540

Ala Leu Glu Glu Leu Val Ser Asp Leu Asp Glu Thr Asn Gly Ser Tyr
545                 550                 555                 560

Thr Ala Ala Ile Phe Ala Glu Tyr Trp Leu Lys Leu Ser Ile Ala Asn
                565                 570                 575

Thr Tyr Leu Trp Leu Leu Met Phe Tyr Thr Tyr Phe His Leu Tyr Leu
            580                 585                 590

Asn Leu Phe Ala Glu Leu Leu Arg Phe Gly Asp Arg Val Phe Tyr Lys
        595                 600                 605

Asp Trp Trp Asn Ser Ser Glu Val Ser Ala Tyr Trp Arg Leu Trp Asn
    610                 615                 620

Met Pro Val His Tyr Trp Leu Ile Arg His Val Tyr Phe Pro Cys Val
625                 630                 635                 640

Arg Leu Lys Met Pro Lys Val Ala Ala Thr Phe Val Val Phe Phe Leu
                645                 650                 655

-continued

```
Ser Ala Val Met His Glu Val Leu Val Ser Val Pro Phe His Ile Ile
            660                 665                 670
Arg Pro Trp Ser Phe Ile Gly Met Met Met Gln Ile Pro Leu Val Ala
        675                 680                 685
Phe Thr Lys Tyr Leu Tyr Arg Lys Phe Pro Gly Gly Ser Phe Gly Asn
    690                 695                 700
Val Leu Phe Trp Met Thr Phe Cys Val Ile Gly Gln Pro Met Ala Ile
705                 710                 715                 720
Leu Leu Tyr Thr Val Asp Tyr Gln Tyr Gly Lys His His Ser Thr Asn
            725                 730                 735
Met Glu Ile Phe Asp Thr Asp Asp Cys Arg Phe Leu Trp Lys Asn Ser
            740                 745                 750
Cys Leu Ile Arg
        755
```

US 9,410,132 B2

ACYL-COA: DIACYLGLYCEROL ACYLTRANSFERASE 1-LIKE GENE (PTDGAT1) AND USES THEREOF

FIELD OF INVENTION

This invention is directed to, inter alia, an isolated DNA molecule encoding acyl-CoA: diacylglycerol acyltransferase 1-like gene (PtDGAT1) from the diatom *Phaeodactylum tricornutum*, a protein encoded by same, and methods of making and utilizing the same.

BACKGROUND OF THE INVENTION

Triacylglycerols (TAG) are the principal carbon storage compounds in various organisms, including vertebrates, oilseed plants, oleaginous fungi, yeast and microalgae. In microalgae, TAGs are mainly accumulated in extraplastidial oil bodies, and are implied as potential resource of neutral lipids for biodiesel production.

TAG is synthesized de-novo by a sequential transfer of fatty acyl chains from acyl-CoA through the glycerol-3-phosphate (G3P) pathway, also known as the Kennedy pathway. Briefly, G3P is first acylated by the action of the acyl-CoA: glycerol-3-phosphate acyltransferase (GPAT), followed by a second acylation step catalyzed by the acyl-CoA: lysophosphatidate acyltransferase (LPAAT). The phosphatidic acid obtained is then dephosphorylated by a phosphatidate phosphatase (PAP) to generate diacylglycerol (DAG), which is finally used as substrate for the acyl-CoA: diacylglycerol acyltransferase (DGAT) to produce TAG. Consequently, DGAT catalyzes the final and committed step for TAG biosynthesis.

Three types of DGAT enzymes commonly referred to as DGAT type 1, 2, and 3, may take part in the acyl-CoA-dependent formation of TAG. Two major isoforms are encoded by DGAT1 and DGAT2 genes that have been identified to encode for distinct proteins which both function as DGAT enzymes and are responsible for the bulk of TAG synthesis in most organisms. Cytosolic DGAT3 has been discovered in peanut *Arachis hypogea*, but seems to play only a minor role in plant TAG formation.

DGAT1 (EC 2.3.1.20) proteins are members of the MBOAT (membrane-bound O-acyltransferase) protein superfamily and differ structurally from DGAT2 proteins. DGAT1 proteins are larger than DGAT2 and possess at least six transmembrane domains compared to the two predicted in DGAT2 (Yen et al., 2008). The emerging role of DGAT2 orthologs seems to be more important for incorporation of unusual fatty acids in the seed storage oils of some plants. In addition, the bifunctional DGAT/wax ester synthase from *Acinetobacter calcoaceticus*, is also a member of the MBOAT superfamily, however, for its higher plants homologs, the DGAT activity is either absent or much lower relative to the wax synthase activity.

SUMMARY OF THE INVENTION

In one embodiment, the present invention provides an isolated protein comprising an amino acid sequence set forth in SEQ ID NO 1.

In another embodiment, the present invention further provides a DNA molecule encoding a protein comprising an amino acid sequence set forth in SEQ ID NO 1.

In another embodiment, the present invention further provides a transgenic organism or a transformed bacteria comprising an exogenous polynucleotide molecule encoding a protein comprising an amino acid sequence set forth in SEQ ID NO 1.

In another embodiment, the present invention further provides a cell comprising an expression vector encoding a protein comprising an amino acid sequence set forth in SEQ ID NO: 1.

In another embodiment, the present invention further provides a method for enhancing a production of oil or triacylglycerols with high saturated fatty acids content in a cell, comprising the step of transforming the cell with a polynucleotide encoding a protein comprising an amino acid sequence set forth in SEQ ID NO 1, thereby enhancing a production of oil or triacylglycerols with high saturated fatty acids content in a cell.

In another embodiment, the present invention further provides a method for increasing the proportion of a saturated fatty acid in a cell, comprising the step of transforming or transfecting the cell with a polynucleotide encoding a protein comprising an, amino acid sequence set forth in SEQ ID NO 1, thereby increasing the proportion of a saturated fatty acid in a cell.

BRIEF DESCRIPTION OF THE DRAWINGS

FIG. 3. depicts the amino-acid sequence (565 AA) of PtDGAT1 gene obtained under nitrogen starvation. Underlined: N-terminal obtained from EST CT880495. Bold: ten C-terminal amino-acids (consensus C-terminal sequence of higher plant DGAT1) added to complete C-terminus (YHDIMNRKGN (SEQ ID NO 14-Stop). (Amino acids are not included in the gene model sequence XP_002177753.1, but were identified after cloning of the gene by sequencing of the PCR product).

FIG. 9. depicts the amino-acid sequence (756 AA) of the full-length PtDGAT1 including PHdomain gene obtained under nitrogen starvation (SEQ ID NO 4). Underlined: PH domain predicted using PROSITE-EXPASy software (http://prosite.expasy.org/).

DETAILED DESCRIPTION OF THE INVENTION

Figure 1A:
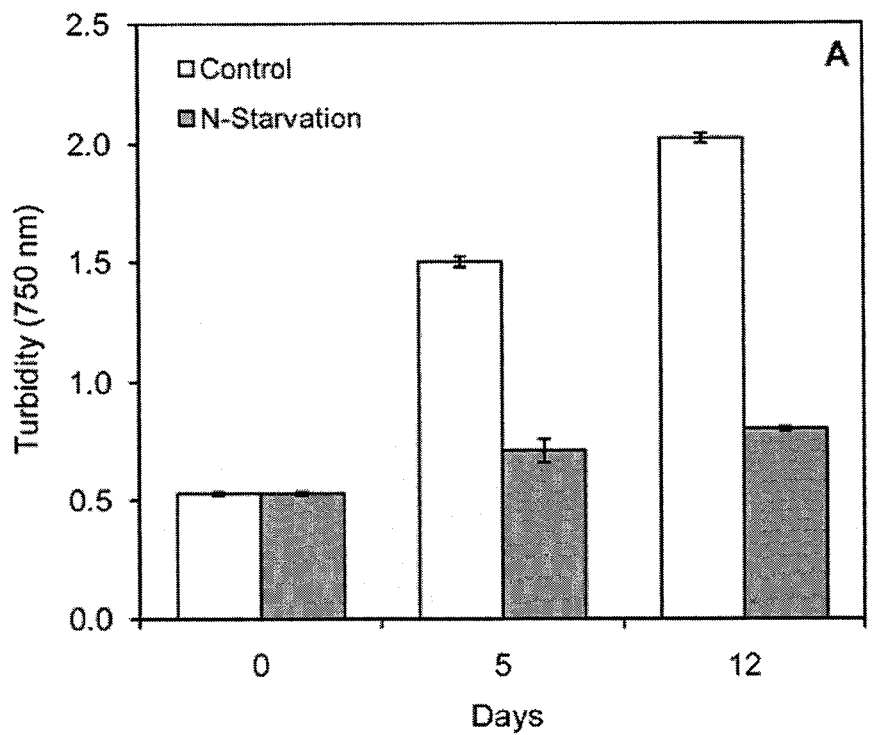
FIG. 1. is a set of bar graphs showing the Turbidity (A), Dry Weight (B), Chlorophyll a content (C) and Total Fatty Acid content (D) determined in *Phaeodactylum tricornutum* cultures at day 0, 5, 12 on full RSE medium (white columns), and under nitrogen starvation (grey columns).
Figure 1B:
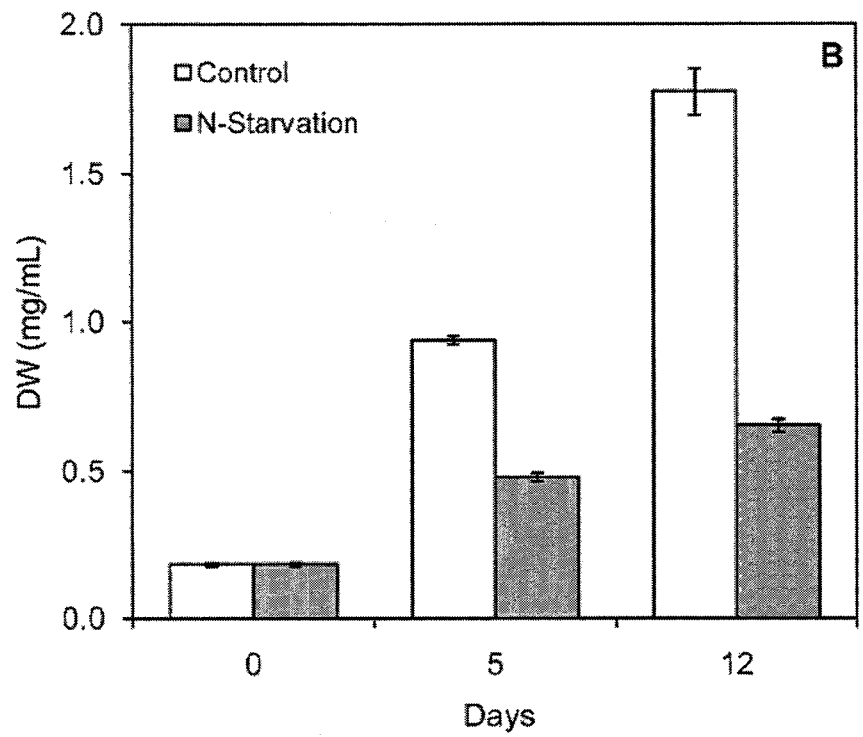
Figure 1C:
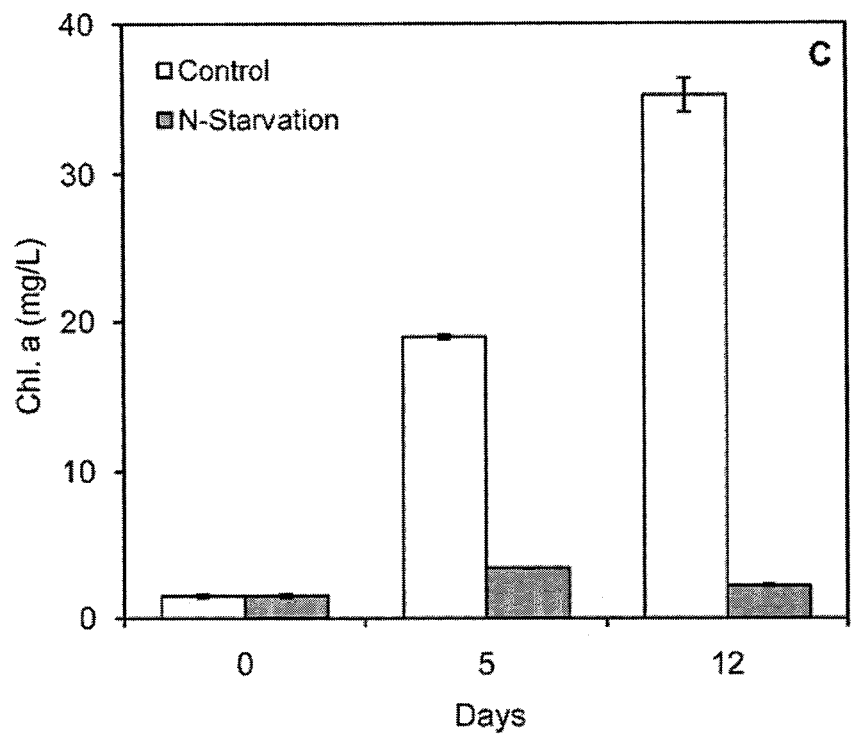
Figure 1D:
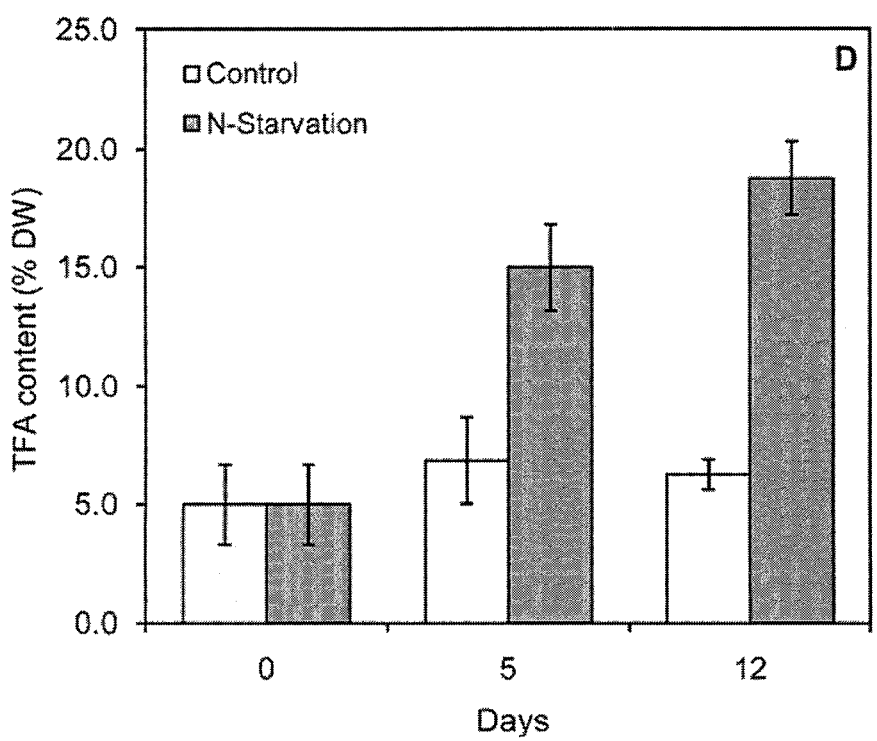

In one embodiment, the present invention provides an isolated acyl-coa: diacylglycerol acyltransferase 1-like gene (PtDGAT1) protein. In another embodiment, the present invention provides that the isolated PtDGAT1 protein is a microalga protein. In another embodiment, the present invention provides that the isolated PtDGAT1 protein is derived from a diatom microalga. In another embodiment, the present invention provides that the isolated PtDGAT1 protein is derived from *Phaeodactylum tricornutum*.

In another embodiment, the present invention provides a PtDGAT1 protein comprising or consisting the amino acid sequence:

```
                                                    (SEQ ID NO: 1)
DETEITPLLRFSTPSRAEHSSWIKLASESCAYSETDEFLADEAARATQR

ALQHQEALQMAQAMPGAKPGTLPPLYFAPTIKRSRSFAKLQEHHGDGMP

RVNMRRTKSRDFNADKLDARSTKGYPPSKPMHRAAEPSYLSADAPIQNY

RGFLNLGVIILIVSNFRLILGTIRSNGFVLTTAVKHYKNLNHLKEDPWQ

EFPPFVSGFLLQLVFVSIAFGIEWMLCRKYFNENFGMILHHFNAHSALLI

PLGIVWNLIDRPAVGAILLLHATITWMKLISYMLANEDYRLSSRRVGGN

PHLATLALVENLDSDEANINYPQNVTLRNIFYFWCAPTLTYQIAFPKSP

RVRYWKIADILMRMTVSIALFTFLLAQIVQPALEELVSDLDETNGSYTA

AIFAEYWLKLSIANTYLWLLMFYTYFHLYLNLFAELLRFGDRVFYKDWW

NSSEVSAYWRLWNMPVHYWLIRHVYFPCVRLKMPKVAATFVVFFLSAVM

HEVLVSVPFHIIRPWSFIGMMMQIPLVAFTKYLYRKFPGGSIGNVLFWM

TFCVIGQPMAILLY.
```

In another embodiment, the present invention provides a PtDGAT1 protein comprising or consisting the amino acid sequence:

```
                                                    (SEQ ID NO: 2)
MDETEITPLLRFSTPSRAEHSSWIKLASESCAYSETDEFLADEAARATQ

RALQHQEALQMAQAMPGAKPGTLPPLYFAPTIKRSRSFAKLQEHHGDGM

PRVNMRRTKSRDFNADKLDARSTKGYPPSKPMHRAAEPSYLSADAPIQN

YRGFLNLGVIILIVSNFRLILGTIRSNGFVLTTAVKHYKNLNHLKEDPW

QEFPPFVSGFLLQLVFVSIAFGIEWMLCRKYFNENFGMILHHFNAHSALL

IPLGIVWNLIDRPAVGAILLLHATITWMKLISYMLANEDYRLSSRRVGG

NPHLATLALVENLDSDEANINYPQNVTLRNIFYFWCAPTLTYQIAFPKS

PRVRYWKIADILMRMTVSIALFTFLLAQIVQPALEELVSDLDETNGSYT

AAIFAEYWLKLSIANTYLWLLMFYTYFHLYLNLFAELLRFGDRVFYKDW

WNSSEVSAYWRLWNMPVHYWLIRHVYFPCVRLKMPKVAATFVVFFLSAV
```

-continued

MHEVLVSVPFHIIRPWSFIGMMMQIPLVAFTKYLYRKFPGGSIGNVLFW

MTFCVIGQPMAILLY.

In another embodiment, the present invention provides a PtDGAT1 protein comprising or consisting the amino acid sequence:

(SEQ ID NO: 3)
MDETEITPLLRFSTPSRAEHSSWIKLASESCAYSETDEFLADEAARATQ

RALQHQEALQMAQAMPGAKPGTLPPLYFAPTIKRSRSFAKLQEHHGDGM

PRVNMRRTKSRDFNADKLDARSTKGYPPSKPMHRAAEPSYLSADAPIQN

YRGFLNLGVIILIVSNFRLILGTIRSNGFVLTTAVKHYKNLNHLKEDPW

QEFPFVSGFLLQLVFVSIAFGIEWMLCRKYFNENFGMILHHFNAHSALL

IPLGIVWNLIDRPAVGAILLLHATITWMKLISYMLANEDYRLSSRRVGG

NPHLATLALVENLDSDEANINYPQNVTLRNIFYFWCAPTLTYQTAFPKS

PRVRYWKIADILMRMTVSIALFTFLLAQIVQPALEELVSDLDETNGSYT

AAIFAEYWLKLSIANTYLWLLMFYTYFHLYLNLFAELLRFGDRVFYKDW

WNSSEVSAYWRLWNMPVHYWLIRHVYFPCVRLKMPKVAATFVVFFLSAV

MHEVLVSVPFHIIRPWSFIGMMMQIPLVAFTKYLYRKFPGGSIGNVLFW

MTFCVIGQPMAILLYYHDIMNRKGN.

In another embodiment, the present invention provides a PtDGAT1 protein comprising or consisting the amino acid sequence:

(SEQ ID NO: 4)
MTTPVSSEDTATLQQKIVALQAQLLSATHALERMKNERGASSADHSKSA

QRNGSDPSSDPTGTAPVAAPPAKSGYLFKELDRAIGWGGIKWSLRYVKL

ESGRISYYGSHHDTSPRYELQLRGCAVRDDGWKRNPRFKTKRNEPPPLL

DTTGAYFFLFSVYHAPDAAEKEIDETEITPLLRFSTPSRAEHSSWIKLA

SESCAYSETDEFLADEAARATQRALQHQEALQMAQAMPGAKPGTLPPLY

FAPTIKRSRSFAKLQEHHGDGMPRVNMRRTKSRDFNADKLDARSTKGYP

PSKPMHRAAEPSYLSADAPIQNYRGFLNLGVIILIVSNFRLILGTIRSN

GFVLTTAVKHYKNLNHLKEDPWQEFPFVSGFLLQLVFVSIAFGIEWMLC

RKYFNENFGMILHHFNAHSALLIPLGIVWNLIDRPAVGAILLLHATITW

MKLISYMLANEDYRLSSRRVGGNPHLATLALVENLDSDEANINYPQNVT

LRNIFYFWCAPTLTYQIAFPKSPRVRYWKIADILMRMTVSIALFTFLLA

QIVQPALEELVSDLDETNGSYTAAIFAEYWLKLSIANTYLWLLMFYTYH

TLYLNLFAELLRFGDRVFYKDWWNSSEVSAYWRLWNMPVHYWLIRHVYF

PCVRLKMPKVAATFVVFFLSAVMHEVLVSVPFHIIRPWSFIGMMMQIPL

VAFTKYLYRKFPGGSFGNVLFWMTFCVIGQPMAILLYTVDYQYGKHHST

NMEIFDTDDCRFLWKNSCLIR.

In another embodiment, the PtDGAT1 protein of the present invention comprises an amino acid sequence that is at least 50% homologous to the amino acid sequence of any one of SEQ ID NOs: 1-4. In another embodiment, the PtDGAT1 protein of the present invention comprises an amino acid sequence that is at least 60% homologous to the amino acid sequence of any one of SEQ ID NOs: 1-4. In another embodiment, the PtDGAT1 protein of the present invention comprises an amino acid sequence that is at least 70% homologous to the amino acid sequence of any one of SEQ ID NOs: 1-4. In another embodiment, the PtDGAT1 protein of the present invention comprises an amino acid sequence that is at least 80% homologous to the amino acid sequence of any one of SEQ ID NOs: 1-4. In another embodiment, the PtDGAT1 protein of the present invention comprises an amino acid sequence that is at least 85% homologous to the amino acid sequence of any one of SEQ ID NOs: 1-4. In another embodiment, the PtDGAT1 protein of the present invention comprises an amino acid sequence that is at least 90% homologous to the amino acid sequence of any one of SEQ ID NOs: 1-4. In another embodiment, the PtDGAT1 protein of the present invention comprises an amino acid sequence that is at least 95% homologous to the amino acid sequence of any one of SEQ ID NOs: 1-4. In another embodiment, the PtDGAT1 protein of the present invention comprises an amino acid sequence that is at least 99% homologous to the amino acid sequence of any one of SEQ ID NOs: 1-4.

In another embodiment, the PtDGAT1 protein of the present invention comprises an amino acid sequence that is at least 50% identical to the amino acid sequence of any one of SEQ ID NOs: 1-4. In another embodiment, the PtDGAT1 protein of the present invention comprises an amino acid sequence that is at least 60% identical to the amino acid sequence of any one of SEQ ID NOs: 1-4. In another embodiment, the PtDGAT1 protein of the present invention comprises an amino acid sequence that is at least 70% identical to the amino acid sequence of any one of SEQ ID NOs: 1-4. In another embodiment, the PtDGAT1 protein of the present invention comprises an amino acid sequence that is at least 80% identical to the amino acid sequence of any one of SEQ ID NOs: 1-4. In another embodiment, the PtDGAT1 protein of the present invention comprises an amino acid sequence that is at least 85% identical to the amino acid sequence of any one of SEQ ID NOs: 1-4. In another embodiment, the PtDGAT1 protein of the present invention comprises an amino acid sequence that is at least 90% identical to the amino acid sequence of any one of SEQ ID NOs: 1-4. In another embodiment, the PtDGAT1 protein of the present invention comprises an amino acid sequence that is at least 95% identical to the amino acid sequence of any one of SEQ ID NOs: 1-4. In another embodiment, the PtDGAT1 protein of the present invention comprises an amino acid sequence that is at least 99% identical to the amino acid sequence of any one of SEQ ID NOs: 1-4.

In another embodiment, the PtDGAT1 protein as described herein comprises at least a portion of the amino acid shown in SEQ ID. NO 1. In another embodiment, the PtDGAT1 protein as described herein is a variant of SEQ ID. NO 1. In another embodiment, the term "variant" in relation to a certain sequence means a protein or a polypeptide which is derived from the sequence through the insertion or deletion of one or more amino acid residues or the substitution of one or more amino acid residues with amino acid residues having similar properties, e.g., the replacement of a polar amino acid residue with another polar amino acid residue, or the replacement of a non-polar amino acid residue with another non-polar amino acid residue. In all cases, variants must have a PtDGAT1 protein function as defined herein.

In another embodiment, the PtDGAT1 protein as described herein further comprises a leader peptide. In another embodiment, the leader peptide allows the polypeptide to be specifically located or targeted to a target organelle within the cell.

In another embodiment, the present invention provides a *Phaeodactylum tricornutum* isolated PtDGAT1 protein of any one of SEQ ID NOs: 1-4. In another embodiment, the present invention provides an isolated polypeptide comprising a functional *Phaeodactylum tricornutum* PtDGAT1. In another embodiment, the present invention provides that the polypeptide has the function of a PtDGAT1 protein.

In another embodiment, the present invention provides an isolated polynucleotide encoding the protein as described herein. In another embodiment, the present invention provides an isolated polynucleotide encoding a protein comprising or consisting the amino acid sequence of anyone of SEQ ID NOs: 1-4. In another embodiment, an isolated polynucleotide is an isolated DNA molecule. In another embodiment, an isolated polynucleotide is an isolated cDNA molecule. In another embodiment, the isolated polynucleotide comprises a sequence encoding the protein as described herein. In another embodiment, the isolated polynucleotide comprises a DNA sequence encoding PtDGAT1 protein as described herein. In another embodiment, the isolated polynucleotide comprises a DNA sequence encoding a polypeptide comprising a PtDGAT1 protein activity. In another embodiment, the isolated polynucleotide comprises a DNA sequence encoding a polypeptide consisting a PtDGAT1 activity.

In another embodiment, the isolated polynucleotide comprises a DNA sequence comprising or consisting the sequence:

(SEQ ID NO: 5)
GATGAGACCGAAATTACACCTTTGTTGCGTTTTTCGACACCTTCCCGAG

CCGAACACTCGTCCTGGATAAAGCTTGCCTCGGAATCCTGTGCTTACAG

CGAAACGGACGAGTTTCTCGCTGACGAGGCCGCTCGCGCAACCCAGCGT

GCTTTGCAACATCAAGAAGCGCTGCAAATGGCCCAAGCCATGCCTGGGG

CAAAGCCAGGAACGCTGCCGCCACTCTACTTCGCGCCTACCATAAAGCG

TTCGCGTTCCTTTGCTAAGCTACAAGAACATCATGGAGATGGGATGCCT

CGGGTAAATATGCGTCGGACCAAATCGCGAGATTTTAACGCGGATAAGT

TGGATGCGCGAAGTACCAAGGGCTATCCCCCTTCCAAGCCGATGCATCG

TGCGGCAGAGCCCTCATACCTCAGCGCGGATGCTCCCATTCAAAACTAC

CGAGGATTTCTGAATTTAGGCGTTATTATTTTGATTGTTTCTAACTTTC

GGCTGATCTTGGGCACAATCCGTAGCAACGGATTTGTCTTGACGACTGC

AGTGAAGCACTACAAGAACCTAAATCACCTCAAGGAAGATCCCTGGCAG

GAATTTCCTTTTGTATCAGGATTTCTTCTCCAGCTCGTCTTTGTTTCGA

TTGCGTTTGGGATCGAATGGATGTTGTGCCGGAAATACTTCAACGAAAA

CTTCGGCATGATCCTTCATCACTTCAATGCCCACTCAGCCTTGCTGATA

CCTTTAGGTATTGTTTGGAATCTCATCGATAGACCTGCGGTTGGTGCAA

TTTTGCTTTTACACGCTACGATAACATGGATGAAACTCATTTCTTACAT

GTTGGCGAACGAAGATTACCGGCTATCATCGCGTCGCGTTGGGGCAAC

CCACACCTAGCTACGCTCGCATTAGTCGAAAATCTAGATTCAGATGAGG

CGAACATTAACTACCCCCAAAATGTTACTCTCCGCAACATTTTTATTT

TTGGTGTGCTCCGACGTTGACTTACCAGATTGCCTTCCCGAAGTCCCCG

CGAGTTCGCTATTGGAAAATCGCGGATATCCTGATGCGCATGACGGTGT

CCATCGCACTATTCACCTTTTTGCTGGCACAAATTGTTCAGCCTGCATT

GGAAGAGCTAGTGAGCGACCTGGACGAGACCAATGGATCCTACACCGCA

GCAATATTTGCCGAGTACTGGCTGAAACTTTCGATTGCTAACACATATT

TATGGCTTCTTATGTTCTATACATATTTCCATTTGTATCTGAACCTCTT

TGCTGAGCTTCTGCGATTTGGAGATCGTGTGTTCTACAAAGATTGGTGG

AATTCGTCGGAAGTATCTGCATATTGGAGGCTTTGGAATATGCCTGTTC

ACTATTGGTTGATCCGACATGTGTATTTCCCCTGCGTGCGACTGAAGAT

GCCGAAGGTCGCTGCAACCTTTGTCGTTTTTTCCTCTCCGCCGTTATG

CACGAGGTGCTTGTCAGCGTACCCTTTCATATTATTCGTCCGTGGTCTT

TTATCGGGATGATGATGCAGATTCCTTTGGTTGCGTTCACAAAGTATCT

CTATCGCAAATTCCCGGGCGGCTCGATTGGTAATGTCCTGTTCTGGATG

ACATTTTGCGTCATTGGCCAGCCAATGGCGATTCTCTTGTACTATCATG

ATATTATGAATCGAAAAGGAAATTGA.

In another embodiment, a PtDGAT1 as described herein comprises a nucleic acid sequence that is at least 50% homologous to the nucleic acid sequence of SEQ ID NO 5. In another embodiment, a PtDGAT1 of the present invention comprises a nucleic acid sequence that is at least 60% homologous to the nucleic acid sequence of SEQ ID NO 5. In another embodiment, a PtDGAT1 of the present invention comprises a nucleic acid sequence that is at least 70% homologous to the nucleic acid sequence of SEQ ID NO 5. In another embodiment, a PtDGAT1 of the present invention comprises a nucleic acid sequence that is at least 80% homologous to the nucleic acid sequence of SEQ ID NO 5. In another embodiment, a PtDGAT1 of the present invention comprises a nucleic acid sequence that, is at least 85% homologous to the nucleic acid sequence of SEQ ID NO 5. In another embodiment, a PtDGAT1 of the present invention comprises a nucleic acid sequence that is at least 90% homologous to the nucleic acid sequence of SEQ ID NO 5. In another embodiment, a PtDGAT1 of the present invention comprises a nucleic acid sequence that is at least 95% homologous to the nucleic acid sequence of SEQ ID NO 5. In another embodiment, a PtDGAT1 of the present invention comprises a nucleic acid sequence that is at least 99% homologous to the nucleic acid sequence of SEQ ID NO 5.

In another embodiment, a PtDGAT1 of the present invention comprises a nucleic acid sequence that is at least 50% identical to the nucleic acid sequence of SEQ ID NO 5. In another embodiment, a PtDGAT1 of the present invention comprises a nucleic acid sequence that is at least 60% identical to the nucleic acid sequence of SEQ ID NO 5. In another embodiment, a PtDGAT1 of the present invention comprises a nucleic acid that is at least 70% identical to the nucleic acid sequence of SEQ ID NO 5. In another embodiment, a PtDGAT1 of the present invention comprises a nucleic acid sequence that is at least 80% identical to the nucleic acid sequence of SEQ ID NO 5. In another embodiment, a PtDGAT1 of the present invention comprises a nucleic acid sequence that is at least 85% identical to the nucleic acid sequence of SEQ ID NO 5. In another embodiment, a PtDGAT1 of the present invention comprises a nucleic acid sequence that is at least 90% identical to the nucleic acid sequence of SEQ ID NO 5. In another embodiment, a PtDGAT1 of the present invention comprises a nucleic acid sequence that is at least 95% identical to the nucleic acid sequence of SEQ ID NO 5. In another embodiment, a PtDGAT1 of the present invention comprises a nucleic acid sequence that is at least 99% identical to the nucleic acid sequence of SEQ ID NO: 5.

In another embodiment, the present invention comprises a PtDGAT1 protein or a nucleic acid molecule encoding the same that enhances the production of TAGs, oil and lipid bodies. In another embodiment, the present invention comprises a PtDGAT1 protein or a nucleic acid molecule encoding the same that alters the fatty acid composition of TAGs, oil and lipid bodies in a cell. In another embodiment, the present invention comprises a PtDGAT1 protein or a nucleic acid molecule encoding the same that directs the biosynthesis of saturated fatty acids such as but not limited to 16:0 and/or 18:0 in a cell. In another embodiment, the present invention comprises a PtDGAT1 protein active within a cell. In another embodiment, the present invention comprises a PtDGAT1 protein active in an in-vitro system in the presence of lipid precursors. In another embodiment, lipid precursors comprise various polyunsaturated C18- and C20-fatty acids of both ω3 and ω6 groups. In another embodiment, lipid precursors comprise endogenous DAG and acyl-CoA pool for acylation. In another embodiment, lipid precursors comprise TAGs.

In another embodiment, the PtDGAT1 protein of the invention is active in a cell exposed to nitrogen starvation conditions. In another embodiment, the PtDGAT1 protein of the invention is active in a microalgal cell exposed to nitrogen starvation conditions. In another embodiment, the PtDGAT1 protein of the invention is active in an alga under nitrogen starvation conditions. In another embodiment, the PtDGAT1 protein of the invention is active in a microalga under nitrogen starvation conditions. In another embodiment, the PtDGAT1 protein of the invention is active in a cell comprising the lipid precursors necessary for the formation of saturated fatty acids-TAGs. In another embodiment, the PtDGAT1 protein of the invention is active in an organism comprising the lipid precursors necessary for the formation of saturated fatty acids-TAGs. In another embodiment, the PtDGAT1 protein of the invention is active in a yeast culture comprising the lipid precursors necessary for the formation of saturated fatty acids-TAGs. In another embodiment, the PtDGAT1 protein of the invention is active in-vitro in the presence of lipid precursors necessary for the formation of saturated fatty acids-TAGs.

In another embodiment, the PtDGAT1 protein of the invention directs the incorporation of various poly-unsaturated fatty acids (PUFAs) into a TAG. In another embodiment, the PtDGAT1 protein of the invention primarily directs the incorporation of saturated fatty acids into a TAG. In another embodiment, the PtDGAT1 protein of the invention has a clear preference for saturated fatty acids such as but not limited to 16:0 and 18:0 species (versus unsaturated fatty acids such as the monounsaturated 16:1 and 18:1). In another embodiment, the PtDGAT1 protein of the invention has a clear preference for endogenous saturated fatty acids such as but not limited to 16:0 and 18:0 species (versus unsaturated fatty acids such as the monounsaturated 16:1 and 18:1). In another embodiment, active PtDGAT1 protein forms TAGs that are substantially saturated. In another embodiment, active PtDGAT1 protein forms TAGs that are substantially saturated relative to the equivalent ones formed by the yeast protein encoded by the DGA1 gene. In another embodiment, active PtDGAT1 protein enhances the accumulation of 20:5 n-3 in TAG. In another embodiment, active PtDGAT1 protein prefers n-3 C20-PUFA over n-6 C20-PUFA.

In another embodiment, the present invention comprises a PtDGAT1 protein or a nucleic acid molecule encoding the same combined with additional proteins and/or enzymes and/or substrates that are involved in the biosynthesis of TAGs, oil, and lipid bodies. In another embodiment, the present invention comprises a PtDGAT1 protein or a nucleic acid molecule encoding the same combined with additional proteins and/or enzymes and/or substrates that are involved in the biosynthesis of saturated fatty acids such as but not limited to 16:0 and/or 18:0.

In another embodiment, the present invention comprises a PtDGAT1 protein or a nucleic acid molecule encoding the same combined with additional proteins and/or enzymes and/or substrates that are involved in the biosynthesis of *P. tricornutum* TAGs. In another embodiment, the present invention comprises a PtDGAT1 protein or a nucleic acid molecule encoding the same combined with additional proteins and/or enzymes and/or substrates that are involved in the biosynthesis of *P. tricornutum* TAGs under nitrogen starvation conditions.

In another embodiment, a cell is a microbial cell, a microalgae cell, an alga cell, a plant cell, a cell derived from a heterotrophic microorganism, or a yeast cell. In another embodiment, alga comprises microalga. In another embodiment, a cell to be used with the methods of the invention is grown under nutrient-deplete conditions such as nitrogen starvation. In another embodiment, a cell to be used with the methods of the invention is grown under slow cell proliferation conditions.

In another embodiment, the present invention provides a method for increasing the proportion of a saturated fatty acid in a cell, comprising the step of transforming a cell with a polynucleotide encoding a PtDGAT1 protein. In another embodiment, the present invention provides a method for increasing the proportion of a saturated fatty acid in a TAG in a cell, comprising the step of transforming a cell with a polynucleotide encoding a PtDGAT1 protein. In another embodiment, increasing the proportion of a saturated fatty acid in a cell or a TAG comprises decreasing the proportion unsaturated fatty acid in a cell or a TAG. In another embodiment, the present invention provides a method for producing or enhancing the production of oil or triacylglycerols with high saturated fatty acids content. In another embodiment, the present invention provides a method increasing the saturated fatty acids content in oil and/or triacylglycerols. In another embodiment, the present invention provides a method increasing the proportion of saturated fatty acids in oil and/or triacylglycerols. In another embodiment, increasing or enhancing comprises high expression of a polynucleotide molecule of the invention. In another embodiment, provided a method of producing cellular TGAs and/oil rich in saturated fatty acids, comprising the step of over-expressing a PtDGAT1 in the cell. In another embodiment, provided a method of producing cellular TAGs and/oil with high saturated fatty acids content or proportion, comprising the step of over-expressing a PtDGAT1 in the cell.

In another embodiment, the present invention comprises a method of producing oil, triacylglycerols, or a combination thereof in a cell comprising the step of transforming a cell with a polynucleotide encoding a PtDGAT1 protein as described herein. In another embodiment, the present invention comprises a method of producing oil rich in saturated fatty acids, triacylglycerols rich in saturated fatty acids, or a combination thereof in a cell comprising the step of transforming a cell with a polynucleotide encoding a PtDGAT1 protein as described herein. In another embodiment, the present invention comprises a method of enhancing the production of oil rich in saturated fatty acids, triacylglycerols rich in saturated fatty acids, or a combination thereof in a cell comprising the step of transforming a cell with a polynucleotide encoding a PtDGAT1 protein as described herein. In another embodiment, a polynucleotide encoding a PtDGAT1 protein as described herein is transiently or constitutively expressed in the cell.

In another embodiment, the present invention comprises a method of producing oil rich in saturated fatty acids, triacylglycerols rich in saturated fatty acids, or a combination thereof in a cell comprising the step of transforming a cell with a polynucleotide encoding a PtDGAT1 protein as described herein to be used as biodiesel.

In another embodiment, the present invention provides that PtDGAT1 prefers saturated acyl moieties 16:0 and 18:0 over monounsaturated 16:1 and 18:1. In another embodiment, the fact that PtDGAT1 prefers saturated acyl moieties 16:0 and 18:0 over monounsaturated 16:1 and 18:1 and therefore, over-expression of PtDGAT1 is of high value for increasing of production and improving the fatty acid composition of microalgal oils for biodiesel production. In another embodiment, provided a method of producing biodiesel, comprising the step of over-expressing a PtDGAT1 in a cell. In another embodiment, the use of cells over-expressing PtDGAT1 enables the increase of production and/or improvement of the fatty acid, composition of oils produced in cells for biodiesel production. In another embodiment, the use of cells over-expressing PtDGAT1 enables the increase of production and/or improvement of the fatty acid composition of microalgal oils for biodiesel production.

In another embodiment, the present invention comprises a composition comprising a PtDGAT1 protein as described herein or a nucleic acid molecule encoding the same. In another embodiment, the present invention comprises a composition comprising fatty acids and/or TAGs produced by a cell transformed or transfected with PtDGAT1 as described herein. In another embodiment, the present invention includes a composition comprising oil produced in a cell transformed or transfected with PtDGAT1 as described herein. In another embodiment, the present invention comprises a composition comprising any constituent of an oil body produced by a transgenic or transformed organism comprising a polynucleotide molecule encoding the PtDGAT1 protein as described herein. In another embodiment, the present invention comprises a composition comprising the PtDGAT1 protein as described herein or a nucleic acid molecule encoding the same combined with additional proteins and/or enzymes and/or substrates that are involved in the biosynthesis of oil, lipids, fatty acids, and/or TAGs. In another embodiment, the present invention comprises a composition comprising a cell transfected or transformed by a nucleic acid molecule encoding the PtDGAT1 protein as described herein. In another embodiment, the cell is a prokaryotic cell. In another embodiment, the cell is a eukaryotic cell. In another embodiment, the cell is a plant cell. In another embodiment, the cell is an algal cell.

In another embodiment, provided herein a transgenic organism transformed by a polynucleotide of the invention. In another embodiment, the organism is a plant. In another embodiment, the organism is yeast. In another embodiment, the organism is a seed. In another embodiment, the organism is an alga. In another embodiment, the organism is a microalga. In another embodiment, provided herein a seed or an offspring of a transgenic organism as described herein wherein the seed or offspring expresses the PtDGAT1 protein as described herein.

In another embodiment, the present invention comprises a PtDGAT1 transgenic plant or a PtDGAT1 transformed bacteria. In another embodiment, the present invention comprises a PtDGAT1 transgenic microalga or alga. In another embodiment, the present invention comprises a PtDGAT1 transgenic plant or a PtDGAT1 transformed bacteria combined with additional enzymes and/or substrates that are involved in the biosynthesis of oil, lipids, fatty acids, and/or TAGs rich in saturated fatty acids.

In another embodiment, the present invention comprises a *P. tricornutum* over-expressing the PtDGAT1 protein as described herein. In another embodiment, the present invention comprises a cell or an organism over-expressing PtDGAT1 protein. In another embodiment, the present invention comprises a cell or an organism over-expressing an endogenic or exogenic PtDGAT1 protein. In another embodiment, the present invention provides that over-expression of PtDGAT1 protein results in hyper production of oil, lipids, fatty acids, and/or TAGs. In another embodiment, the present invention provides that over-expression of PtDGAT1 protein results in hyper production of oil, and/or TAGs characterized by high content and/or proportion of saturated fatty acids such as but not limited to 18:0 and 16:0.

In another embodiment, a genetically engineered organism and/or *P. tricornutum* as described herein is transformed with a vector comprising a polynucleotide molecule encoding PtDGAT1 protein under the control of a constitutively active promoter. In another embodiment, a genetically engineered organism and/or *P. tricornutum* as described herein is transformed with a vector comprising a polynucleotide molecule encoding a self PtDGAT1 protein under the control of a constitutively active promoter. In another embodiment, *P. tricornutum* is transformed with a vector comprising a polynucleotide molecule encoding a self PtDGAT1 protein under the control of a constitutively active promoter. In another embodiment, *P. tricornutum* is transformed with a vector comprising the polynucleotide molecule of SEQ ID NO 5 under the control of a constitutively active promoter. In another embodiment, *P. tricornutum* is transformed with a vector comprising a polynucleotide molecule encoding the protein comprising or consisting the amino acid sequence SEQ ID NO 1, under the control of a constitutively active promoter. In another embodiment, yeast, an alga or microalga as described is transformed according to the methods described in EP1789530 which is hereby incorporated herein by reference in its entirety. In another embodiment, the methods described in EP1789530 are used for the introduction of an endogenous PTDGAT1 (such as the one encoded by SEQ ID NO 2) into competent microalgae cells, thereby over-expressing PtDGAT1 protein and enhancing the biogenesis of oil and/or TAGS characterized by high saturated fatty acid content.

In another embodiment, the expression of a PtDGAT1 as described herein is controlled by a cell specific promoter. In another embodiment, the expression of a PtDGAT1 as described herein is controlled by a yeast promoter. In another embodiment, the expression of a PtDGAT1 as described herein is controlled by a plant promoter. In another embodiment, the expression of a PtDGAT1 as described herein is controlled by an algal promoter. In another embodiment, the expression of a PtDGAT1 as described herein is controlled by a bacterial promoter. In another embodiment, the expression of a PtDGAT1 as described herein is controlled by a viral promoter.

In another embodiment, the expression of PtDGAT1 protein as described herein is controlled by a constitutive promoter. In another embodiment, the expression of PtDGAT1 protein as described herein is controlled by a constitutive promoter whose expression is independent of environmental and/or developmental factors. In another embodiment, the expression of PtDGAT1 protein as described herein is controlled by a constitutive promoter whose expression is independent of endogenous factors.

In another embodiment, the expression of PtDGAT1 protein as described herein is controlled by a tissue-specific or development-stage-specific promoter. In another embodiment, the expression of PtDGAT1 protein as described herein is controlled by a promoter element that is expressed or affect the expression of genes in the vascular system, photosynthetic tissues, tubers, roots and/or other vegetative organs, or seeds and/or other reproductive organs.

In another embodiment, the expression of PtDGAT1 protein as described herein is controlled by an inducible promoter. In another embodiment, the expression of PtDGAT1 protein as described herein is controlled by an inducible promoter conditioned to environmental conditions and external stimuli that can be artificially controlled. In another embodiment, the expression of PtDGAT1 protein as described herein is controlled by an inducible promoter conditioned to an abiotic factor such as light, oxygen levels, nitrogen, heat, cold and wounding. In another embodiment, the expression of PtDGAT1 protein as described herein is controlled by an inducible promoter conditioned to a chemical compound, not found naturally in the organism of interest. In another embodiment, the expression of PtDGAT1 protein as described herein is controlled by an inducible promoter conditioned to an antibiotic, copper, alcohol, steroids, and/or herbicides, among other compounds.

In another embodiment, the expression of PtDGAT1 protein as described herein is controlled by a synthetic promoter. In another embodiment, a synthetic promoter is made by bringing together the primary elements of a promoter region from diverse origins.

In another embodiment, the expression of PtDGAT1 protein as described herein is controlled by a regulatory expression system based on transactivating proteins. In another embodiment, a regulatory expression system regulates the expression of genes of interest irrespective of their physical position to the target genes.

In another embodiment, a vector is used according to the cell or organism utilized. In another embodiment, bacterial, yeast, algal, plant, and animal cell vectors are readily available to one of average skill in the art. In another embodiment, vector control elements are used according to the cell, organism, or tissue utilized. In another embodiment, bacterial, yeast, plant, and animal cell vector control elements are readily available to one of average skill in the art. In another embodiment, vector control elements comprise an origin of replication and a promoter.

In another embodiment, the present invention provides a composition comprising a vector comprising the polynucleotide as described herein. In another embodiment, the present invention provides a composition comprising a vector comprising a polynucleotide encoding PtDGAT1 protein as described herein.

In another embodiment, one of skill in the art can readily prepare a composition as described herein. In another embodiment, one of skill in the art can readily prepare a composition comprising a polynucleotide as described herein. In another embodiment, one of skill can readily prepare a composition comprising a combination of polynucleotides, plasmids, vectors etc. as described herein. In another embodiment, the present invention provides a composition comprising PtDGAT1 protein as described herein to be used in industrial applications for the manufacturing biodiesel. In another embodiment, a composition as described herein is a kit comprising the components for the in vitro manufacturing of TAGs and/or oil comprising high saturated fatty acids content.

In another embodiment, provided herein a method of producing TAGs and/or oil comprising high saturated fatty acids content in a cell comprising the step of transforming or transfecting a cell with a polynucleotide as described herein, thereby producing TAGs and/or oil comprising high saturated fatty acids content in a cell. In another embodiment, provided herein a method for increasing the content of saturated fatty acid stored in TAGs and/or oil in a cell, comprising the step of over-expressing a polynucleotide sequence encoding PtDGAT1 protein in a cell. In another embodiment, the cell is any cell. In another embodiment, methods for over-expressing or de-novo expressing a protein encoded by a vector such as a plasmid are known to one of average skill in the art.

In another embodiment, provided herein a method for increasing the incorporation of saturated fatty acids into TAGs. In another embodiment, provided herein a method for increasing the incorporation of saturated fatty acids into TAGs in a heterotrophic microorganism, comprising the step of over-expressing a polynucleotide sequence as described herein.

In another embodiment, over-expressing a polynucleotide sequence encoding a self (endogenous) PtDGAT1 protein or an exogenous PtDGAT1 protein in a cell, results according to the methods of the present invention in enhancement of production of oil and/or TAGs with increased saturated fatty acids content or proportion. In another embodiment, cells or organisms of the invention that over express a polynucleotide sequence encoding a self (endogenous) PtDGAT1 protein or an exogenous PtDGAT1 protein are used as a source for biodiesel.

In another embodiment, enhancement or enhancing production and/or expression is measured against control cells exposed to the same conditions which do not express PtDGAT1 protein according to the present invention. In another embodiment, enhancement or enhancing production and/or expression is measured against control cells exposed to the same conditions which do not over-express PtDGAT1 protein according to the present invention.

In another embodiment, the method for enhancing a production of oil and/or TAGs with increased saturated fatty acids content or proportion in a cell further comprises the step of subjecting the cell to a condition selected from high light, high salinity, low nutrients, or any combination thereof. In another embodiment, the method for increasing or de-novo producing oil and/or TAGs with increased saturated fatty acids content or proportion in a cell further comprises the step of subjecting the cell to temperate conditions.

In another embodiment, algae as described herein are eukaryotic organisms. In another embodiment, algae as described herein are photoautotrophic. In another embodiment, algae as described herein are mixotrophic. In another embodiment, algae as described herein are unicellular. In another embodiment, algae as described herein are multicellular. In another embodiment, algae as described herein are Excavata algae. In another embodiment, algae as described herein are Rhizaria algae. In another embodiment, algae as described herein are Chromista algae. In another embodiment, algae as described herein are Alveolata algae.

In another embodiment, algae as described herein are Chlorophyta. In another embodiment, algae as described herein are Haematococcaceae. In another embodiment, alga is a freshwater alga or microalga. In another embodiment, algae as described herein produce saturated fatty acids.

In another embodiment, overexpression of PtDGAT1 protein in a cell results in an increase in the saturated fatty acids content of oil and/or triacylglycerols in a cell. In another embodiment, overexpression of PtDGAT1 protein in a cell results in an increase in the proportion of saturated fatty acids in oil and/or triacylglycerols. In another embodiment, overexpression of PtDGAT1 protein in a cell results in a decrease in the proportion of unsaturated fatty acids in oil and/or triacylglycerols. In another embodiment, overexpression of PtDGAT1 protein in a cell results in a decrease in the proportion of monounsaturated fatty acids in oil and/or triacylglycerols.

In another embodiment, transforming a first alga with an algal gene derived from a second alga results in enhanced production of oil and/or TAGs with increased saturated fatty acids content. In another embodiment, transforming a first alga with an algal gene derived from a second alga results in enhanced or de-novo production of oil and/or TAGs with increased saturated fatty acids content. In another embodiment, transforming an alga with an algal gene derived from the same alga such as described herein results in enhanced production of oil and/or TAGs with increased saturated fatty acids content.

In another embodiment, increasing and/or enhancing the production of oil and/or TAGs with increased saturated fatty acids content is increasing and/or enhancing the absolute content of saturated fatty acids. In another embodiment, increasing and/or enhancing the production of oil and/or TAGs with increased saturated fatty acids content is increasing and/or enhancing the proportion of saturated fatty acids. In another embodiment, increasing and/or enhancing the production of oil and/or TAGs with increased saturated fatty acids content is increasing and/or enhancing the proportion of saturated fatty acids and decreasing the proportion of unsaturated fatty acid such as monounsaturated fatty acids.

In another embodiment, the present invention provides an expression vector comprising the polynucleotide as described herein. In another embodiment, the present invention provides a combination of expression vectors each comprising a polynucleotide as described herein. In another embodiment, the present invention provides a plant specific expression vector comprising the polynucleotide as described herein. In another embodiment, the present invention provides an algal specific expression vector comprising the polynucleotide as described herein. In another embodiment, the present invention provides a cell comprising the expression vector/s as described herein. In another embodiment, the expression vector/s is contained within an *agrobacterium*. In another embodiment, a cell is a bacterial cell, an animal cell, plant cell or an algal cell.

In another embodiment, the present invention provides a transformed bacterium, a transgenic plant, a transgenic seed, or a transgenic alga transformed by a polynucleotide as described herein. In another embodiment, the present invention provides a transformed bacterium, a transgenic plant, a transgenic seed, or a transgenic alga transformed by any combination of polynucleotides as described herein. In another embodiment, the present invention provides that the transgenic plant is true-breeding for the polynucleotide/s as described herein. In another embodiment, the present invention provides a transgenic seed, produced by a transgenic plant transformed by the polynucleotide/s as described herein. In another embodiment, transformed bacteria, a transformed cell, a transgenic plant, transgenic seed, or a transgenic alga as described herein produces oil or TAGs with high saturated fatty acids content or proportion. In another embodiment, transformed bacteria, a transformed cell, a transgenic plant, a transgenic seed, or a transgenic alga as described herein produces oil or TAGs with decreased unsaturated fatty acids content or proportion. In another embodiment, transformed bacteria, a transformed cell, a transgenic plant, transgenic seed, or a transgenic alga as described herein produces oil or TAGs with decreased monounsaturated fatty acids content or proportion.

In another embodiment, "proportion" refers to the proportion of saturated to unsaturated fatty acids. In another embodiment, "proportion" refers to the proportion of saturated to unsaturated fatty acids in a cell. In another embodiment, "proportion" refers to the proportion of saturated to monounsaturated fatty acids. In another embodiment, "proportion" refers to the proportion of saturated to monounsaturated fatty acids in a cell.

In another embodiment, expression of the protein/s of the invention in plants or seed requires sub-cloning an ORF/s sequence encoding the protein/s into a plant expression vector, which may comprise a viral 35S promoter, and a Nos terminator. In another embodiment, a cassette or promoter/coding sequence/terminator is then be subcloned into the plant binary transformation vector, and the resulting plasmid introduced into *Agrobacterium*. In another embodiment, the *Agrobacterium* strain transforms the plant. In another embodiment, the *Agrobacterium* strain transforms the plant by the vacuum-infiltration of inflorescences, and the seeds harvested and plated onto selective media containing an antibiotic. In another embodiment, the plasmid confers resistance to an antibiotic, thus only transformed plant material will grow in the presence of an antibiotic. In another embodiment, resistant lines are identified and self: fertilized to produce homozygous material. In another embodiment, leaf material is analyzed for expression of the PtDGAT1 protein. In another embodiment, transformation as described herein is a nuclear transformation. In another embodiment, transformation as described herein is organella transformation. In another embodiment, transformation as described herein is a chloroplast transformation. In another embodiment, transformation of as described herein is a mitochondrial transformation.

In another embodiment, the present invention provides that the methods as described herein can be utilized for the de-novo production of oil and/or TAGs with increased saturated fatty acids content in a cell. In another embodiment, the present invention provides that the methods as described herein can be utilized for the production of oil and/or TAGs with increased saturated fatty acids content in cells or organisms that do not produce oil and/or TAGs with increased saturated fatty acids content endogenically (in the wild-type). In another embodiment, the present invention provides that the methods as described herein can be utilized for production of oil and/or TAGs with increased saturated fatty acids content in plant cells or a plant.

In another embodiment, the present invention provides that transforming a cell or an organism, transfecting a cell or creating a transgenic organism in accordance to the methods of the invention results in enhancing the production of oil and/or TAGs with increased saturated fatty acids content or proportion in cells that naturally produce oil and/or TAGs with increased saturated fatty acids content or proportion. In another embodiment, the present invention provides that transforming a cell or an organism, transfecting a cell, or creating a transgenic organism in accordance to the invention results in an enhancing the production of oil and/or TAGs with increased amount of saturated fatty acids content or proportion in cells that do not naturally produce oil and/or TAGs with increased amount of saturated fatty acids.

In another embodiment, the terms "enhanced production", "over expression", "increased production", and "induced production", are used interchangeably.

In another embodiment, the level of expression of PtDGAT1 protein correlates with the saturation index of TAGs in a cell. In another embodiment, the level of expression of PtDGAT1 protein correlates with the amount of saturated fatty acids in a cell subjected to conditions that favor the production of saturated fatty acids as described herein. In another embodiment, enhanced production of oil and/or TAGs with increased amount of saturated fatty acids in a cell is the result of the introduction of a vector comprising a DNA molecule as described herein under the control of a promoter as described herein into a cell. In another embodiment, enhanced production of oil and/or TAGs with increased amount of saturated fatty acids in a cell is the result of the introduction of a vector comprising a DNA molecule as described herein under the control of a promoter as described herein into a cell as described herein.

In another embodiment, enhanced expression of PtDGAT1 protein in a cell or an organism results in enhanced production of oil and/or TAGs with increased amount of saturated fatty acids compared to the amount of oil and/or TAGs with increased amount of saturated fatty acids present in a cell or an organism prior to the introduction of a DNA molecule as described herein.

In another embodiment, enhanced expression of PtDGAT1 protein as described herein results in 5% increase in saturated fatty acids in oil and/or TAGs present in a cell. In another embodiment, enhanced expression of PtDGAT1 protein as described herein results in 3-10% increase in saturated fatty acids in oil and/or TAGs present in a cell. In another embodiment, enhanced expression of PtDGAT1 protein as described herein results in 7-20% increase in saturated fatty acids in oil and/or TAGs present in a cell. In another embodiment, enhanced expression of PtDGAT1 protein as described herein results in 10-30% increase in saturated fatty acids in oil and/or TAGs present in a cell. In another embodiment, enhanced expression of PtDGAT1 protein as described herein results in 10-80% increase in saturated fatty acids in oil and/or TAGs present in a cell. In another embodiment, enhanced expression of PtDGAT1 protein as described herein results in 10-100% increase in saturated fatty acids in oil and/or TAGs present in a cell. In another embodiment, enhanced expression of PtDGAT1 protein as described herein results in 30-120% increase in saturated fatty acids in oil and/or TAGs present in a cell. In another embodiment, enhanced expression of PtDGAT1 protein as described herein results in 25-500% increase in saturated fatty acids in oil and/or TAGs present in a cell. In another embodiment, enhanced expression of PtDGAT1 protein as described herein results in 10-50% increase in saturated fatty acids in oil and/or TAGs present in a cell. In another embodiment, enhanced expression of PtDGAT1 protein as described herein results in 15-75% increase in saturated fatty acids in oil and/or TAGs present in a cell. In another embodiment, enhanced expression of PtDGAT1 protein as described herein results in 30-70% increase in saturated fatty acids in oil and/or TAGs present in a cell. In another embodiment, enhanced expression of PtDGAT1 protein as described herein results in 25-50% increase in saturated fatty acids in oil and/or TAGs present in a cell.

In another embodiment, provided herein that the conditions for enhancing saturated fatty acids content in oil and/or TAGs comprise environmental conditions such as but not limited to light intensity (170 µmol m$^{-2}$s$^{-1}$), phosphate starvation and salt stress (NaCl 0.8%). In another embodiment, provided herein that the conditions for enhancing saturated fatty acids content in oil and/or TAGs comprise conditions wherein cell growth is retarded. In another embodiment, cell growth is retarded as reflected by a decrease in cell division rate. In another embodiment, cell growth is retarded as reflected by an increase in cell death. In another embodiment, provided herein that the conditions for enhancing saturated fatty acids content in oil and/or TAGs require cell growth/algal growth under nitrogen depravation. In another embodiment, provided herein that the conditions for enhancing/enriching saturated fatty acids content in oil and/or TAGs require a change in the cell stage from biflagellate vegetative green cell to a non-motile and large resting cell. In another embodiment, provided herein that environmental and/or nutritional stresses, which interfere with cell division, trigger and/or enhance the production of oil and/or TAGs rich in saturated fatty acids content. In another embodiment, provided herein that the conditions for enhancing saturated fatty acids content in oil and/or TAGs comprise contacting the algal cells with an inhibitor of cell division. In another embodiment, saturated fatty acids, oil and/or TAGs content is measured both in weight (mg/g) and in cellular (pg/cell) contents.

In another embodiment, provided herein that the conditions for enhancing saturated fatty acids content in oil and/or TAGs comprise a high dose of light. In another embodiment, provided herein that the conditions for enhancing saturated fatty acids content in oil and/or TAGs comprise a high dose of irradiation. In another embodiment, provided herein that the conditions for enhancing saturated fatty acids content in oil and/or TAGs comprise a combination of nitrogen depravation and a salt or an ester of an acid such as acetate addition.

In another embodiment, methods for isolating oil and/or TAGs from cells, alga, microalga, a bacteria, or yeast are known to one of average skill in the art.

In another embodiment, an engineered organism is engineered to express PtDGAT1 protein as described herein. In another embodiment, an engineered organism is engineered to highly express PtDGAT1 protein as described herein. In another embodiment, an engineered plant or alga as described herein is used for the manufacturing of TAGs and/or oil with high saturated fatty acid content. In another embodiment, an engineered cell, an engineered plant or alga, as described herein is used for increasing the proportion and/or amount of TAGs and/or oil comprising high saturated fatty acid content. In another embodiment, an engineered plant as described herein is used for manufacturing desired saturated fatty acid.

In another embodiment, the terms "protein", "PtDGAT1 protein", or "polypeptide" are used interchangeably. In some embodiments, the terms "protein", "PtDGAT1 protein", or "polypeptide" as used herein encompass native polypeptides (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides/proteins even more stable while in-vivo or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C.A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are, substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylene bonds (—CO—CH2-). In some embodiments, the polypeptide bonds are substituted by α-aza bonds (—NH—N(R)—CO—), wherein R is any alkyl, e.g., methyl, carbo bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS=NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g., fatty acid, complex carbohydrates, etc.).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides or proteins of the present invention are utilized in a soluble form. In some embodiments, the polypeptides or proteins of the present invention include one or more non-natural or natural polar amino acid, including but not limited to serine and threonine which are capable of increasing polypeptide or protein solubility due to their hydroxyl-containing side chain.

In some embodiments, the polypeptides or proteins of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides or proteins of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide or protein synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides or proteins are purified by preparative high performance liquid chromatography [Creighton T. (1983) Proteins, structures and molecular principles. WH Freeman and Co. N.Y.], and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, N.Y., Section VIII, pp 421-463.

In one embodiment, a polypeptide or protein of the present invention is synthesized using a polynucleotide encoding a polypeptide or protein of the present invention as described herein. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention. In another embodiment, a polypeptide is a protein comprising a ST activity as described herein.

In another embodiment, the polynucleotide comprises a genomic polynucleotide sequence. In another embodiment, the polynucleotide comprises a composite polynucleotide sequence.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In one embodiment, following expression, the signal peptides are cleaved from the precursor proteins resulting in the mature proteins.

In some embodiments, polynucleotides of the present invention are prepared using PCR techniques or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g., plant expression systems) to express the polypeptide of the present invention.

In one embodiment, yeast expression systems are used. In one embodiment, algae expression systems are used. In one embodiment, plant expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In another embodiment, expression in a host cell can be accomplished in a transient or a stable fashion. In another embodiment, a host cell is a cell as described herein. In another embodiment, transient expression is from introduced constructs which contain expression signals functional in the host cell, but which constructs do not replicate and rarely integrate in the host cell, or where the host cell is not proliferating. In another embodiment, transient expression also can be accomplished by inducing the activity of a regulatable promoter operably linked to the gene of interest.

In another embodiment, stable expression is achieved by introduction of a construct that integrates into the host genome. In another embodiment, stable expression comprises autonomously replication within the host cell. In another embodiment, stable expression of the polynucleotide of the invention is selected for through the use of a selectable marker located on or transfected with the expression construct, followed by selection for cells expressing the marker. In another embodiment, stable expression results from integration, the site of the construct's integration can occur randomly within the host genome or can be targeted through the use constructs containing regions of homology with the host genome sufficient to target recombination with the host locus. In another embodiment, constructs are targeted to an endogenous locus, all or some of the transcriptional and translational regulatory regions can be provided by the endogenous locus.

In another embodiment, an expression of a protein as described herein comprising PtDGAT1 activity as described herein includes functional transcriptional and translational initiation and termination regions that are operably linked to the DNA encoding the protein comprising an PtDGAT1 activity. In another embodiment, an expression of proteins as described herein comprising various PTDGAT1 activities includes functional transcriptional and translational initiation and termination regions that are operably linked to the DNA encoding the proteins comprising PtDGAT1 activity. In another embodiment, an expression of proteins as described herein comprising PtDGAT1 activity includes functional transcriptional and translational initiation and termination regions that are operably linked to the DNA encoding the protein comprising PtDGAT1 activity. In another embodiment, transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. In another embodiment, expression in a plant tissue and/or plant part presents certain efficiencies, particularly where the tissue or part is one which is harvested early, such as seed, leaves, fruits, flowers, roots, etc. In another embodiment, expression can be targeted to that location in a plant by utilizing specific regulatory sequences that are known to one of skill in the art. In another embodiment, the expressed protein is an enzyme which produces a product which may be incorporated, either directly or upon further modifications, into a fluid fraction from the host plant. In another embodiment, expression of a protein of the invention, or antisense thereof, alters the levels of specific PUFAs, or derivatives thereof, found in plant parts and/or plant tissues. The PTDGAT1 coding region, in some embodiments, may be expressed either by itself or with other genes, in order to produce cells, tissues, algae, and/or plant parts containing higher proportions of desired oil and/or TGA (as described herein). In another embodiment, the PTDGAT1 coding region is expressed either by itself or with other genes, in order to produce cells, tissues, yeast, algae, and/or plant parts containing higher proportions of oil and/or TGA enriched with saturated fatty acids. In another embodiment, the termination region is derived from the 3' region of the gene from which the initiation region was obtained from or from a different gene. In another embodiment, the termination region usually is selected as a matter of convenience rather than because of any particular property. In another embodiment, increasing or enhancing oil and/or TGA saturated fatty acids content or proportion is enriched oil and/or TGA with saturated fatty acids.

In another embodiment, a plant or plant tissue is utilized as a host or host cell, respectively, for expression of the protein of the invention which may, in turn, be utilized in the production of polyunsaturated fatty acids. In another embodiment, desired oil or fatty acids such as but not limited to 16:0 and 18:0 are produced in a seed. In another embodiment, methods of isolating seed oils are known in the art. In another embodiment, seed oil components are manipulated through the expression of the protein of the invention in order to provide seed oils that can be added to nutritional compositions, pharmaceutical compositions, animal feeds and cosmetics. In another embodiment, a vector which comprises a DNA sequence encoding the protein as described herein is linked to a promoter, and is introduced into the plant tissue or plant for a time and under conditions sufficient for expression of the protein.

In another embodiment, a vector as described herein comprises additional genes that encode other enzymes, involved in TGA, oil, and/or fatty acids synthesis and/or modification. In another embodiment, the bacteria, plant tissue or plant produces the relevant substrate upon which the enzymes act or a vector encoding enzymes which produce such substrates may be introduced into the plant tissue, plant cell or plant. In another embodiment, a substrate is in contact with the bacteria, or is sprayed on plant tissues expressing the appropriate enzymes. In another embodiment, the invention is directed to a transgenic plant comprising the above-described vector, wherein expression results in increased production of TGAs enriched with saturated fatty acids in, for example, the seeds of the transgenic plant.

In another embodiment, the regeneration, development, and cultivation of plants from single plant protoplast transformants or from various transformed explants is well known in the art (for example: Weissbach and Weissbach, In Methods for Plant Molecular Biology, (Eds.), Academic Press, Inc. San Diego, Calif., (1988)). In another embodiment, regeneration and growth process comprises the steps of selection of transformed cells, culturing those individualized cells through the usual stages of embryonic development through the rooted plantlet stage. In another embodiment, transgenic embryos and seeds are similarly regenerated. In another embodiment, resulting transgenic rooted shoots are thereafter planted in an appropriate plant growth medium such as soil. In another embodiment, regeneration and growth process of algae are known to one of skill in the art. In another embodiment, identification, selection, of transgenic algae are known to one of skill in the art.

In another embodiment, development or regeneration of plants containing an exogenous polynucleotide as described herein encodes a protein as described herein and is well known in the art. In another embodiment, development or regeneration of algae containing an exogenous polynucleotide as described herein encodes a protein as described herein and is well known in the art. In another embodiment, the regenerated plants are self-pollinated to provide homozygous transgenic plants. In another embodiment, pollen obtained from the regenerated plants is crossed to seed-grown plants of agronomically important lines. In another embodiment, pollen from plants of these important lines is used to pollinate regenerated plants. In another embodiment, a transgenic plant of the present invention containing a desired polypeptide is cultivated using methods well known to one skilled in the art.

In another embodiment, a variety of methods can be utilized for the regeneration of plants from plant tissue. In another embodiment, the method of regeneration will depend on the starting plant tissue and the particular plant species to be regenerated. In another embodiment, methods for transforming dicots, primarily by use of *Agrobacterium tumefaciens*, and obtaining transgenic plants are known in the art McCabe et al., Biol. Technology 6:923 (1988), Christou et al., Plant Physiol. 87:671-674 (1988)); Cheng et al., Plant Cell Rep. 15:653657 (1996), McKently et al., Plant Cell Rep. 14:699-703 (1995)); Grant et al., Plant Cell Rep. 15:254-258, (1995).

In another embodiment, transformation of monocotyledons using electroporation, particle bombardment, and *Agrobacterium* are known. In another embodiment, transformation and plant regeneration are well established in the art. In another embodiment, assays for gene expression based on the transient expression of cloned nucleic acid constructs have been developed by introducing the nucleic acid molecules into plant cells by polyethylene glycol treatment, electroporation, or particle bombardment (Marcotte et al., Nature 335: 454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

In another embodiment, transient expression systems are used to functionally dissect the oligonucleotides constructs. In another embodiment, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In one embodiment, the expression vector of the present invention can further include additional polynucleotide sequences that allow, for example, the translation of several proteins from a single mRNA such as an internal ribosome entry site (TRES) and sequences for genomic integration of the promoter-chimeric polypeptide.

In some embodiments, expression vectors containing regulatory elements from eukaryotic viruses such as retroviruses are used by the present invention. In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus, and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6) 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, N.Y., Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide or protein), the expression construct of the present invention can also include sequences engineered to, optimize stability, production, purification, yield or activity of the expressed polypeptide or protein.

In some embodiments, transformed cells are cultured under effective conditions, which allow for the expression of high amounts of recombinant polypeptide or protein having PtDGAT1 activity. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide or protein of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and Petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides or proteins of the present invention either remain within the recombinant cell, secreted into the fermentation medium, secreted into a space between two cellular membranes, or retained on the outer surface of a cell or viral membrane.

In one embodiment, following a predetermined time in culture, recovery of the recombinant polypeptide or protein is effected.

In one embodiment, the phrase "recovering the recombinant polypeptide or protein" used herein refers to collecting the whole fermentation medium containing the polypeptide or protein and need not imply additional steps of separation or purification.

In one embodiment, polypeptides or proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide or proteins of the present invention and fused cleavable moiety. In one embodiment, a fusion protein can be designed so that the polypeptide or protein can be readily isolated by affinity chromatography; e.g., by immobilization on a column specific for the cleavable moiety. In one embodiment, a cleavage site is engineered between the polypeptide or protein and the cleavable moiety and the polypeptide or protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide or protein of the present invention is retrieved in "substantially pure" form.

In one embodiment, the phrase "substantially pure" refers to a purity that allows for the effective use of the protein in the applications described herein.

In one embodiment, the polypeptide or protein of the present invention can also be synthesized using in vitro expression systems. In one embodiment, in vitro synthesis methods are well known in the art and the components of the system are commercially available.

In another embodiment, oil and/or TAGs with high saturated fatty acids or free saturated fatty acids produced by the methods as described herein are used in the cosmetic industry, biodiesel industry, the drug industry, food additives industry, baby food industry or any other applicable industry. In another embodiment, oil and/or TAGs with high saturated fatty acids or free saturated fatty acids produced by the methods as described herein are used within a formulation.

In some embodiments, the proteins or oligonucleotides of the invention modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified proteins or oligonucleotides of the invention exhibit substantially longer half-lives in blood following intravenous injection than do the corresponding unmodified compounds. In one embodiment, modifications also increase the proteins or oligonucleotides solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Experimental Procedures

Materials, and Methods

Growth Conditions

Axenic cultures of *P. tricornutum* were cultivated on RSE medium in 250-mL Erlenmeyer glass flasks in an incubator shaker under an air/$CO_2$ atmosphere (99:1, v/v) and controlled temperature (25° C.) and illumination (100 µmol quanta $m^{-2}$ $s^{-1}$) at a speed of 150 rpm. RSE medium was composed of 34 g $l^{-1}$ ReefSalt (Seachem™, Madison Ga., USA) complemented as following: 18.8 mM $KNO_3$, 0.51 mM $KH_2PO_4$, 10.6 mM $Na_2SiO_3.9H_2O$, 0.77 µM $ZnSO_4.7H_2O$, 0.31 µM $CuSO_4.5H_2O$, 1.61 µM $Na_2MoO_4.2H_2O$, 46.3 µM $H_3BO_3$, 9.15 µM, M $MnCl_2.4H_2O$, 0.172 µM $Co(NO_3)_2.6H_2O$, 26.8 µM $C_6H_5O_7Fe.5H_2O$, 46.8 µM citric acid, 50 µg $l^{-1}$ vitamin B12, 50 µg $l^{-1}$ biotin, and 0.1 mg $l^{-1}$ thiamine HCl. For the onset of nitrogen starvation conditions, daily-diluted cultures were centrifuged, cells washed twice, and resuspended in nitrogen-free RSE medium. Cultures were further grown under the same conditions before harvesting for RNA isolation. The nitrogen-free medium was prepared by omitting $KNO_3$ from the RSE medium. Growth parameters: turbidity, Ch1 a and DW content were determined as previously described (Solovchenko of al., 2008).

RNA Isolation and cDNA Synthesis

Total RNA was isolated by the procedure described by Bekesiova et al. (1999), from 35 mL culture grown in the complete RSE medium or in nitrogen-free RSE medium for 5 days. The cells were harvested before by centrifugation at 3000 rpm during 5 min, flash-frozen in liquid nitrogen and stored at −80° C. for further use Total RNA samples were treated with RNA-free Baseline-ZERO™ DNase (Epicentre Technologies, Madison, Wis., USA) before being used for cDNA synthesis. cDNA was prepared from 1 µg total RNA-template using the Verso™ cDNA kit (Thermo Fisher Scientific).

Identification and Cloning of PtDGAT1 Gene

Detailed searches using bioinformatics tools and available databases have been employed to find putative DGAT candidates in the genome of *P. tricornutum*. A hypothetical *P. tricornutum* protein (XP_002177753.1), containing ORF of 404 amino acids, exhibited significant similarity (38% identity, 55% similarity) to the coding region of maize DGAT1-2 protein (EU039830). A putative full-length cDNA encoding for PtDGAT1 (534 amino acids) including a putative N-terminal (130 amino acids) was further assembled from the nucleotide sequence of hypothetical protein XM_002177717.1 and the expressed sequence tag (EST CT880495) from *P. tricornutum*, which share a 400 base common overlap. The sequences of oligonucleotide primers that were used in this study are given in Table 1. The ORF coding for the putative PtDGAT1 polypeptide of 545 amino acids was amplified using the PfuUltra II fusion HS DNA polymerase (Stratagene, La Jolla, Calif., USA) with the forward primer (PtDGATfor-KnpI) containing a KnpI restriction site (underlined) and a yeast translation initiation consensus followed by ATG (bold), and the reverse primer (PtDGATrev-XhoI) containing a C-terminal extension, a XhoI restriction site (underlined) and a stop codon (Bold). Since hypothetical protein XP_002177753.1 lacks at least 10 amino acids conserved in C-terminus of higher plant DGAT1 proteins and a stop codon, ten C-terminal aminoacids, including endoplasmatic reticulum retrieval motifs (ER-DIR: YYHD) were added during amplification by incorporating a 33 base nucleotides sequence into the reverse primer encoding for amino acids YHDIMNRKGN (SEQ ID NO 14-Stop). The PCR products of the expected size were excised, purified from the gel (Nucleospin Extract II purification kit; Macherey-Nagel, Duren, Germany), cloned into pGEM®-T Easy Vector Systems (Promega), and several clones were sequenced for each condition.

TABLE 1

Oligonucleotide primers used in this study

| Sequence | Primer |
|---|---|
| 5' CGC<u>GGTACCATG</u>GATGAGACCGAAATTACA C 3' (SEQ ID NO: 6) | PtDGATfor-KnpI |
| 5' GGC<u>CTCGAG</u><b>TCA</b>ATTTCCTTTTCGATTCATAATATCATGATAGTACAAGAGAATCGCCATTGG 3' (SEQ ID NO: 7) | PtDGATrev-XhoI |
| 5' <u>GGATCCACATA</u><b>ATG</b>TCAGGAACATTCAATGATATAAG 3' (SEQ ID NO 8) | DGA1-fBamHI |
| 5' <u>TGCGGCCGC</u><b>TTA</b>CCCAACTATCTTCAATTCTGCATC 3' (SEQ ID NO 9) | DGA1-rNotI |
| 5' ATGACCACGCCTGTATCTTC 3' (SEQ ID NO: 10) | PtDGAT1-PHfor |
| 5' TCAACGAATCAAGCAGGAAT 3' (SEQ ID NO: 11) | PtDGAT1-PHrev |

As positive control in yeast expression assays, the yeast DGA1 gene encoding DGAT1 was cloned similarly to the PtDGAT1 of *P. tricornutum*, using the forward primer (DGA1-fBamHI) and reverse primer (DGA1-rNotI).

Further research using bioinformatics tools and available databases have been used to find the promoter upstream of the assembled putative full-length sequence encoding for PtDGAT1 (1653 bp), which was successfully expressed and functionally characterized in a *S. cerevisiae* neutral lipid-deficient quadruple mutant strain H1246. During the assembly (1653 bp) the start-codon was artificially added, by modifying ATT to ATG instead, after the KnpI restriction site in the forward primer PtDGATfor-KnpI. By bioinformatic searches, a new Pleckstrin Homology (PH) domain was found upstream to the artificial methionine of the catalytically important region of PtDGAT1. Consequently, new primers PtDGAT1-PHfor and PtDGAT1-PHrev have been designed (see Table 1) to amplify a putative full-length cDNA sequence encoding for PtDGAT1 including -PHdomain (756 amino acids). The ORF for PtDGAT1 (including -PHdomain) gene is assumed to contain the genuine start-codon, and the native C-terminal sequence. This domain is similar to the PH domain recently annotated in the diatom *Thalassiosira pseudonana* DGAT1 (ADV58933.2) and is absent in other DGAT1 proteins previously characterized.

Expression and Functional Characterization of PtDGAT1 cDNA by the Heterolgous Expression in Yeast *Saccharomyces cerevisiae*

*S. cerevisiae* strains used were BY742 (relevant genotype: MATa his3Δ1 leu2Δ0 met15Δ0 ura3Δ0); and H1246 (relevant genotype: MATa ADE2-1 can1-100 ura3-1 are1-Δ::HIS3 are2-Δ::LEU2 dga1-Δ::KanMX4 lro1-Δ::TRP1) containing knockouts of the DGA1, LRO1, ARE1 and ARE2 genes, was kindly provided by Prof S. Stymne (Scandinavian Biotechnology Research, Alnarp, Sweden). Before transformation, yeast cells were cultivated in 1% (w/v) Yeast extract, 2% (w/v) Peptone and 2% (w/v) Glucose (YPG medium) at 30° C.

Plasmids (pGEM®-T Easy Vector Systems Promega), harboring the assembled full-length sequence encoding for PtDGAT1 (1653 bp), was then restricted with KnpI and XhoI (NEB, Ipswich, Mass., USA). The expected bands were purified from the gel (Nucleospin Extract II purification kit; Macherey-Nagel, Duren, Germany), ligated into a KnpI-XhoI cut pYES2 vector (Invitrogen, Carlsbad, Calif., USA), and the *S. cerevisiae* strains were transformed by the PEG/lithium acetate method (Ausubel et al., 1995). The yeast H1246 and BY742 cells harboring the empty pYES2 vector were used as negative and positive controls, respectively; and as second positive control the yeast H1246 cells harboring the yeast DGA1 gene were used Transformants were selected by uracil prototrophy on yeast synthetic medium (YSM) lacking uracil (Invitrogen).

For functional expression, a minimal selection medium containing 2% (w/v) raffinose was inoculated with the PtDGAT1 transformants and grown at 30° C. for 24 h in a water bath shaker. Twenty mL of sterile YSM was inoculated with raffinose-grown cultures to obtain an OD of 0.2 at 600 nm. Expression was induced by adding galactose to a final concentration of 2% (w/v) and cultures were further grown at 30° C. for 48 h. For fatty acid substrate specificity of PtDGAT1 vs. *S. cerevisiae* DGA1, supplementation of YSM cultures with α-linolenic acid (ALA, 18:3 n-3), γ-linolenic acid (GLA, 18:3 n-6), eicosatrienoic acid (ETA, 20:3 n-3), arachidonic acid (ARA, 20:4n-6), and eicosapentaenoic acid (EPA, 20:5 n-3) in some experiments was carried with 250 µM of appropriate fatty acid in the presence of 1% (w/v) Tergitol-40 (precursors). Cells were harvested by centrifugation, washed twice with 0.1% $NaHCO_3$, freeze-dried, and used for lipid analysis.

Nile Red Staining and Microscopy

The Nile Red staining method described by Greenspan et al. (1985) was used to visualize the intracellular lipid bodies as an indicator for TAG formation. Aliquots of yeasts cultures (200 µL) grown during 48 h were harvested, stained with 2 µL Nile Red (0.5 g $mL^{-1}$ in dimethylsulfoxide), incubated at room temperature for 5 min, and observed immediately by fluorescent microscopy (Carl Zeiss, Germany). Filter allowing maximum excitation wavelength at 450-490 nm and a 520 nm cut-off filter were used.

Lipid Extraction and Analysis

For the lipid analysis of yeast expression cultures, yeast cells were harvested by centrifugation, the resulting pellets were transferred into glass vials, treated with isopropanol at 80° C. during 10-15 min to stop lipolytic activities, and homogenized in 2 mL of chloroform/methanol (½, v/v). Lipids were extracted at 4° C. with continuous mixing for 4 h followed by a second extraction step with 2 mL of chloroform/methanol (2/1, v/v) for 16 h. The resulting organic phases were combined, washed with 1.4 mL of 0.9% NaCl (w/v) and dried under vacuum. The remaining lipids, representing the total lipid extract, were resuspended in 100 µL of chloroform/methanol (1/1, v/v). The neutral lipid composition of the total lipid extracts was analyzed by Thin Layer Chromatography (TLC). Aliquots of the total lipid extracts were applied manually to Silica Gel 60 plates (Merck) and chromatograms were developed in a mixture of petroleum ether/diethyl ether/glacial acetic acid (70/30/1, v/v/v). Lipid standards were included on each TLC plate. TAGs were recovered from the TLC plates for GC analysis by extraction with chloroform. For visualization, plates were sprayed by a solution of 10% $H_2SO_4$ in methanol, and heated until spots appeared.

Fatty Acid Analysis

For fatty acid and lipid analysis of *P. tricornutum*, cells were harvested from liquid cultures. Fatty acid methyl esters (FAME) from total lipid, and TAG were obtained by transmethylation of the freeze-dried cells or TAG extracts with dry methanol containing 2% (v/v) $H_2SO_4$ and heating at 80° C. for 1.5 h while stirring under an argon atmosphere. Gas chromatographic analysis of FAME was performed on a Thermo Ultra gas chromatograph (Thermo Scientific, Italy) equipped with PTV injector, FID, and a fused silica capillary column (30 m×0.32 mm; Supelco WAX-10, Sigma-Aldrich). FAMEs were identified by co-chromatography with authentic standards (Sigma Chemical, St Louis, Mo., USA) and FAME of fish oil (Larodan Fine Chemicals, Sweden). Each sample was analyzed in triplicate.

Example 1

Lipid Content and Fatty Acid Composition of *P. tricornutum*

The effects of nitrogen starvation on growth parameters and total fatty acids (TFA) content were monitored in batch cultures of *P. tricornutum* (FIG. 1). During starvation, turbidity, DW and Chl a content decreased dramatically in comparison to nitrogen-sufficient cultures. The decreases in growth parameters were accompanied by an increase in the TFA content which reached 19% of DW after 12 days, while the sharpest increase occurred within the first 5 days. Under Nitrogen starvation, biomass lipid content of *P. tricornutum* increased about four-fold in comparison to the culture grown on full RSE medium.

The fatty acid composition of *P. tricornutum* (Table 2) was characterized by a large fraction of palmitic (16:0), palmitoleic (16:1) and eicosapentaenoic acids (EPA, 20:5 n-3). On full RSE medium, palmitoleic acid showed a substantial increase (from 21 to 30% of TFA) during growth, and represented about three-quarters of total fatty acids with palmitic acid by the end of the stationary phase. Conversely, other fatty acids decreased slightly with culture age (e.g. palmitic and stearic acids) whereas no significant change was observed in the relative proportion of eicosapentaenoic acid. Under nitrogen starvation, the main alterations in TFA profile were accounted for by relative increase of palmitic and palmitoleic acids (from 17 to 31% of TFA, and from 28 to 37% of TFA, respectively) concomitant with the decrease in the EPA proportion (from 22 to 7% of TFA).

TABLE 2

Fatty acid composition of *P. tricornutum* cultured under nitrogen starvation

| Time (days) | | | | | |
|---|---|---|---|---|---|
| 12 | | 5 | | 0 | Fatty acids |
| N− | N+ | N− | N+ | N+ | (% TFA) |
| Saturated fatty acids | | | | | |
| 4.5 | 5.9 | 4.7 | 5.8 | 5.8 | 14:0 |
| 31.1 | 14.8 | 29.0 | 14.7 | 17.1 | 16:0 |
| 1.5 | 1.2 | 1.5 | 1.2 | 4.6 | 18:0 |
| 0.2 | tr | 0.2 | 0.2 | 0.4 | 20:0 |
| 0.2 | 0.2 | 0.2 | 0.3 | 0.4 | 22:0 |
| 37.4 | 22.2 | 35.6 | 22.2 | 28.3 | Sum SFAs |
| Monounsaturated fatty acids | | | | | |
| 42.6 | 32.0 | 39.0 | 33.2 | 23.9 | 16:1 |
| 4.0 | 2.9 | 3.8 | 2.2 | 2.9 | 18:1 n-9 |
| 2.6 | 0.9 | 2.0 | 1.1 | 1.7 | 18:1 n-7 |
| — | — | — | 0.2 | 0.7 | 20:1 |
| 49.2 | 35.8 | 44.8 | 36.7 | 29.2 | Sum MUFAs |
| Polyunsaturated fatty acids | | | | | |
| 0.4 | 3.0 | 0.6 | 2.7 | 2.4 | 16:2 |
| 0.9 | 5.8 | 1.9 | 7.3 | 4.9 | 16:3 |
| 0.2 | 0.4 | 0.3 | 0.6 | 0.2 | 16:4 |

TABLE 2-continued

Fatty acid composition of *P. tricornutum* cultured under nitrogen starvation

| Time (days) | | | | | |
|---|---|---|---|---|---|
| 12 | | 5 | | 0 | Fatty acids |
| N− | N+ | N− | N+ | N+ | (% TFA) |
| 1.0 | 2.3 | 1.3 | 1.6 | 2.6 | 18:2 |
| 0.7 | 0.5 | 0.8 | 0.4 | 1.2 | 18:3 n-6 |
| 0.2 | 1.7 | 0.5 | 1.0 | 3.0 | 18:3 n-3 |
| 0.2 | 0.5 | 0.4 | 0.4 | 1.0 | 18:4 |
| tr | 0.4 | 0.3 | 0.4 | 1.3 | 20:2 |
| tr | — | — | — | 0.4 | 20:3 n-3 |
| 1.5 | 1.3 | 1.3 | 1.2 | 0.8 | 20:4 n-6 (ARA) |
| tr | tr | tr | — | 0.7 | 20:4 n-3 |
| 7.0 | 23.6 | 10.2 | 23.5 | 21.9 | 20:5 n-3 (EPA) |
| 1.0 | 2.4 | 2.0 | 2.0 | 2.1 | 22:6 n-3 (DHA) |
| 13.4 | 42.0 | 19.6 | 41.1 | 42.5 | Sum PUFAs |
| 18.9 | 6.3 | 15.0 | 6.9 | 5.0 | TFA (% DW) |

Example 2

Isolation and Identification of DGAT1 in *P. tricornutum*

Since nitrogen starvation induces TAG biosynthesis in *P. tricornutum*, a cDNA isolated from algae cultivated under nitrogen starvation conditions for 5 days was utilized. The PCR-amplification utilizing a forward primer designed on the basis of the EST (CT880495) and a reverse primer designed based on the nucleotide sequences of the predicted protein (XM_002177717.1), yielded a DNA fragment of 1695 bp putatively encoding for the full-length coding sequence of PtDGAT1. When cDNA was isolated from algal cells grown on complete nutrient RSE medium, a band of 1759 bp (designated as PtDGAT1long) was amplified using the same pair of primers. Importantly, both sequences appeared to be slightly longer than the DNA size of 1602 bp (PhaeoJoined-Seq), predicted from assembling the database sequences of the predicted hypothetical mRNA for protein (XM_002177717.1) with the EST (CT880495) from *P. tricornutum*.

Both DNA sequences were cloned into pGEM-T® Easy Vector Systems and sequenced. The two resulting sequences, PtDGAT1 and PtDGAT1long differ by a single insert of 63 bases introducing stop codons into the PtDGAT1 open reading frame, suggesting that PtDGAT1long is likely a splice variant with possible regulatory function (Insert II cDNA sequence: TAAGCCCACGTCTGCTGCATTCAGTGT-GATTTCCGTTTCCATGACTTACACCGCA TTTCGTAG (SEQ ID NO 12); Insert amino-acid sequence: AHVC-CIQCDFRFHDLHRIS (SEQ ID NO 13)). This insert introduced stop codons in the ORF of PtDGAT1.

The nucleotide sequences were aligned to the predicted gene sequence (XM_002177717.1, http://www.ebi.ac.uk/Tools/clustalw2/index.html), and to three *P. tricornutum* EST sequences (ct887168, ct881105, ct880495) showing similarity to the hypothetical *P. tricornutum* protein (XP_002177753.1), and to the coding region of MBOAT family proteins. The sequences determined by us and the EST sequences differed from the predicted gene sequence (XM_002177717.1) by presence of another additional fragment of 54 bp that does not affect the open reading frame, and was apparently erroneously excluded during the predicted gene assembly (XM_002177717.1).

Figure 2:
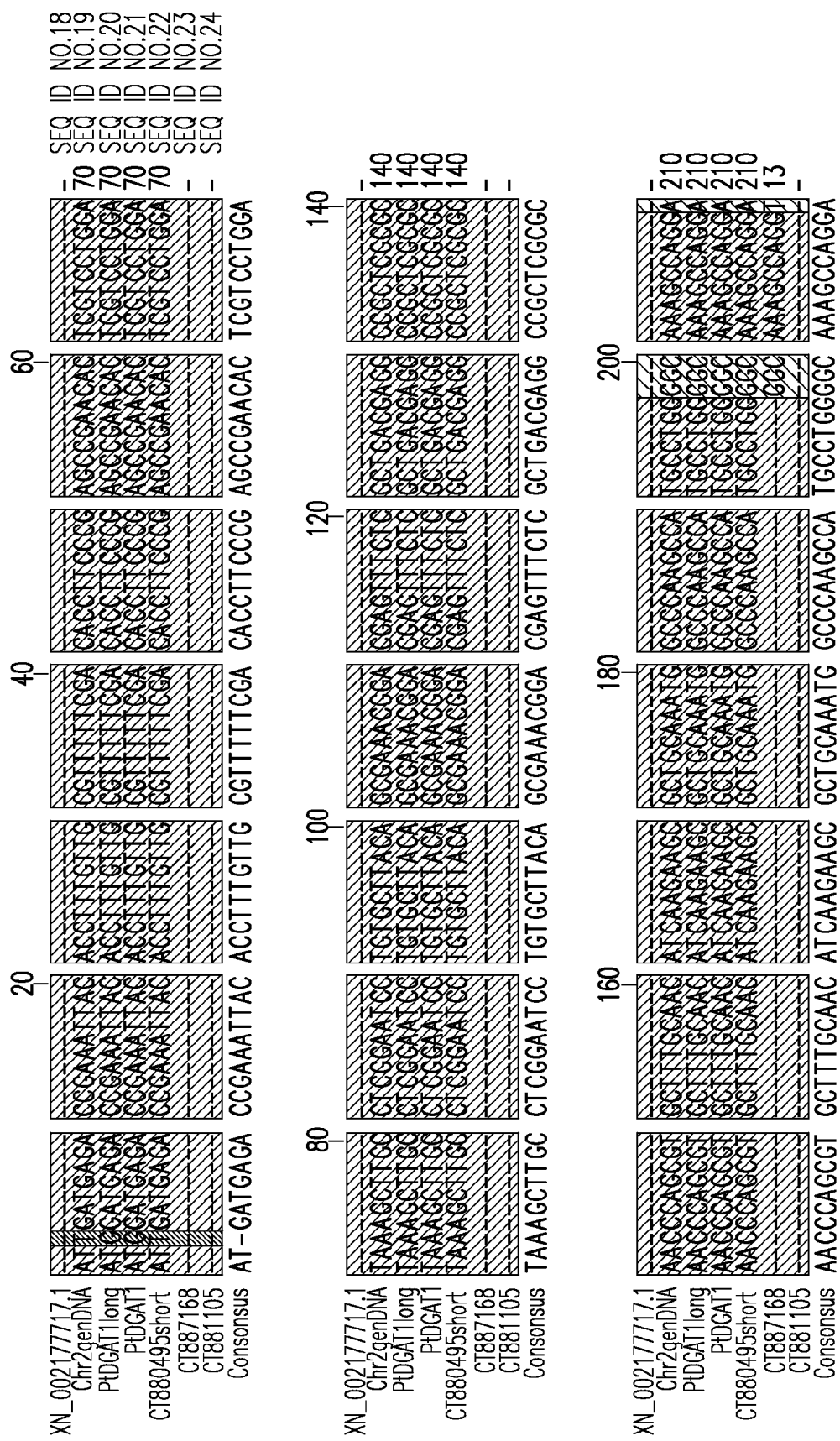
FIG. 2. depicts an alignment of cDNA sequences for the PtDGAT1 and PtDGAT1long, isolated from *Phaeodactylum tricornutum*, with the chromosome 2 genomic DNA (Chr2genDNA), the three EST sequences (ct887168, ct881105, ct880495short), and, the putative gene sequence (XM_002177717.1). Intron I of 65 bp (light gray continuous line box), Insert I of 54 bp that does not affect the open reading frame (black dotted line box), Insert II of 63 bp that introduces a stop codon in the ORF of PtDGAT1 (black continuous line box), C-terminal extension of 33 bp (light gray dotted line box).
Figure 2:
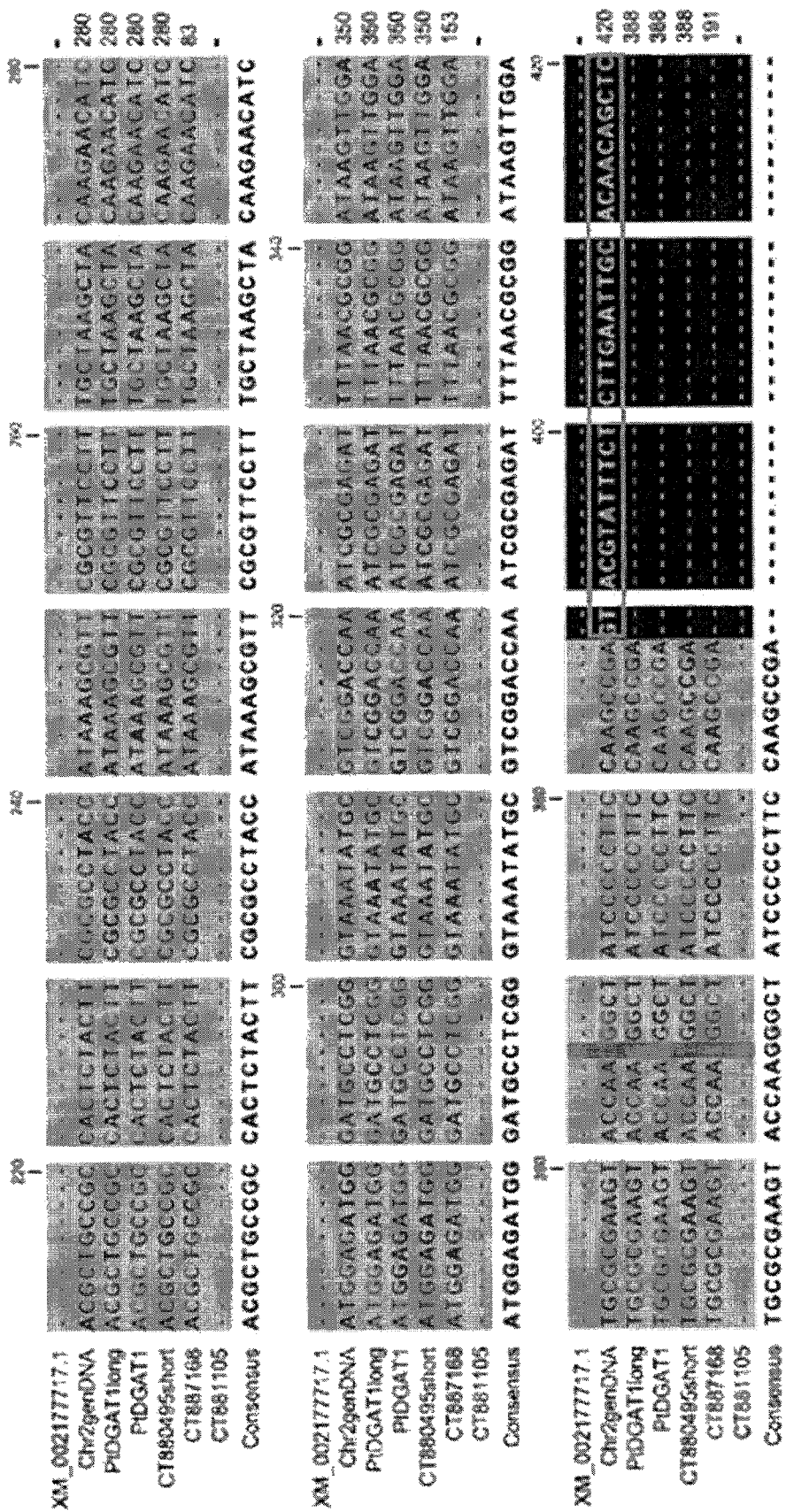
Figure 2:
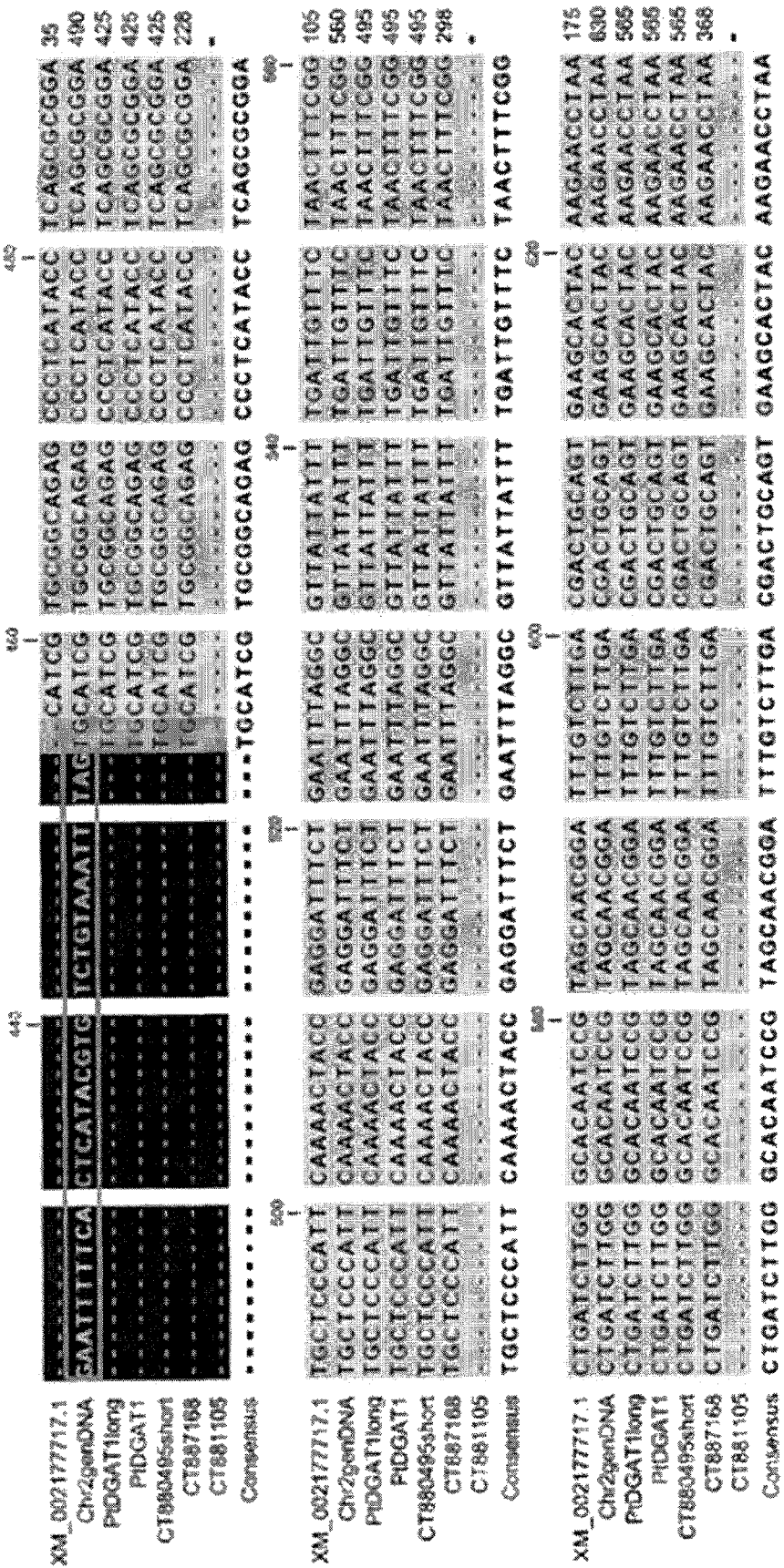
Figure 2:
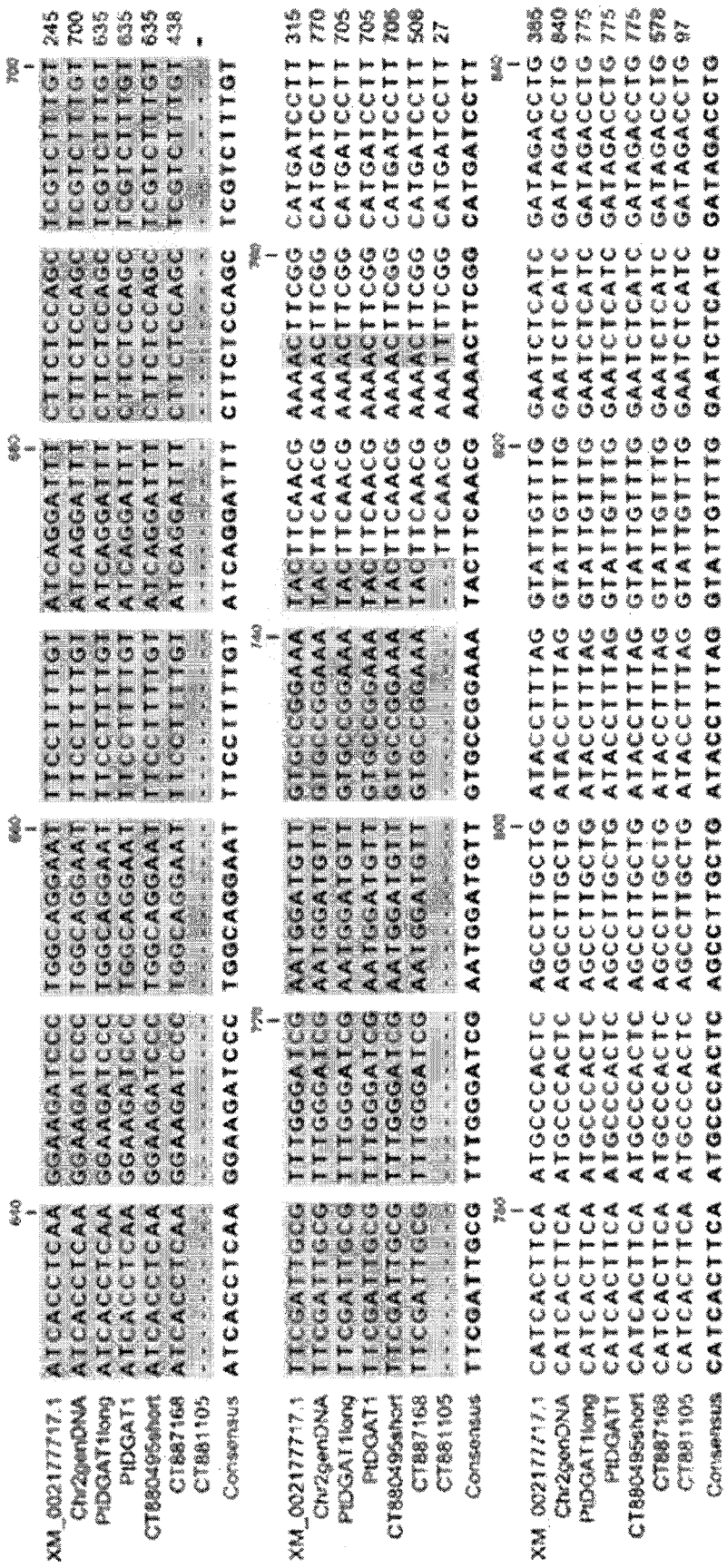
Figure 2:
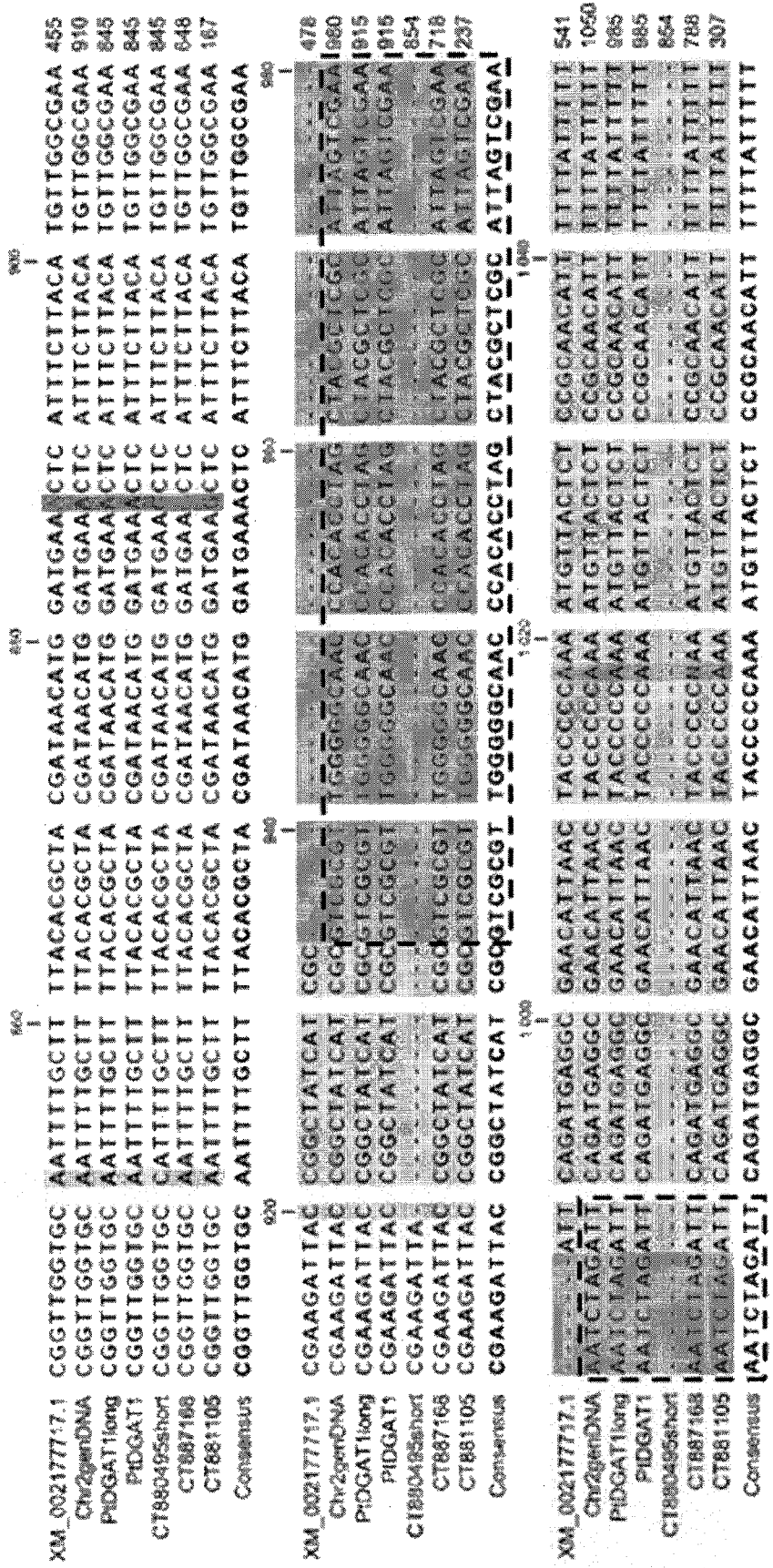
Figure 2:
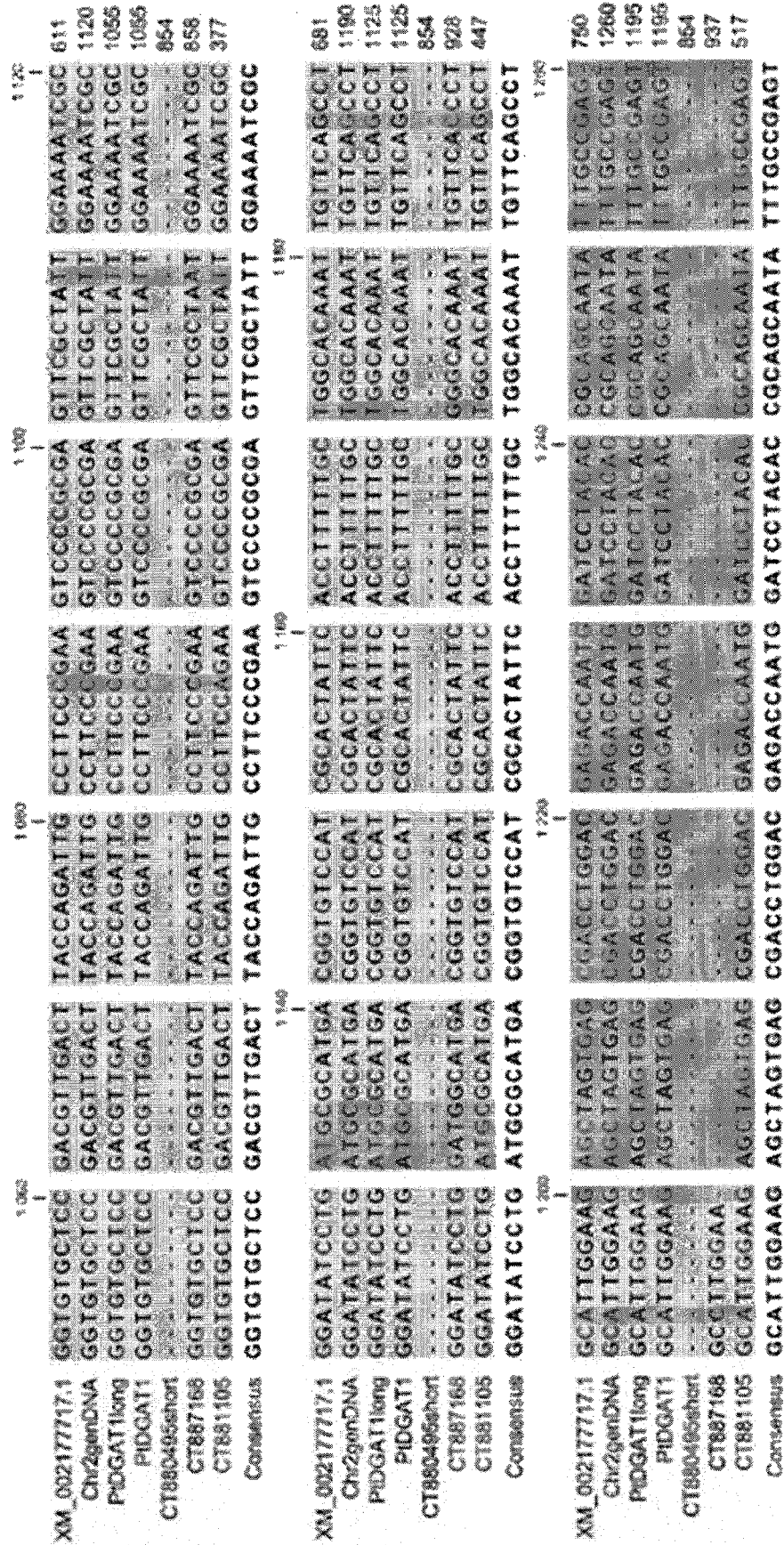
Figure 2:
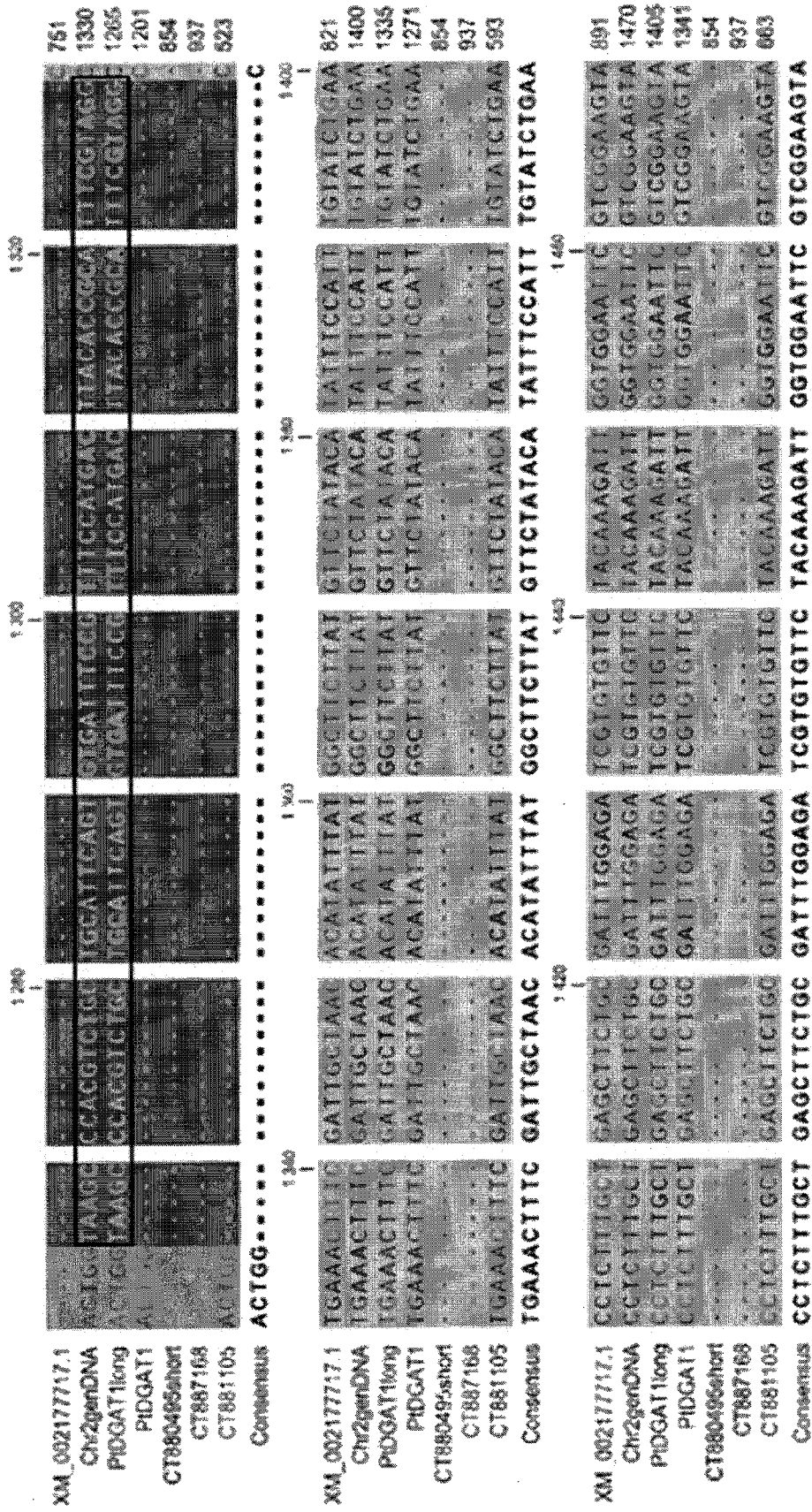
Figure 2:
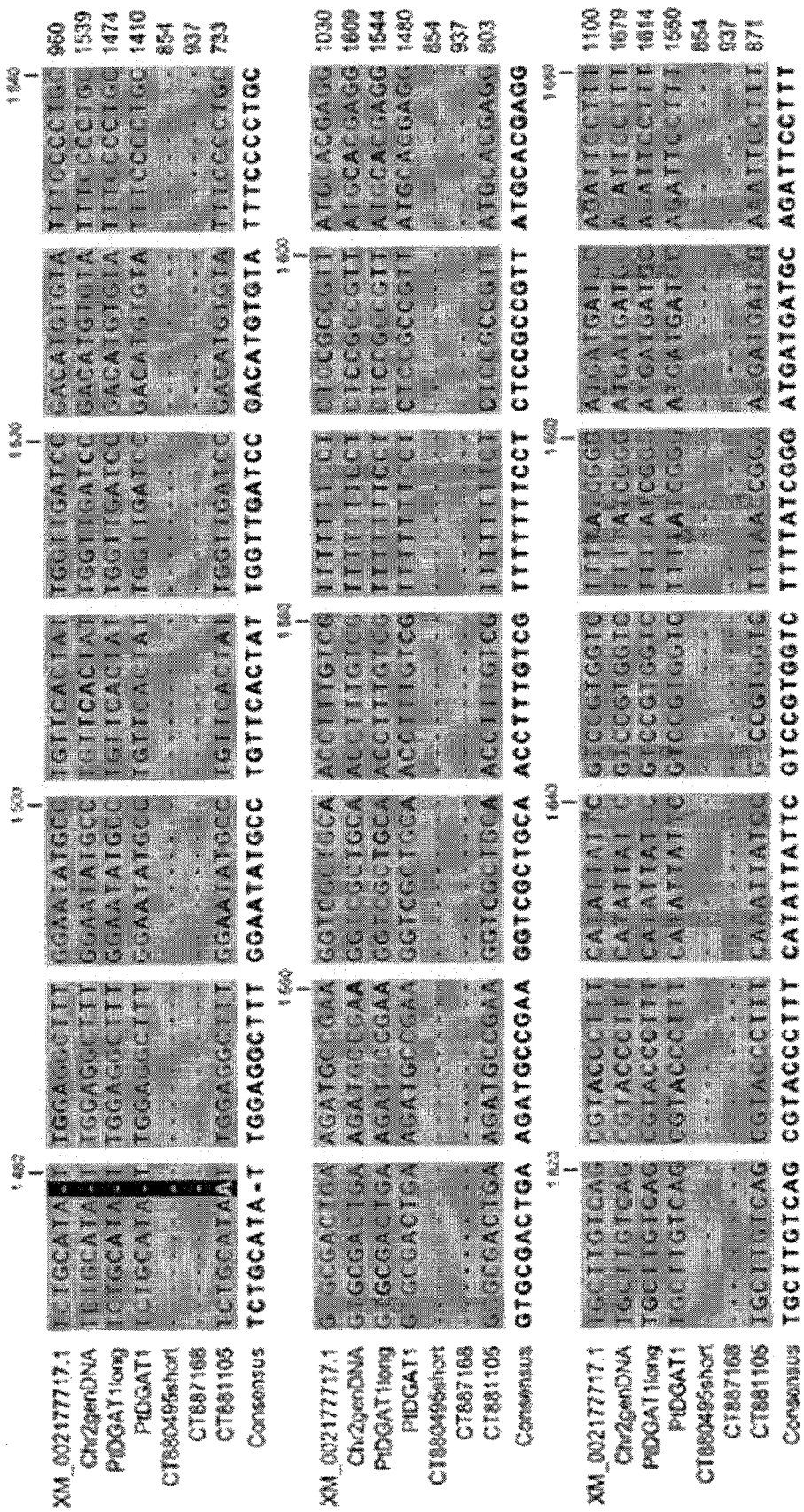
Figure 2:
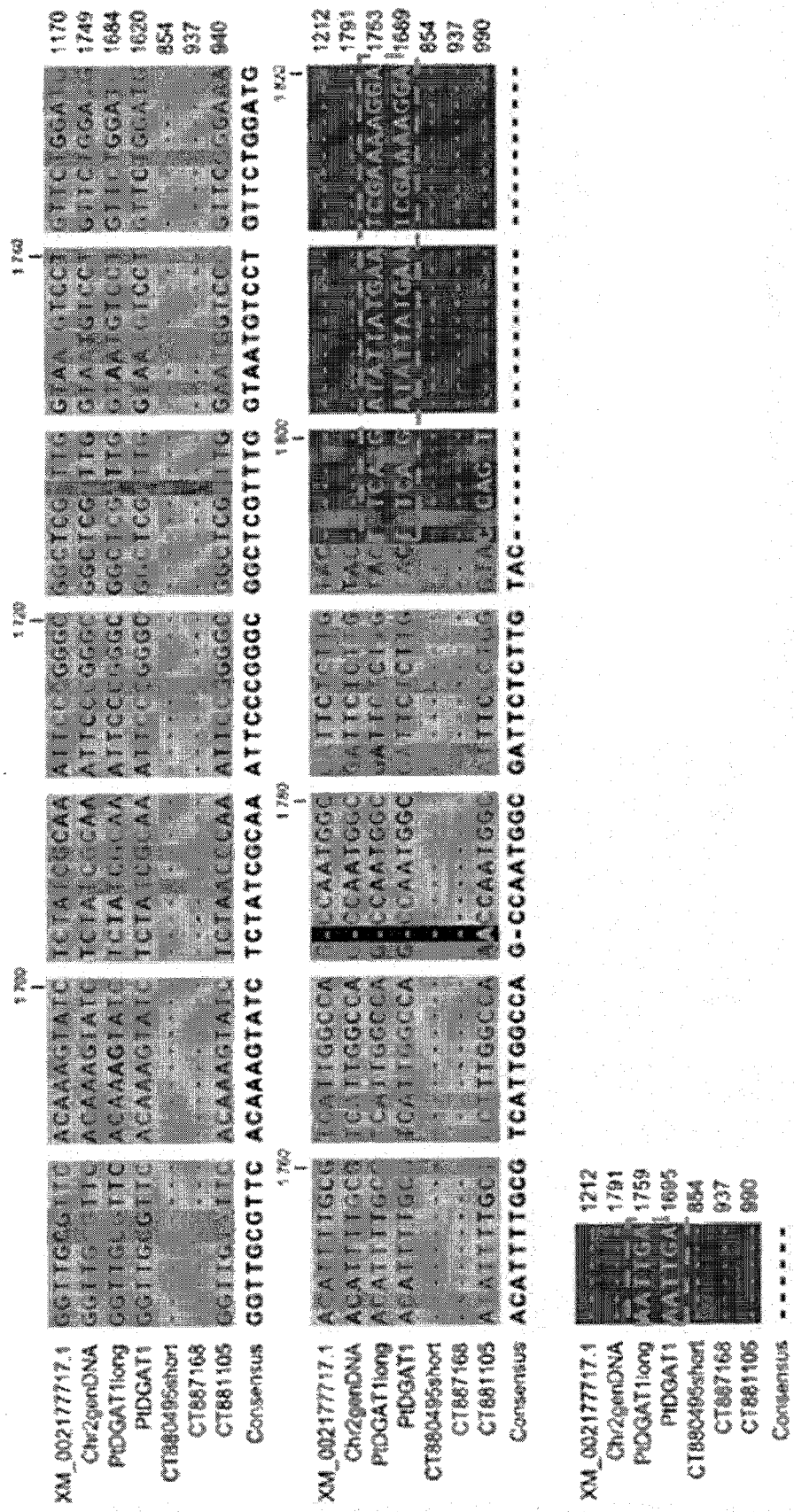

The sequences, PtDGAT1 and PtDGAT1long were aligned, to the *P. tricornutum* chromosome 2 genomic DNA (Bowler et al., 2008) confirming that the 63 bp insert in PtDGAT1long is an intron and in the PtDGAT1 is likely subject to regulated splicing during stress induction or other cellular processes (FIG. 2). The other inserts (54 bp) detected in both cDNA preparations are also present in the genomic DNA sequence.

Example 3

Gene Structure and Phylogenetic Position of PtDGAT1

Figure 5:
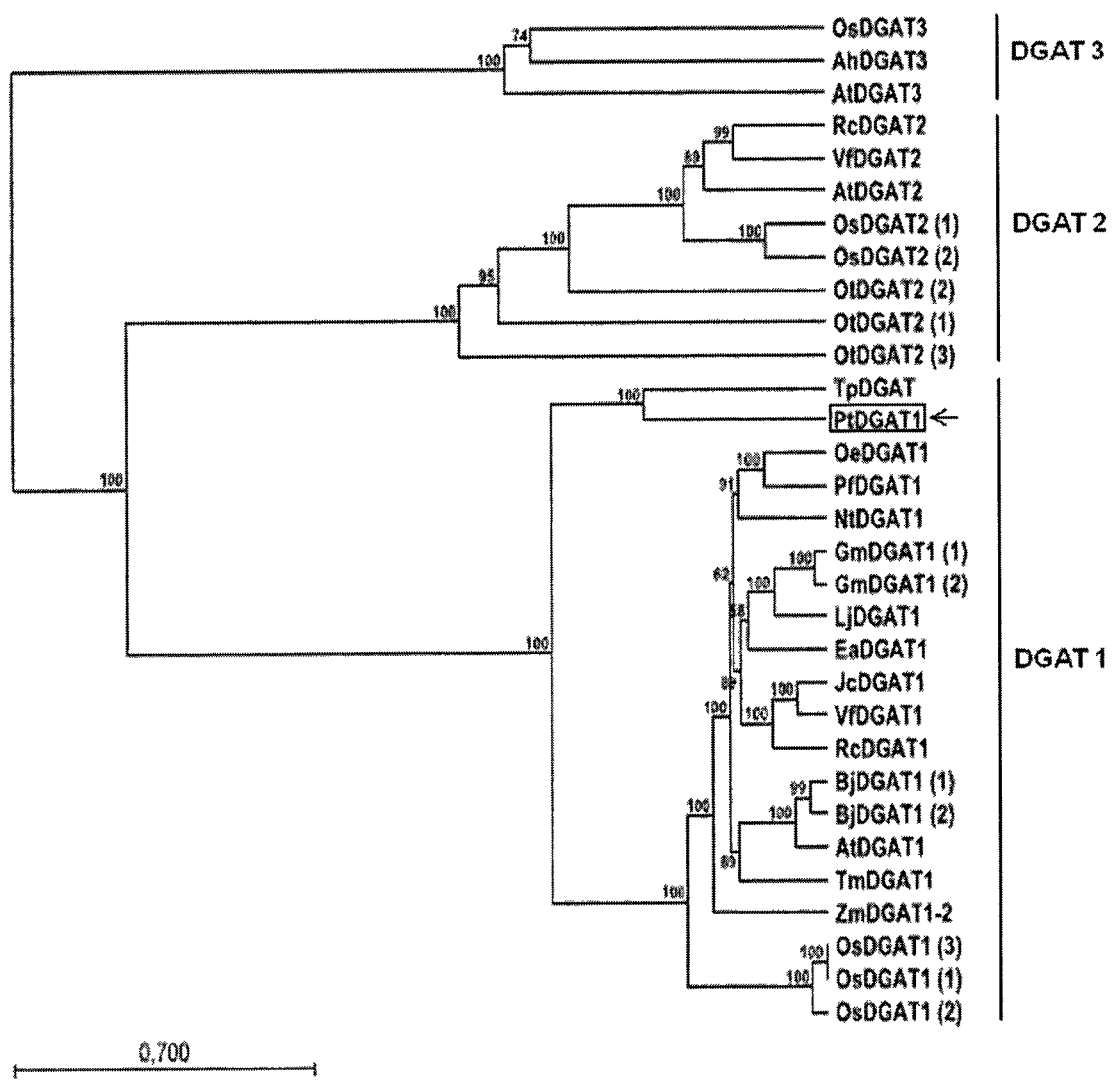
FIG. 5. depicts a phylogram showing relationships among PtDGAT1 and diverse DGAT enzymes from algae and higher plants. The phylogram was calculated based on aligned amino acid sequences using the CLC Sequence Viewer (version 6.3, CLC bio A/S) multiple alignment program. OsDGAT3 (*Oryza sativa*, acc. no NP001054585.1). AhDGAT3 (*Arachis hypoqaea*, acc. no AAX62735.1). AtDGAT3 (*Arabidopsis thaliana*. acc. no NP175263.2). RcDGAT2 (*Ricinus communis*. acc. no XP002528531.1). VfDGAT2 (*Vernicia fordii*. acc. no ABC94473.1). AtDGAT2 (*Arabidopsis thaliana*, acc. no NP566952.1). OsDGAT2(1) and (2) (*Oryza sativa*, acc. no NP001057530.1. and acc. no NP001047917.1). OtDGAT2 (1). (2) and (3) (*Ostreococcus tauri*. acc. no CAL54993.1. acc. no CAL58088.1. and acc. no CAL56438.1). TpDGAT (*Thalassiosira pseudonana*. acc. no XP002287215.1). OeDGAT1 (*Olea europaea*. acc. no AAS01606.1). PfDGAT1 (*Perilla frutescens*. acc. no AAG23696.1). NtDGAT1 (*Nicotiana tabacum*. acc. no AAF19345.1). GrriDGAT1 (1) and (2) (*Glycine max*. acc. no AAS78662.1. and acc. no BAE93461.1). LjDGAT1 (*Lotus japonica*. acc. no AAW51456.1). EaDGAT1 (*Euonymus alatus*. acc. no AAV31083.1). JcDGAT1 (*Jatropha curcas*. acc. no ABB 84383.1). VfDGAT1 (*Vernicia fordii*. acc. no ABC94471.1). RcDGAT1 (*Ricinus communis*. acc. no XP002514132.1). BjDGAT1 (1) and (2) (*Brassica juncea*, acc. no AAY40784.1. and acc. no AAY40785.1). AtDGAT1 (*Arabidopsis thaliana*. acc. no NP179535.1). TmDGAT1 (*Tropaeolum majus*. ace. no AAM03340.2). ZmDGAT1-2 (*Zea mays*, acc. no ABV91586.1). and OsDGAT1 (1). (2) and (3) (*Oryza sativa*. acc. no. NP001054869.2. acc. no. AAV10815.1. and acc. no. NP001054869.1).

The ORF for PtDGAT1 gene obtained from cDNA isolated from algae grown under nitrogen starvation was 1695 bp in length, coding for the corresponding predicted protein of 565 amino acids (FIG. 3). The predicted amino acid sequence of PtDGAT1 is 55% identical to that of *Thalassiosira pseudomona* putative DGAT1 (XP_002287215), while it shares more than 35% identity with DGAT1 of higher plants (FIG. 5-6) and do not share significant homology to DGAT2 proteins from higher plants and algae. DGAT1 of diatoms (a putative TpDGAT and PtDGAT1) form a separate branch on the phylogenetic tree from the higher plant DGAT1 proteins. It is important to mention that no ortholog genes were found in the green algae. DGATs in the available genomes of Chlorophyte are represented by DGAT2.

Figure 4A:
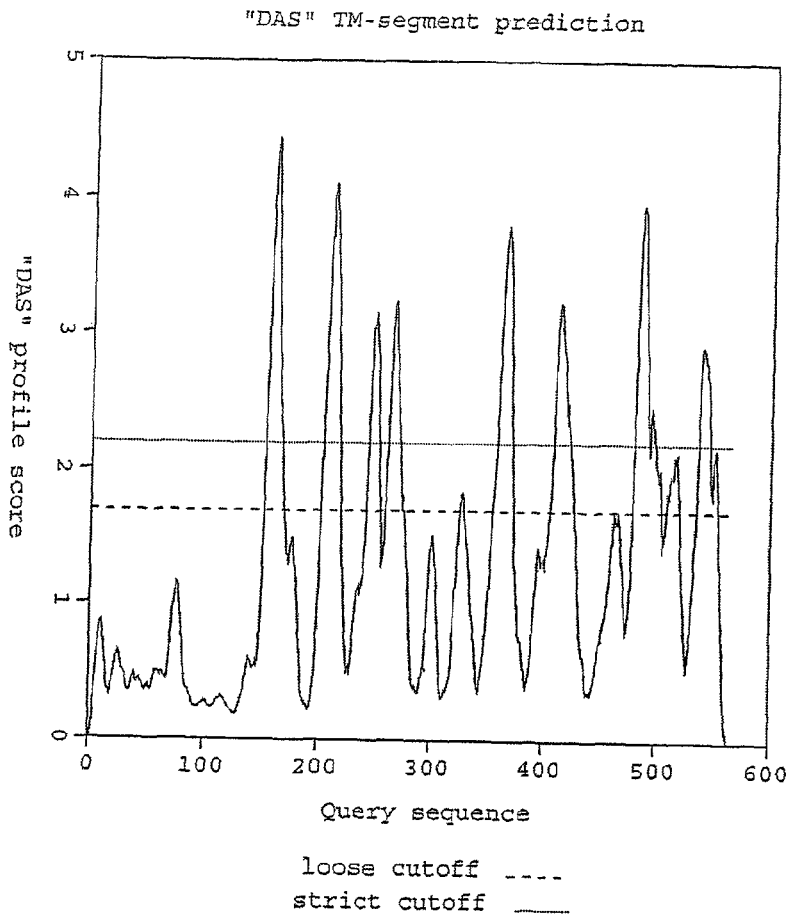
FIG. 4. depicts hydrophobicity plots indicating at least 8 transmembrane regions of strong hydrophobicity [created using DAS (top) and TMHMM servers (bottom)].
Figure 4B:
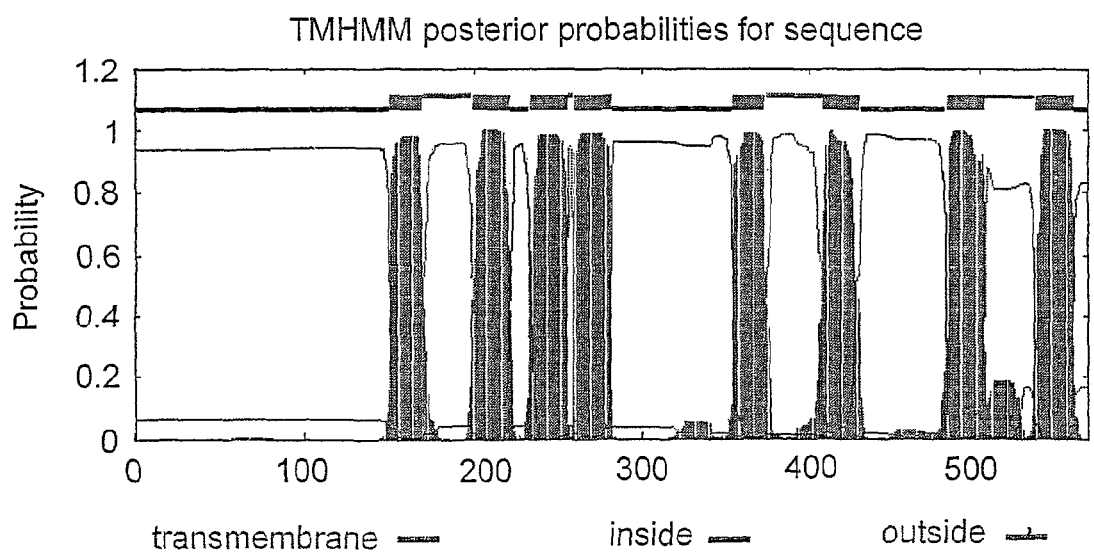
Figure 6:
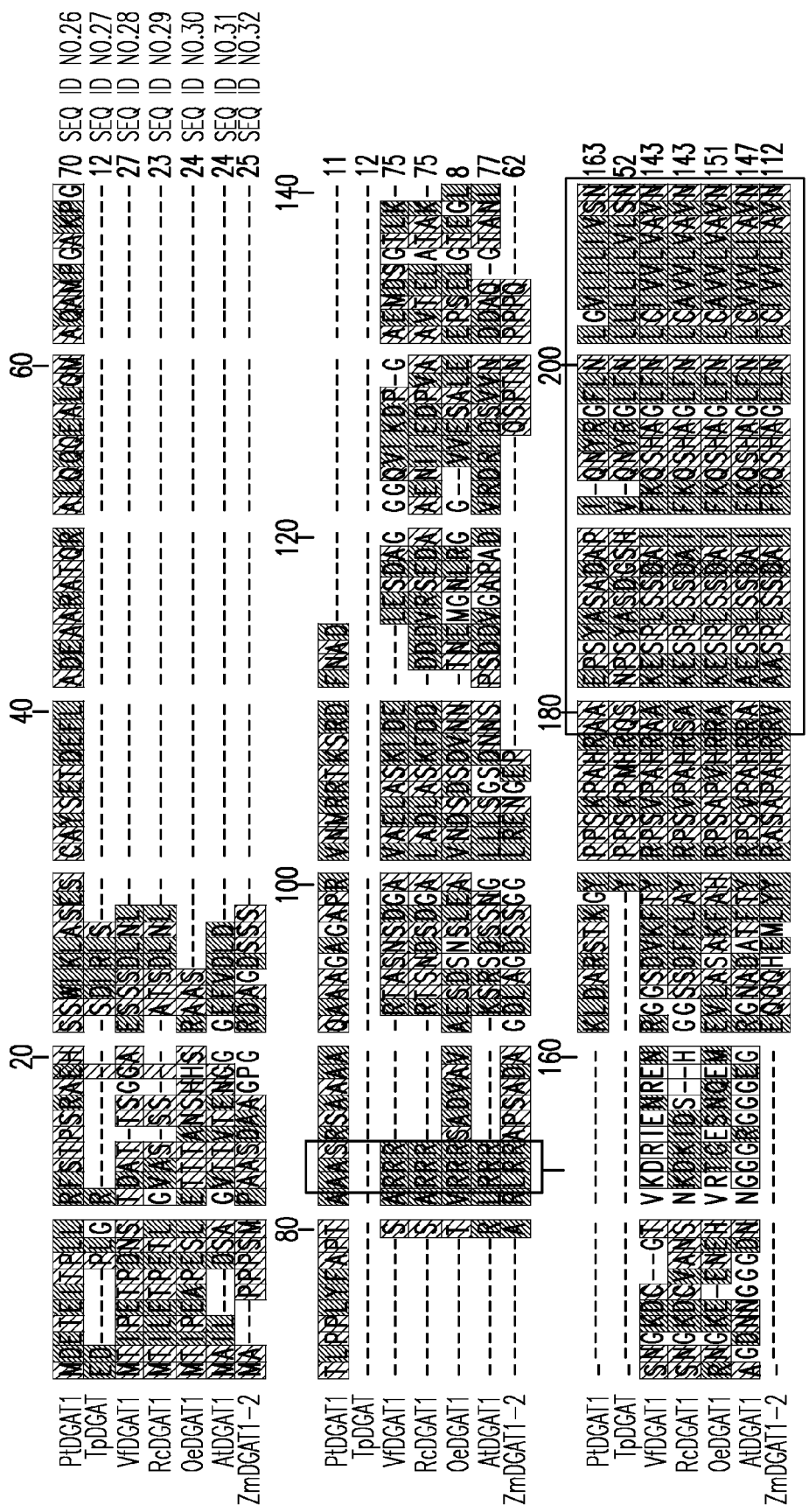
FIG. 6. depicts sequence comparison of PtDGAT1 with the DGAT hypothetical protein of the diatom *Thalassiosira pseudonana* and related DGAT1 enzymes from higher plants. TpDGAT (*T. pseudonana*, acc. no XP002287215.1), OeDGAT1 (*Olea europaea*, ace. no AAS01606.1), VfDGAT1 (*Vernicia fordii*, acc. no ABC94471.1), ReDGAT1 (*Ricinus communis*, acc. no XP002514132.1), AtDGAT1 (*Arabidopsis thaliana*, acc. no NP179535.1), ZmDGAT1-2 (*Zea mays*, acc. no ABV91586.1). Conserved motifs or putative signature (see text for details) are boxed, such as N-terminal basic motif RRR in higher plants substituted by KRS in PtDGAT1 (I), the Acyl-CoA binding signature (II), the fatty acid protein signature (III) which contains a tyrosine phosphorylation site (♦), the DAG-binding (IV), and two C-terminal motifs YYHDI-like YYHDV (V) and KKXX-like NRGK (VI) as putative endoplasmic reticulum retrieval motifs ER-DIR in the C-terminus. The region containing a conserved leucine repeat (L) in higher plants coinciding with a thiolase acyl enzyme intermediate binding signature besides critical Pro and Ser residues which are marked by asterisks. The conserved phenylalanine is designated by arrow.
Figure 6:
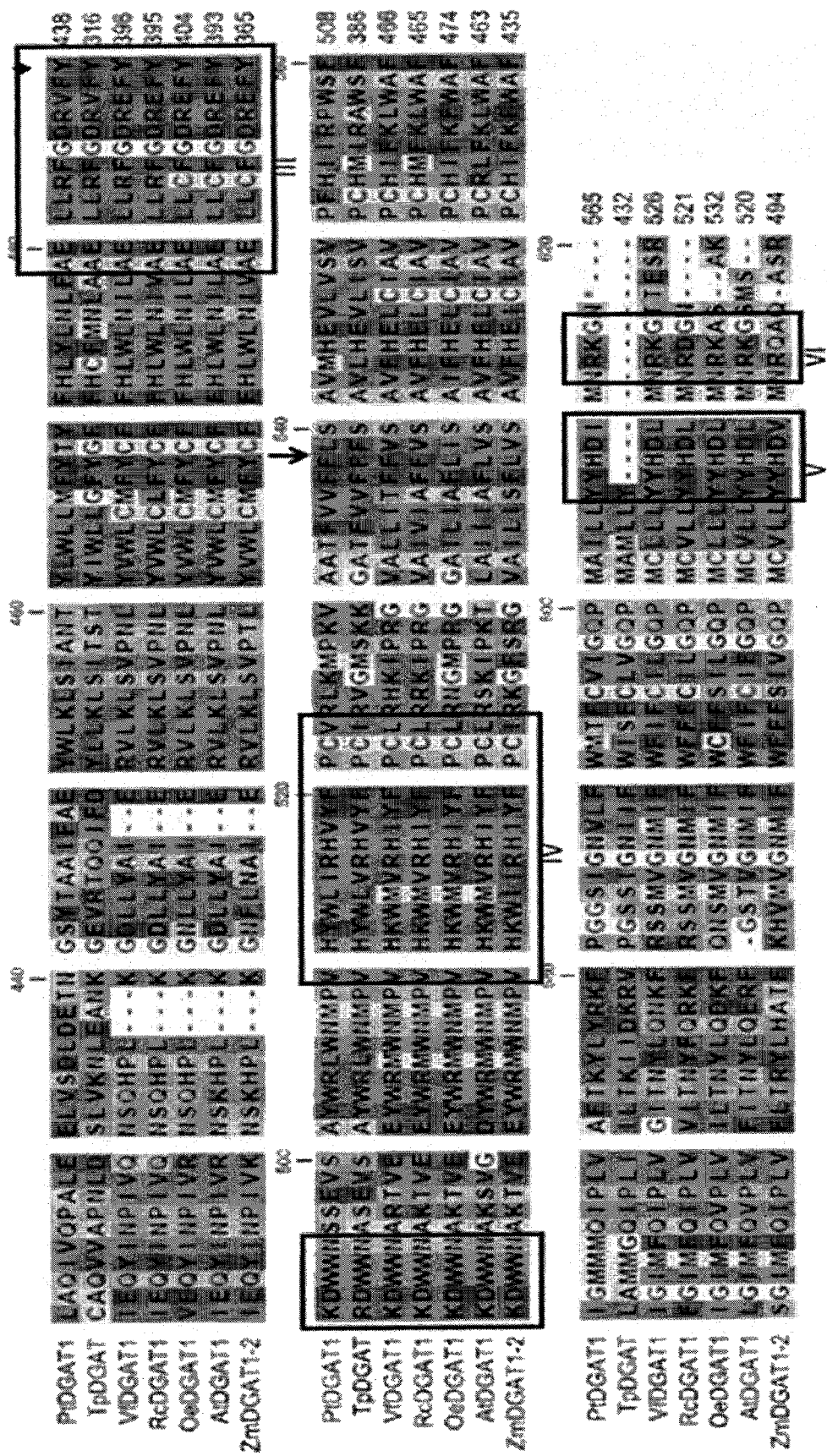

At least 8 trans-membrane regions of strong hydrophobicity (FIG. 4) were predicted by various algorithms (Das, Phobious and TMHMM, online software) that are likely to anchor the protein to the endoplasmic reticulum (ER) membrane, a characteristic feature of DGAT1 proteins in agreement with the putative assessment of PtDGAT1 as DGAT1. Moreover, the conserved motifs or putative signatures found in higher plants are slightly different in PtDGAT1 (FIG. 6). The characteristic basic motif found in amino acid N-terminal domain, consisting of three arginine residues (RRR) in higher plants (Bouvier-Navé et al., 2000; Xu et al., 2008; Mañas-Fernández et al., 2009), is substituted by KRS in PtDGAT1. The previously reported Acyl-CoA binding signature $A^{133}$-$R^{172}$ and the DAG-binding motif $V^{458}$-$V^{471}$ involved in the active site are also found in the PtDGAT1 similarly to other DGAT1 proteins of plants (Jako et al., 2001; Mañas-Fernández et al., 2009). There is also a fatty acid binding protein signature spanning residues $A^{427}$ to $N^{443}$, which contains a putative tyrosine phosphorylation site $Y^{438}$ (Xu et al., 2008). Concerning the leucine zipper motif besides previously described critical Pro and Ser residues coinciding with a thiolase acyl enzyme intermediate binding signature in higher plants (Zou et al., 1999; Xu et al., 2008), only two of the six conserved leucine are present in PtDGAT1. Also relevant is the presence of the two C-terminal motifs YYHDI-like (SEQ ID NO 15) YYHDV (SEQ ID NO 16) (Mañas-Fernández et al., 2009) or NRGK-KKXX-like (SEQ ID NO 17) (WolfPSORT prediction software) confirming the putative ER retrieval motifs in the C-terminus.

Example 4

Putative Intron Retention Alternatively Splicing

Under nitrogen starvation, the nucleotide sequence of PtDGAT1 was missing the 63 bp insert (insert II) which can be a result of an intron retention alternatively splicing. This mechanism, by which multiple forms of mature mRNAs are produced from a single transcript, just after the transcripts synthesis, is the most common alternative splicing in *Arabidopsis* and rice (>50%, Ner-Gaon et al., 2004; Kim et al., 2007).

Moreover, the amino acid sequences resulting from both forms of mRNA show that the insert II introduces stop-codons into the ORF of the PtDGAT1 mRNA. Indeed, mRNAs with intron retention lead to truncated polypeptides, or are subjected to nonsense-mediated mRNA decay, as retained introns often introduce in frame stop-codons (Maquat, 2004). The production of a truncated transcript and protein product at the expense of the corresponding active enzyme form could play role in regulating the amount of active protein produced, depending on the level of correctly spliced transcript. A higher amount of the active DGAT1 protein produced could thus provide an explanation at molecular level for the TAG content increase in *P. tricornutum* and generally in microalgae induced by nitrogen starvation.

Example 5

Heterologous Expression of PtDGAT1 in *S. cerevisiae*

Figure 7:
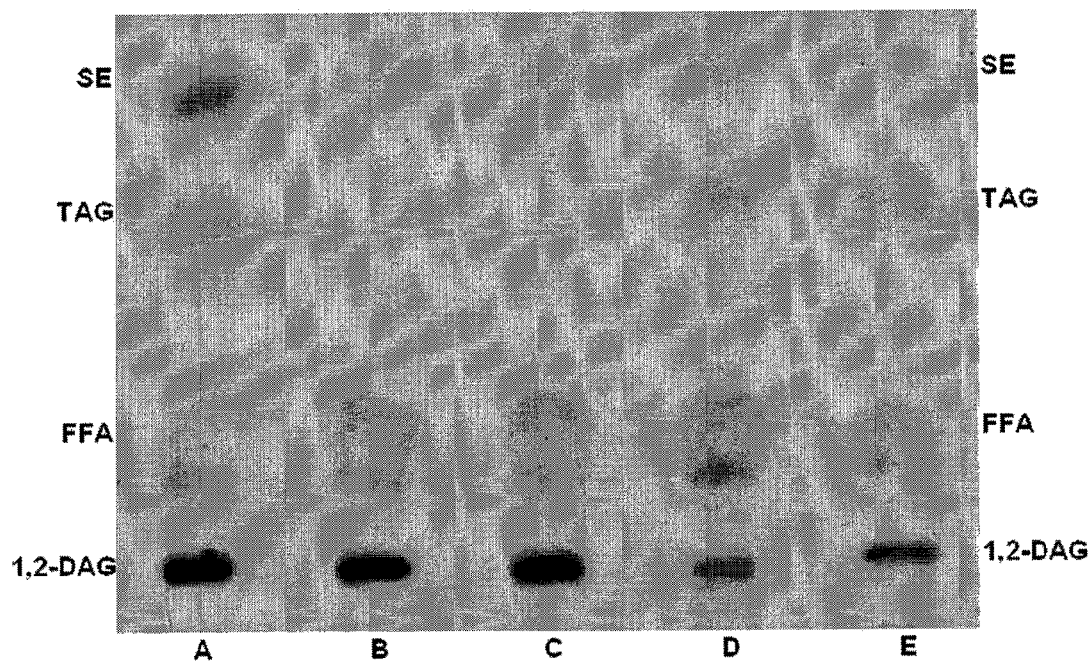
FIG. 7. is a silica-gel micrograph showing the complementation of the TAG deficient phenotype of the yeast mutant H1246 by expression of PtDGAT1. The expression was performed for 48 h at 30° C. Lipid extracts were separated by TLC, and lipid spots visualized as described in Material and Methods. As positive control, the wild type BY742 harboring the empty plasmid was used (A). As negative control, the NL-deficient quadruple mutant strain H1246 harboring the empty plasmid (B). The NL-deficient quadruple mutant strain H1246 was not expressing PtDGAT1 because of the 63 bp insert introducing stop codons into the ORF (C). The mutant strain H1246 was expressing PtDGAT1 (D). As second positive control, the NL-deficient quadruple mutant strain H1246 was expressing the yeast DGA1 gene (E). SE: Steryl Esters. TAG: Triacylglycerol. FFA: Free Fatty Acids. 1.2-DAG: 1.2-Diacylglycerol.

To verify whether PtDGAT1 indeed encodes a protein with DGAT activity, the gene was expressed in a *S. cerevisiae* neutral lipid-deficient quadruple mutant strain H1246, containing knockouts of the DGA1, LRO1, involved in the formation of TAG, ARE1 and ARE2 genes, involved in the formation of sterol esters. The yeast cells harboring the empty pYES2 vector were used as control, the BY742 strain and the H1246 as negative control. Moreover, the H1246 expressing the yeast DGA1 gene was also used as positive control. The total lipid extracts of the yeast cells were prepared and then subjected to TLC. In the neutral lipid-deficient quadruple mutant strain H1246, TAG were not detected, whereas the ability to form TAG was confirmed in the wild type BY742 and the H1246 expressing the yeast DGA1 gene strain, as positive controls (FIG. 7). Upon expression of the PtDGAT1, a prominent spot corresponding to TAG appeared on the chromatograms of the lipid extract of the yeast mutant cells (H1246), showing a successful restoration of the TAG deficient phenotype by the PtDGAT1 activity (FIG. 7). As expected, the expression of the PtDGAT1long with the intron retention introducing stop-codons did not complement the mutation and did not restore the ability of yeast mutant strain to synthesize TAG. This result indicates that the mRNA with intron retention lead to production of truncated polypeptides and absence of DGAT activity.

Example 5

Formation of Lipid Bodies is Restored Upon Expression of PtDGAT1

Figure 8A:
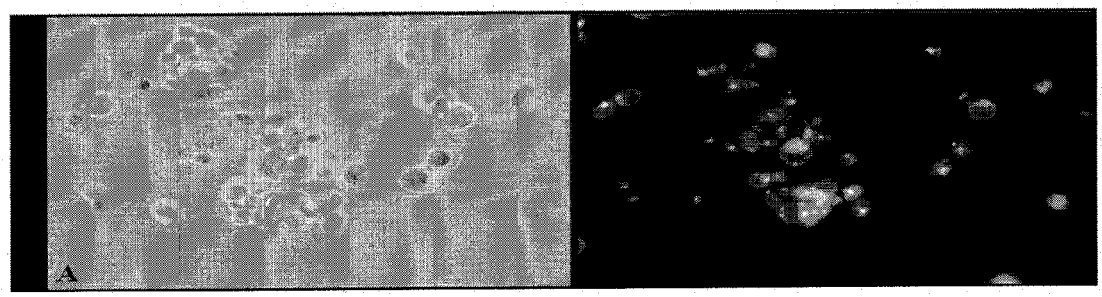
FIG. 8. is a set of microscopic micrographs showing that the formation of lipid bodies is restored upon expression of PtDGAT1 in the yeast strain H1246. Neutral Lipid (NL) accumulation in lipid bodies was visualized in yeast cells using the fluorescent dye Nile Red. As positive control, the wild type BY742 harboring the empty plasmid was used (A). As negative control, the NL-deficient quadruple mutant strain H1246 harboring the empty plasmid (B). The NL-deficient quadruple mutant strain H1246 was not expressing PtDGAT1 because of the 63 bp insert introducing stop codons into the ORF (C). The mutant strain H1246 was expressing PtDGAT1 (D). As second positive control, the NL-deficient quadruple mutant strain H1246 expressing the yeast DGA1 gene (E).
Figure 8B:
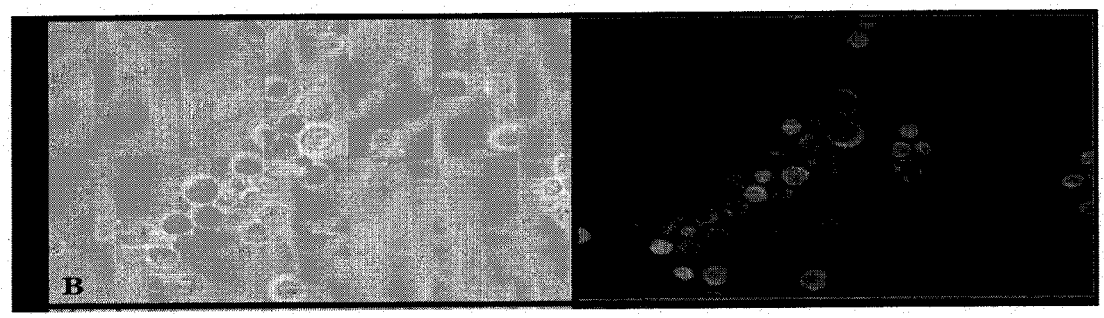
Figure 8C:
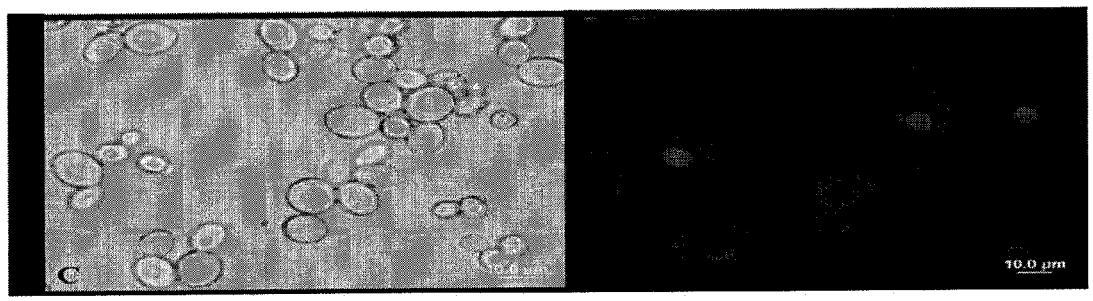
Figure 8D:
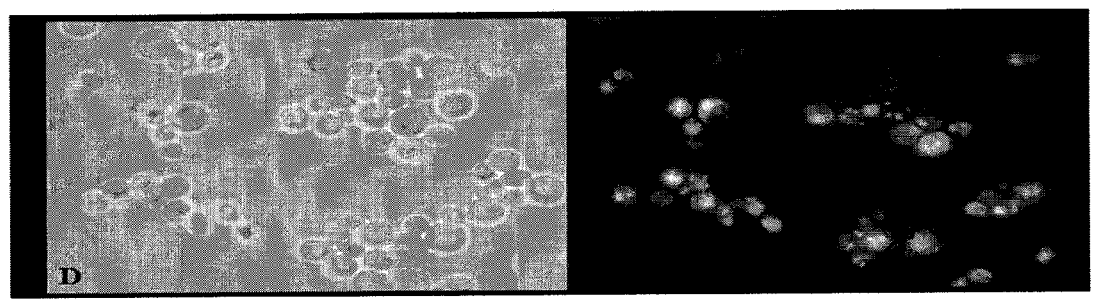
Figure 8E:
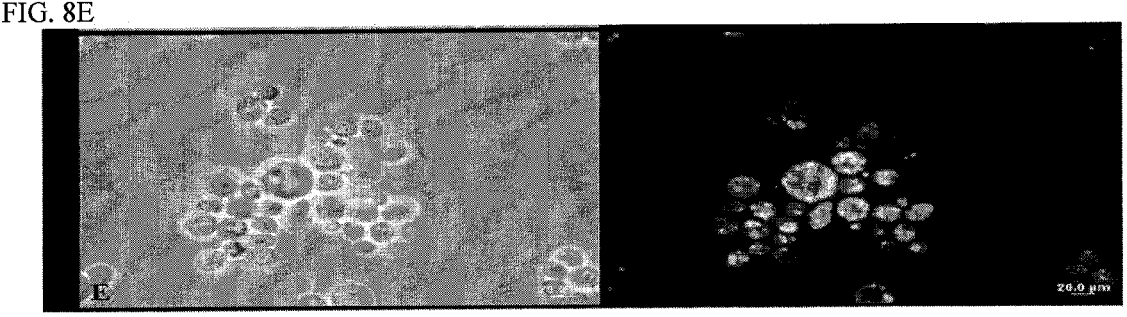

The activity of one of the knock-out genes is sufficient to restore formation of lipid bodies in the NL-deficient quadruple mutant strain H1246 (Sandager et al 2002). To determine if the heterologous expression of PtDGAT1 was able to restore the formation of oil bodies, the fluorescent dye Nil Red was used to stain the lipid bodies in the quadruple mutant H1246 after transformation and in the BY742 strain served as control. The results have shown that expression of PtDGAT1 restored the ability to form lipid bodies, as well as the expression of the yeast DGA1 gene (FIG. 8D vs. E). As expected no TAG formation was observed following expression of PtDGAT1 long containing the 63 bp insert and harboring stop-codons (FIG. 7C), since, the intron retention introduces in frame stop-codons and leads to the loss of DGAT activity.

Example 6

Substrate Fatty Acid Specificity of PtDGAT1

The predominant molecular species of TAG in *P. tricornutum* under starvation conditions are composed of 46:1, 48:1, 48:2, and 48:3 (total of carbon chains: total of double bonds) molecular species, having palmitic (16:0), palmitoleic (16:1), and myristic (14:0) acid constituents. However the alga can accumulate a certain percentage of VLC-PUFAs, EPA (20:5 n-3) and TAG molecular species with higher degree of unsaturation containing 20:4 n-6, 20:5 n-3 and 22:6 n-3, at lesser scale are also detectable (Yu et al., 2009).

Further it was tested whether the expression of the active form of PtDGAT1, isolated at nitrogen starvation conditions, could facilitate the incorporation of various PUFAs into the yeast TAG in comparison with the endogenous DGAT1 activity encoded by DGA1 Consequently, the supplementation assay (Table 3) was carried out by using various polyunsaturated C18- and C20-fatty acids of both ω3 and ω6 groups naturally present in *P. tricornutum*, but not in *S. cerevisiae*, to investigate the possible acyl-CoA preference of PtDGAT1. *P. tricornutum* utilizes multiple biosynthetic pathways and fatty acid intermediates for EPA biosynthesis (Arao et al., 1994). *S. cerevisiae* is able to import exogenous FAs from the medium and convert them to respective acyl-CoA derivatives to be incorporated in polar lipids and TAG, thus supplementation of the medium with FA can further enhance the TAG accumulation conferred by the recombinant DGAT gene (Siloto et al., 2009). In the absence of supplemented fatty acids, the recombinant DGATs utilized available endogenous DAG and acyl-CoA pool for the acylation at the third position of glycerol. As can be seen from the Table 3, PtDGAT1 showed a clear preference for endogenous saturated 16:0 and 18:0 species relative to the yeast DGA1 which was more selective towards monounsaturated 16:1 and 18:1. Thus TAG formed by action of PtDGAT1 is substantially more saturated relative to the one formed by the yeast DGA1

TABLE 3

Fatty acid composition of TAG isolated from H1246 yeast cells transformed with pYES2 containing PtDGAT1 and yeast DGA1. Cultures were supplemented or not with 250 μM ALA, GLA, ETA, ARA, and EPA. Mean values (n = 3) are expressed as percentage of total fatty acids in the TAG fraction.

| SFA/MUFA* | Supp. FA | 18:1 n-9 | 18:0 | 16:1n-7 | 16:0 | Gene | Substrates |
|---|---|---|---|---|---|---|---|
| 0.53 | — | 31.9 | 13.8 | 28.6 | 17.7 | PtDGAT1 | not supplemented |
| 0.19 | — | 39.6 | 7.3 | 37.0 | 7.4 | DAG1 | |
| 1.03 | 12.7 | 19.4 | 14.9 | 21.3 | 27.0 | PtDGAT1 | ALA |
| 0.45 | 18.4 | 22.9 | 8.3 | 29.6 | 15.3 | DAG1 | |
| 1.36 | 19.5 | 14.0 | 13.4 | 17.3 | 29.1 | PtDGAT1 | GLA |
| 0.53 | 30.2 | 17.8 | 7.6 | 23.8 | 14.3 | DAG1 | |
| 0.70 | 5.6 | 23.0 | 13.7 | 28.2 | 22.4 | PtDGAT1 | ETA |
| 0.21 | 12.4 | 28.0 | 5.3 | 40.3 | 8.9 | DAG1 | |
| 0.85 | 3.2 | 21.7 | 13.7 | 26.7 | 27.5 | PtDGAT1 | ARA |
| 0.25 | 9.2 | 29.5 | 6.5 | 38.9 | 10.3 | DAG1 | |
| 0.93 | 10.6 | 20.6 | 13.8 | 22.3 | 25.9 | PtDGAT1 | EPA |
| 0.35 | 11.5 | 30.6 | 7.6 | 31.4 | 13.2 | DAG1 | |

*ratio 16:0 + 18:0/16:1 + 18:1

The abilities of PtDGAT1 and the yeast DGA1 to incorporate PUFA into TAG were compared. The fatty acid analysis of TAG showed incorporation of all supplemented PUFAs upon expression of both PtDGAT1 and DGA1. Surprisingly, the expression of yeast DGA1 resulted in higher levels of both C18 and C20 PUFA in TAG, except for similar 20:5 n-3 incorporation, even if these fatty acids are not naturally present in yeast. Similar results have been shown by Wagner et al. (2010) by comparison of the *Ostreococcus tauri* DGAT2 and yeast DGA1 substrate specificity, where algal and yeast enzymes were shown to be promiscuous towards available acyl-CoA substrate and displayed a similar fatty acid preference. The expression of both PtDGAT1 and DGA1 resulted in higher incorporation of the C18-PUFA relative to C20-PUFA into TAG. Incorporation of 18:3 n-3 and 18:3 n-6 into TAG of the recombinant yeast was associated with a corresponding decrease in the proportion of both mono-unsaturated 16:1 n-7 and 18:1 n-9 fatty acids and an increase in the proportion of 16:0. Whereas TAG of the transformed yeasts supplemented with 20:3 n-3, 20:4 n-3, and 20:5 n-3 featured only a decrease in 18:1 n-9. From these data, it can be suggested that exogenous C18-PUFA competed with 16:1 n-7 and 18:1 n-9 in yeast expressing both recombinant PtDGAT1 and DGA1, C20-PUFA were mainly incorporated at the expense of endogenous 18:1 n-9. Importantly, TAG formed by the activity of PtDGAT1 was substantially more saturated, once more indicating to the preference for saturated fatty acid species. While cells expressing DGA1 incorporated n-6 C20-PUFA into TAG at higher proportions than cells expressing PtDGAT1, the similar incorporation of 20:5 n-3 was determined upon expression of both PtDGAT1 and DGA1. These results confirm the ability of PtDGAT1 to accumulate 20:5 n-3, one major PUFA in diatoms, into TAG and allow speculating that PtDGAT1 prefers n-3 C20-PUFA over n-6 C20-PUFA. That was not a case with DGA1 that demonstrated a similar incorporation of C20-PUFA of both groups.

In conclusion, these results have shown a preference of PtDGAT1 to produce TAG species with high level of saturated fatty acids (16:0 and 18:0) in a heterologous system. The highly unsaturated plant oils used for biodiesel production are often prone to oxidation more rapidly than conventional diesel, resulting in formation of insoluble sediments that interfere with engine performance (Deng et al., 2009). The capability of PtDGAT1 to incorporate saturated fatty acids such as 16:0 into TAG species is a beneficial feature for biodiesel production from microalgal and even plant oils, which are generally characterized by higher than necessary unsaturation level.

Example 7

Cloning of the Full-Length PtDGAT1

The ORF for the full-length PtDGAT1 gene, including Pleckstrin Homology (PH) domain recently obtained from cDNA isolated from algae grown under nitrogen starvation was 2271 bp in length, coding for the corresponding protein of 756 amino acids (FIG. 9). The putative full-length cDNA sequence, which contains the PH domain, is assumed to contain the genuine translation initiation codon, and the native C-terminal sequence encoding for the endoplasmatic reticulum retrieval motif of *P. tricornutum*. The 100-120 amino acids of PH domains are only found in eukaryotes, share little sequence conservation and have diverse functions. They are often involved in targeting proteins to the plasma membrane, but few display strong specificity in lipid binding (Lemmon Mass., 2011. Pleckstrin Homology (PH) domains. Transduction mechanisms in cellular signaling: cell signaling collection. Eds: Edward A. D., Ralph A. B., Vol. 3, $2^{nd}$ edition, Elsevier inc., 239-247).

What is claimed is:

1. An isolated polynucleotide comprising a cDNA coding portion encoding a Diacylglycerol Acyltransferase protein comprising the amino acid sequence set forth in SEQ ID NO: 1.

2. An isolated polynucleotide comprising a cDNA coding portion of claim 1 encoding a Diacylglycerol Acyltransferase, comprising the amino acid sequence set forth in SEQ ID NO: 3.

3. An isolated polynucleotide comprising a cDNA coding portion of claim 1 encoding a Diacylglycerol Acyltransferase, comprising the amino acid sequence set forth in SEQ ID NO: 4.

4. A composition comprising the polynucleotide of claim 1 and a carrier.

5. An expression vector comprising the polynucleotide of claim 1.

6. A cell comprising the expression vector of claim 5.

7. A transgenic organism or a transformed bacteria transformed by the polynucleotide of claim 1.

8. The organism of claim 7, wherein said organism is a plant, a seed, a heterotrophic microorganism, a bacterium, a yeast, a microalga, or an alga.

9. A transgenic seed, produced by a transgenic plant transformed by the polynucleotide of claim 1.

10. A method for enhancing the production of oil or triacylglycerols with high saturated fatty acids content in a cell, comprising the step of transforming said cell with a polynucleotide of claim 1, thereby enhancing a production of oil or triacylglycerols with high saturated fatty acids content in a cell.

11. The method of claim 10, wherein said cell is a plant cell, a seed cell, a heterotrophic microorganism cell, a bacterium, a yeast, a microalgal cell, or an algal cell.

12. The method of claim 11, wherein said algal or microalgal cell is grown under nitrogen starvation conditions.

13. A method of increasing the proportion of a saturated fatty acid in a cell, comprising the step of transforming said cell with a polynucleotide of claim 1, thereby increasing the proportion of a saturated fatty acid in a cell.

14. The method of claim 13, wherein said increasing the proportion of a saturated fatty acid comprises decreasing the proportion of an unsaturated fatty acid.

15. The method of claim 13, wherein said cell is a plant cell, a seed cell, a heterotrophic microorganism cell, a bacterium, a yeast, a microalgal cell, or an algal cell.

16. The method of claim 14, wherein said algal or microalgal cell is grown under nitrogen starvation conditions.

17. The method of claim 13, wherein said saturated fatty acid is 16:0 or 18:0.

18. The method of claim 14, wherein said unsaturated fatty acid is 16:1 or 18:1.

* * * * *